(12) United States Patent
De Jonge

(10) Patent No.: US 9,207,196 B2
(45) Date of Patent: Dec. 8, 2015

(54) TRANSMISSION ELECTRON MICROSCOPY FOR IMAGING LIVE CELLS

(75) Inventor: Niels De Jonge, Brentwood, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 1056 days.

(21) Appl. No.: 13/299,241

(22) Filed: Nov. 17, 2011

(65) Prior Publication Data

US 2012/0120226 A1    May 17, 2012

Related U.S. Application Data

(60) Provisional application No. 61/414,603, filed on Nov. 17, 2010.

(51) Int. Cl.
| | |
|---|---|
| *G01N 23/00* | (2006.01) |
| *G01N 23/22* | (2006.01) |
| *G01N 23/225* | (2006.01) |
| *H01J 37/20* | (2006.01) |
| *B01L 3/00* | (2006.01) |

(52) U.S. Cl.
CPC ........ *G01N 23/2204* (2013.01); *G01N 23/2251* (2013.01); *H01J 37/20* (2013.01); *B01L 3/502715* (2013.01); *H01J 2237/2003* (2013.01); *H01J 2237/2004* (2013.01); *H01J 2237/2802* (2013.01)

(58) Field of Classification Search
CPC .................. H01J 2237/2003; G01N 23/00
USPC ......................................................... 348/80
See application file for complete search history.

(56) References Cited

PUBLICATIONS

N. de Jonge, "Electron micorscopy of whole cells in liquid with nanometer resolution". PNAS, Feb. 17, 2009, vol. 106, No. 7, pp. 2159-2164. www.pnas.org/cgi/doi/10.1073/pnas.0809567106.*
Elisabeth Ring, "Microfluidic System for Transmission Electron Microscopy", Microscope and Micranalysis, 16, , pp. 622-629 (2010).*
J. Lippincott-Schwartz et al., Studying protein dynamics in living cells, Nature Reviews, 2, p. 444-456 (2001).
S. W. Hell, Far-field optical nanoscopy, Science, 316, p. 1153-1158 (2007).
E. Betzig et al., Imaging intracellular fluorescent proteins at nanometer resolution, Science, 313, p. 1642-1645 (2006).
N. de. Jonge et al., Flow Cell for Electron Microscopy Imaging of Specimen in Liquid or Gas, p. 1-19, USA (2006).
E. A. Ring et al., Microfluidic system for transmission electron microscopy, Microscopy and Microanalysis, 16, p. 622-629 (2010).
N. de Jonge et al., Electron microscopy of whole cells in liquid with nanometer resolution, Proc. Natl. Acad. Sci., 106 (7), p. 2159-2164 (2009).

(Continued)

*Primary Examiner* — Sath V Perungavoor
*Assistant Examiner* — Jeffery Williams
(74) *Attorney, Agent, or Firm* — Locke Lord LLP; Tim Tingkang Xia, Esq.

(57) ABSTRACT

In one aspect, the present invention relates to a microfluidic chamber. In one embodiment, the microfluidic chamber has a first sub-chamber and at least one second sub-chamber. The first sub-chamber has a first window and a second window. Both the first window and the second window are transparent to electrons of certain energies. The second window is positioned substantially parallel and opposite to the first window defining a first volume therebetween. The first window and the second window are separated by a distance that is sufficiently small such that an electron beam that enters from the first window can propagate through the first sub-chamber and exit from the second window. The at least one second sub-chamber is in fluid communication with the first sub-chamber and has a second volume that is greater than the first volume of the first sub-chamber.

5 Claims, 18 Drawing Sheets

(56) References Cited

PUBLICATIONS

N. de Jonge et al., Three-dimensional scanning transmission electron microscopy of biological specimens, Microsc. Microanal., 16 (1), p. 54-63 (2010).

M. F. Hohmann-Marriott et al., Nanoscale 3D cellular imaging by axial scanning transmission electron tomography, Nat. Methods, 6 (10), p. 729-731 (2009).

O. H. Kwon et al., 4D electron tomography, Science, 328 (5986), p. 1668-1673 (2010).

Ring, E.A. et al., Silicon nitride windows for electron microscopy of whole cells, J. of Microscopy, 243, p. 273-283 (2011).

Niels de Jonge et al., Nanometer-resolution electron microscopy through micrometers-thick, Ultramicroscopy, 110, p. 1114-1119 (2010).

* cited by examiner

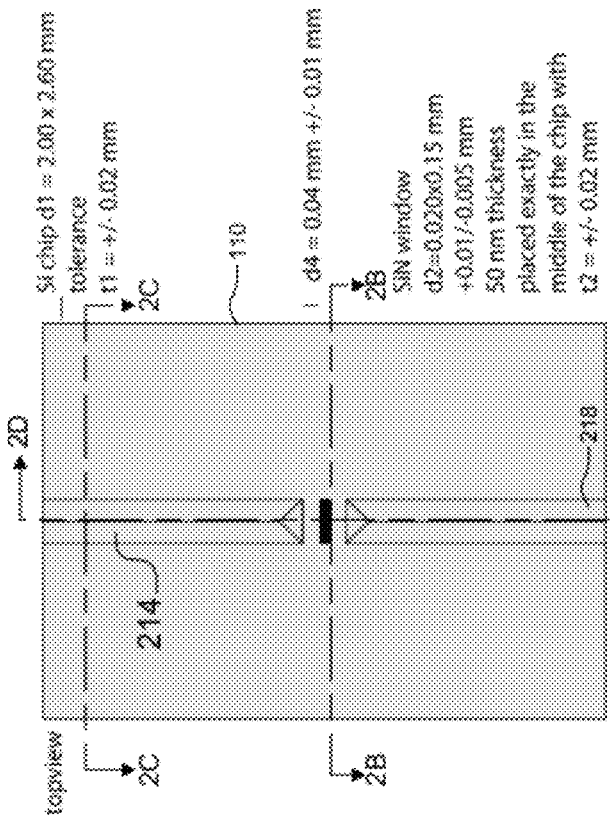
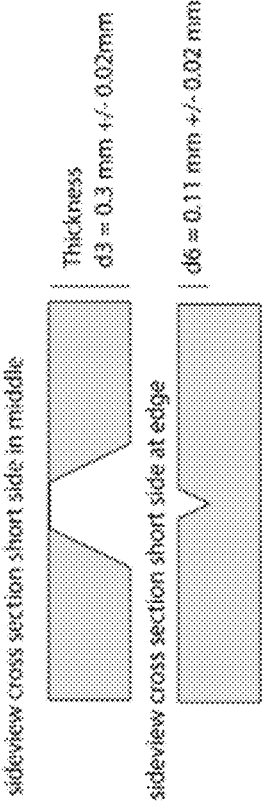
FIG. 2A
FIG. 2B
FIG. 2C
FIG. 2D

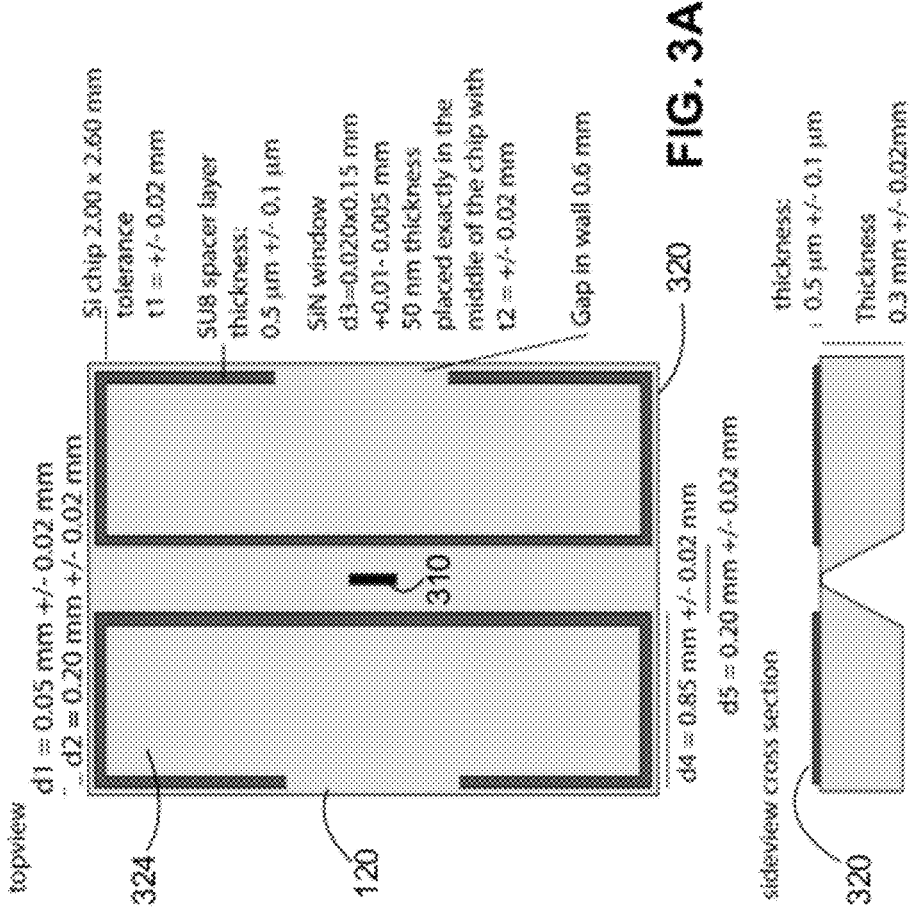

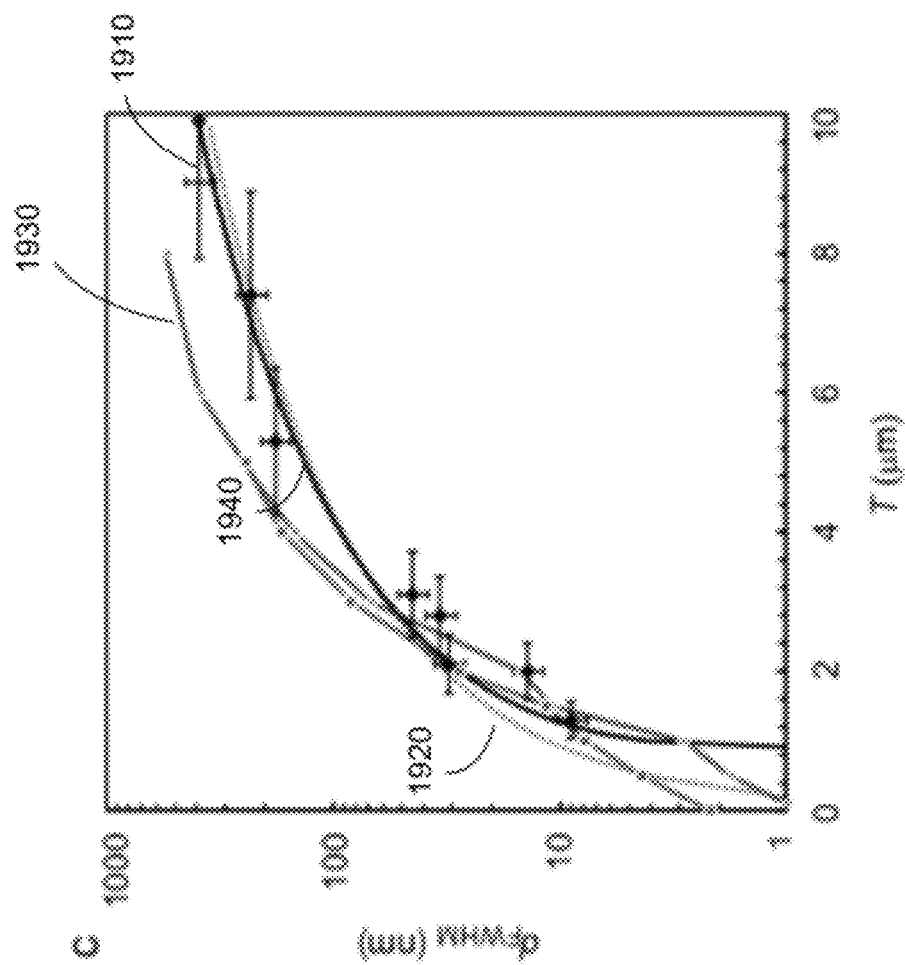
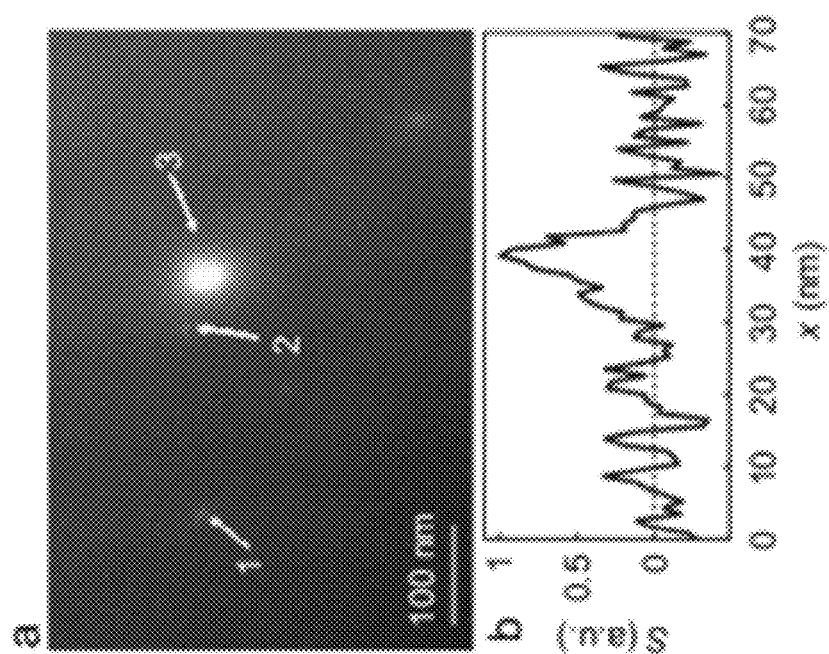
FIG. 18

TRANSMISSION ELECTRON MICROSCOPY FOR IMAGING LIVE CELLS

CROSS-REFERENCE TO RELATED PATENT APPLICATION

This application claims the benefit of U.S. Provisional Application No. 61/414,603, entitled "Transmission Electron Microscopy for Imaging Live Cells", filed on Nov. 17, 2010. The disclosure of the above application is incorporated herein by reference in its entirety.

Some references, which may include patents, patent applications and various publications, are cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [5] represents the 5the reference cited in the reference list, namely, E. A. Ring and N. de Jonge, "Microfluidic system for transmission electron microscopy," Microscopy and Microanalysis 16, 622-629 (2010).

FIELD OF THE INVENTION

The present disclosure relates generally to transmission electron microscopy, more particularly to transmission electron microscopy for imaging cells in their native liquid environment using a microfluidic chamber with electron transparent windows.

BACKGROUND

Liquid-phase processes are important over a wide range of areas in science and technology, including biological activity in cells, biomineralization, the low-cost synthesis of nanoparticles and electrochemical reactions for energy storage. Electron microscopy opens a unique window into structures and processes in the liquid phase, as it provides a combination of temporal and spatial resolution that is not achievable with other techniques. Transmission electron microscopy (TEM) of samples in liquid has a history stretching back as far as the earliest electron microscopes [A1]. But, over the past decade, electron microscopy of liquid samples has experienced a surge of interest, generated by advances in thin-film [A2] and microchip technology [A3]. Recent applications have included the imaging of labeled structures within whole cells [A4], electrochemical reactions [A3, A5] and solution-phase nanoparticle growth [A6].

For example, to develop new therapeutics, an important prerequisite is knowledge about the functioning of molecules inside cells, such as proteins and DNAs, and to learn about the interactions of cells with other organisms, such as viruses. Time-resolved confocal microscopy aims to image protein distributions and functions in living cells [1], leading to conclusions about the functioning of proteins inside live cells. However, light microscopy has a diffraction limited spatial resolution of at most 200 nm, such that processes cannot be resolved on a molecular level. Several techniques exist providing higher spatial resolution. Examples are stimulated emission depletion (STED) [2] and photoactivated localization microscopy (PALM) [3]. But those techniques still have a limited resolution on live cells and require special fluorescent labels.

Therefore, a heretofore unaddressed need exists in the art to address the aforementioned deficiencies and inadequacies.

SUMMARY OF THE INVENTION

In one aspect, the present disclosure relates to a microfluidic chamber. In one embodiment, the microfluidic chamber has a first sub-chamber and at least one second sub-chamber. The first sub-chamber has a first window and a second window. Both the first window and the second window are transparent to electrons of certain energies. The second window is positioned substantially parallel and opposite to the first window defining a first volume therebetween. The first window and the second window are separated by a distance that is sufficiently small such that an electron beam that enters from the first window can propagate through the first sub-chamber and exit from the second window. The at least one second sub-chamber is in fluid communication with the first sub-chamber and has a second volume that is greater than the first volume of the first sub-chamber.

In one embodiment, the second volume of the at least one second sub-chamber is sufficiently large for at least one living cell to be placed therein.

In one embodiment, the distance between the first window and the second window is smaller than about 10 microns, preferably smaller than about 1 micron.

In another embodiment, the first sub-chamber and the at least one second sub-chamber are formed between two microchips separated by a spacer.

In yet another embodiment, each of the two microchips is made of silicon.

In a further embodiment, each of the first window and the second window is made of silicon nitride.

In another aspect, the present disclosure relates to a method of imaging a cell in its native liquid environment. In one embodiment, the method includes the steps of: (a) placing the cell in a microfluidic chamber formed between two microchips separated by a spacer as set forth above, wherein a larger portion of the cell occupies the at least one second sub-chamber and a smaller portion of the cell occupies the first sub-chamber, (b) introducing the microfluidic chamber with the cell into a transmission electron microscope (TEM) such that an electron beam can enter the microfluidic chamber through the first window and exit the microfluidic chamber through the second window, (c) exposing the cell to an electron beam with an electron dosage, and (d) recording an image of the cell formed by the electron beam. The electron dosage is sufficiently low such that the electron beam does not cause damage to the cell.

In one embodiment, the microfluidic chamber is vacuum sealed such that there is no fluid communication between the microfluidic chamber and a vacuum in the TEM.

In one embodiment, the microfluidic chamber is in fluid communication with an external flow system. The external flow system includes means for exchanging fluid with the microfluidic chamber. In one embodiment, the external flow system includes means for providing nutrients to the cell in the microfluidic chamber. In another embodiment, the external flow system includes means for injecting chemicals into the microfluidic chamber. In yet another embodiment, the external flow system includes means for maintaining a chemical gradient in the microfluidic chamber. In a further embodiment, the external flow system includes means for controlling the temperature of the cell. The controlling means may include a thermocouple, a resistive heating wire, a thermoelectric heating element, or a combination thereof.

In one embodiment, the method further includes the step of, prior to the exposing step, introducing a plurality of label molecules into the cell for protein identification, by using one of the following methods or a combination thereof: i) endocytosis; ii) direct uptake through the cell membrane; iii) microinjection; iv) modification of a DNA of the cell to express proteins enclosing metal atoms; and v) incubation with a ligand connected to a label for specific binding to a certain receptor, or other molecule.

In one embodiment, the TEM is operated in a phase contrast mode or a scatter contrast mode.

In one embodiment, the TEM is operated in a scanning mode and contrast therefore. In one embodiment, the method further includes the step of, prior to the exposing step, introducing a plurality of high-Z atoms into the cell. In one embodiment, the plurality of high-Z atoms comprises gold atoms. In another embodiment the plurality of high-Z atoms comprises the constituents of a fluorescent quantum dot.

In one embodiment, the method further includes the steps of, at a time interval after the recording step: (a) exposing the cell a second electron beam with a second electron dosage, and (b) recording a second image of the cell formed by the second electron beam, thereby obtaining dynamic information about the cell. The second electron dosage is sufficiently low such that the second electron beam does not cause damage to the cell, thereby obtaining dynamic information about the cell.

In one embodiment, the method further includes the steps of, after the placing step and prior to the exposing step, or after the recording step: (a) exposing the cell to a light beam, and (b) recording a light microscopy image of the cell formed by the light beam. The light beam has an intensity that is sufficiently low such that the light beam does not cause damage to the cell.

In one embodiment, the cell is exposed to the electron beam for a time duration less than about 1 microsecond.

In one embodiment, the method further includes the steps of, after the recording step: (a) exposing the cell to a second electron beam for a second time duration that is less than about 1 microsecond, and (b) recording a second image of the cell formed by the second electron beam, thereby obtaining dynamic information about the cell while time time-scales are so short that possible radiation damage did not propagate by distances larger than the spatial resolution.

In another embodiment, the method further includes the step of, after the placing step and prior to the introducing step, freezing the cell, and the TEM is operated as a cryo-TEM.

In yet another embodiment, the method further includes the step of, after the placing step and prior to the introducing step, fixing the cell by injecting a chemical into the microfluidic chamber.

In a further embodiment, the placing step includes the steps of: (a) seeding the cell in the at least one second sub-chamber, and (b) inducing the cell to grow into the first sub-chamber using one of the following methods or a combination thereof: i) natural cell adherence, and ii) using chemicals.

In yet another aspect, the present disclosure relates to a microfluidic chamber. In one embodiment, the microfluidic chamber has a first microchip and a second microchip separated by a spacer. The first microchip has a substantially flat first surface and a first opening. The first opening is covered by a first window attached to the first surface. The first microchip further has at least one groove formed on the first surface extending from an edge thereof to an interior portion thereof adjacent to the first opening. The second microchip has a substantially flat second surface and a second opening. The second opening is covered by a second window attached to the second surface. The first microchip and the second microchip are positioned such that the first surface of the first microchip faces the second surface of the second microchip, and the first opening in the first microchip overlaps the second opening in the second microchip in an area. The overlap area defines a first sub-chamber with a first volume. The at least one groove formed on the first surface of the first microchip and a corresponding portion of the second surface of the second microchip define at least one second sub-chamber with a second volume. The at least one second sub-chamber is in fluid communication with the first sub-chamber. The second volume of the at least one second sub-chamber is greater than the first volume of the first sub-chamber. Each of the first window and the second window is transparent to electrons of certain energies. The spacer has a thickness that is sufficiently small such that an electron beam that enters from the first window can propagate through the first sub-chamber and exit from the second window.

In one embodiment, the second volume of the at least one second sub-chamber is sufficiently large for at least one living cell to be placed therein.

In one embodiment, the thickness of the spacer is less than about 10 microns, preferably less than about 1 micron. The at least one groove formed on the first surface of the first microchip has a depth greater than about 50 microns and a width greater than about 50 microns.

In another embodiment, each of the first window and the second window is made of silicon nitride and has a thickness of about 50 nm.

In yet another embodiment, each of the first microchip and the second microchip is made of silicon.

In a further embodiment, each of the first microchip and the second microchip is made of glass, carbon, metal, or a combination thereof.

BRIEF DESCRIPTION OF THE DRAWINGS

FIG. 2A shows schematically the structure of the first microchip used to form the microfluidic chamber shown in FIG. 1, according to one embodiment of the present disclosure.

FIG. 2B is a cross section view along line 2B of FIG. 2A.
FIG. 2C is a cross section view along line 2C of FIG. 2A.
FIG. 2D is a cross section view along line 2D of FIG. 2A.

FIG. 3 shows schematically the structure of the second microchip used to form the microfluidic chamber shown in FIG. 1, according to one embodiment of the present disclosure [11].

FIG. 18 shows STEM imaging of gold nanoparticles below a water layer [D].

DETAILED DESCRIPTION

Figure 1:
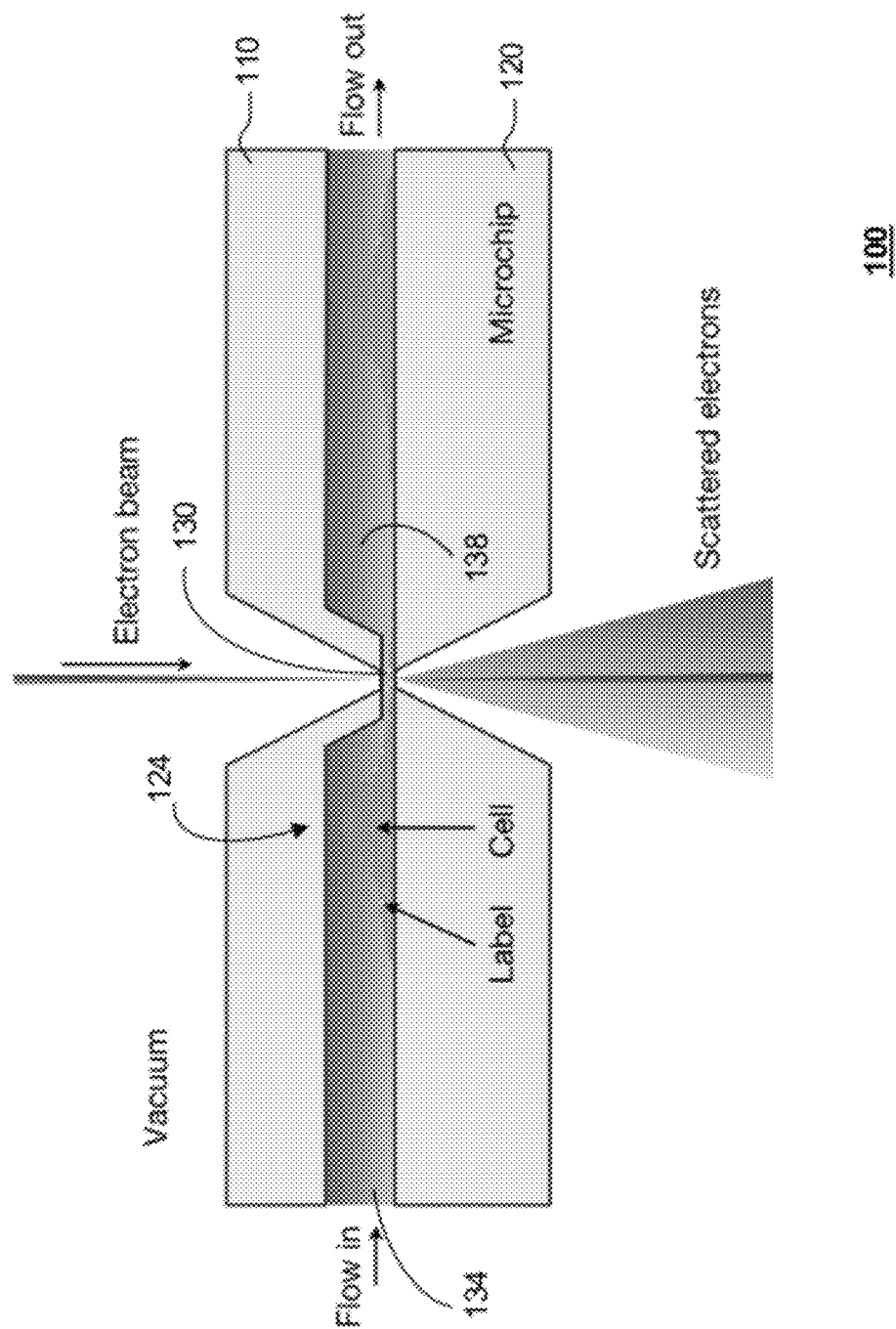
FIG. 1 illustrates the principle of a live cell transmission electron microscope (TEM) system according to one embodiment of the present disclosure.

The present disclosure is more particularly described in the following examples that are intended as illustrative only since numerous modifications and variations therein will be apparent to those skilled in the art. Various embodiments of the disclosure are now described in detail. Referring to the drawings, like numbers indicate like parts throughout the views. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which has no influence on the scope of the disclosure. Additionally, some terms used in this specification are more specifically defined below.

The terms used in this specification generally have their ordinary meanings in the art, within the context of the disclosure, and in the specific context where each term is used.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the terms "comprising," "including," "having," "containing," "involving," and the like are to be understood to be open-ended, i.e., to mean including but not limited to.

OVERVIEW

Electron microscopy (EM) has been a key provider of the existing knowledge about subcellular and molecular structures in cells [C1]. Without EM it would not have been possible to integrate biochemical and atomic-scale structural information, obtained, for instance, from x-ray crystallography and nuclear magnetic resonance studies, into a realistic cellular framework [C2]. Scientists have hoped since the early days of electron microscopy to achieve better resolution than the diffraction-limited resolution of light microscopy for imaging live eukaryotic cells, to gain insights into the native intracellular ultrastructure [C3]. Despite various attempts, the spatial resolution obtained with EM on pristine cellular samples in aqueous solutions was not better than that achievable with light microscopy [C4, 5]. Nanometer resolution is achieved with cryo-EM [C6, 7] and x-ray microscopy [C8, 9], but both require frozen samples to preserve the cellular ultrastructure. Consequently, the imaged cells are not in their native liquid environment, nor in a living state. Nanoscale scanning probe microscopy is limited to the imaging of cellular surfaces [C10, C11]. Superresolution light microscopy [C3, C12] reaches a subdiffraction resolution of <50 nm in live cells, but only on fluorescent labels attached to specific sets of proteins, and not on the native cellular ultrastructure. It is thus not possible at the present time to study the ultrastructure of pristine eukaryotic cells.

Some of the following text in the Overview was in part published in a review article of electron microscopy of liquid specimens [A]. The three commonly used types of electron microscope each generate images via different contrast mechanisms [A7-A9]. In TEM, a stationary, spread electron beam with energy between ~60 and 300 keV irradiates a sample that is thinner (often much thinner) than 0.5 μm. The sample modifies the phase and amplitude of the transmitted electrons, so that the resulting image contains information about the sample. In scanning TEM (STEM), the image is recorded by scanning a focused beam over the sample and detecting transmitted electrons pixel by pixel. Scanning electron microscopy (SEM) scans a focused beam, typically with energy between ~500 eV and 30 keV, over the surface of a (bulk) sample, collecting backscattered or secondary electrons pixel by pixel. All electron microscopes require a vacuum, both to allow operation of the electron source and to minimize scattering other than from the sample. Samples must therefore be stable under vacuum, and so are traditionally prepared in the solid state.

However, since the invention of the electron microscope, a goal has been to image liquid samples as easily as with a light microscope, but with much higher spatial resolution [A1, A10]. Liquids that have low vapour pressure [A5] or that are already encapsulated by another material [A11] can be examined without special precautions. But, the majority of liquid samples, including those involving water, require other strategies. the earliest system [A1] consisted of an open environmental chamber in the sample region of a TEM. Using differential pumping, this chamber could be kept at a pressure up to 0.2 bar to create a wet sample environment containing both liquid and vapour, while the rest of the microscope remained at low pressure [A12].

Open environmental chambers can be used in situ TEMs for both gas- and liquid-phase reactions [A13, A14]. However, it is difficult to control the liquid thickness accurately in an open environmental chamber, making it challenging to obtain liquid films thinner than ~1 μm, as required for nanometer-scale resolution in TEM. Instead, it proved more practical to develop the environmental chamber for imaging liquids in SEM [A15], where there is of course no requirement for a thin sample. Environmental SEM, or ESEM, is used to image the surface of samples in a vapour environment, achieving a spatial resolution in the nanometer range [A16, A17].

The open environmental chamber is not suitable if, for example, the sample must be embedded in a liquid layer of controlled thickness, or if the experiment requires a flowing liquid. The problem then becomes that of designing a thin yet stable liquid layer. This is achieved by means of a hermetically sealed enclosure, or 'liquid cell', that constrains the liquid into a layer less than a few micrometers thick. Various systems has been developed that used electron-transparent membranes to create such closed liquid cells [A12, A18]. However, the liquid layers were still not particularly thin, and the spatial resolution achieved[12] was often not much better than what was available, with much less effort, through light microscopy.

Over the past decade, developments in thin-film technology, microfabrication and imaging have brought new life to the use of liquid cells [A3]. Thin carbon foils [A19, A20] and graphene sheets [A21] can be used as membranes. Thin (20-100 nm) SiN films supported on silicon microchips can also be used as membranes, as they are easily manufactured, homogeneous in composition and thickness, and make robust windows for liquid cells with designs. Standard silicon processing techniques allow electrodes to be integrated onto the microchips [A3, A22], increasing the range of experiments possible. Careful design has simplified assembly [A22-A24], and can even permit the use of flowing liquids [A4, A25], as will be described below. Finally, imaging can be optimized, using STEM to obtain nanometer-scale resolution even through several micrometers of water [A4, A26].

These advances have paved the way for liquid TEM and STEM to make significant impact in biological and materials science. Of course, experimental difficulties still remain. One issue particular to experiments involving liquid cells is balancing window size, liquid thickness and window thickness with field of view and image resolution. Resolution improves as the liquid layer and windows become thinner, as will be described below. However, thin windows bow under vacuum, increasing the liquid thickness in the centre of the window [A27]. To optimize resolution, one may consider connecting the windows by pillars [A28-A30], or using wafer bonding [A22] to reduce window separation. The window thickness itself may limit the resolution; this can sometimes be overcome by using graphene sheets to enclose the sample [A21]. The formation of bubbles in the liquid layer [A27, A31] also causes problems. Uncontrolled bubble formation may be alleviated by flowing the liquid25, although the reduced liquid thickness at a bubble actually improves resolution [A27, A32].

Thin window systems are useful in SEM as well as in TEM and STEM. A closed liquid cell, similar to those used in TEM, allows transmitted signals in the SEM to be collected [A22]. Alternatively, a 'capsule' with a single window can enable SEM of samples fully immersed in liquid by collecting a backscattered signal through the window [A2]. Backscatter imaging through a window is advantageous in that it allows SEM to be combined with light microscopy [A33]. A liquid sample in a dish with an integrated window can be imaged with light microscopy from the liquid side or SEM from the window side [A33]. This approach allows correlative microscopy as well as possibilities such as excitation of fluorescent materials with the electron beam at nanometer localization [A34].

It may at first appear counterintuitive, but excellent spatial resolution is possible in liquid layers, down to a few nanometers even through several micrometers of liquid [A4, A26], or atomic resolution for very thin water layers [A35]. Temporal resolution can also be good, so dynamic processes can be observed [A3, A6, A35]. However, electron beam effects provide a practical limitation.

To achieve a resolution sufficient for imaging individual molecules inside cells such as proteins and DNAs, a technique is to use a microfluidic flow cell with electron transparent windows for imaging of cells in their native liquid environment with a scanning transmission electron microscope (TEM) [4, 5]. Experimental results have demonstrated the imaging of proteins labeled with gold nanoparticles on fixed eukaryotic cells with 4 nanometer resolution in a liquid layer with a thickness of about 7 microns [6]. The present disclosure, in one or more aspects, relates to TEM or scanning transmission electron microcopy (STEM) for imaging live cells in liquid. The live cell TEM system comprises a microfluidic chamber with electron transparent windows. The chamber is placed in a vacuum chamber inside the electron microscope while the liquid interior connected to the outside of the microscope is sealed from the vacuum by the windows. Live cells are placed in the microfluidic chamber. In one embodiment, the microfluidic chamber contains three sub-chambers, two large ones fitting most of the cell body, and a thin one, approximately one micron thick, fitting the thinner regions of cells. The electron transparent windows are located at the thin region. An electron beam propagates through the thin part of the microfluidic chamber. A high contrast is obtained in both TEM and STEM on biological materials. In one aspect, the present disclosure relates to a method of imaging cells in liquid, taking into account the damaging effects of electron beam radiation. In another aspect, the present disclosure relates to a method to enhance the visibility of individual molecules. In yet another aspect, the present disclosure relates to a method to discriminate different types of molecules. In a further aspect, the present disclosure relates to a method of changing the chemical composition of the liquid surrounding the cell. Several other methods are included as well. In various embodiments, the present disclosure presents a novel approach to molecular-level imaging of intracellular processes with a spatial resolution that is two orders of magnitude higher than that of confocal laser microscopy and for the same imaging speed (microseconds per pixel). This approached can be applied to various types of cells including prokaryotic and eukaryotic cells, and other materials, such as protein complexes or viruses.

Further to use the full potential of electron microscopy of liquids it is important to understand the ultimate performance possible, the major experimental limitations, and how these compare with other techniques.

The Resolution in TEM.

For TEM, high resolution for an object within a liquid can be achieved when the object is at the electron beam exit side of the sample. To a first approximation, the window material itself can be considered transparent for typical beam energies. Instead, the resolution-limiting factor is chromatic aberration caused by inelastic scattering of electrons by the liquid [A31]. The full-width at half-maximum of the energy distribution $\Delta E$ of transmitted electrons follows from calculations of the inelastic electron scattering cross-section and is given by the following equation [A8]:

$$\Delta E = \frac{N_A e^4 Z \rho T}{2\pi \varepsilon_0^2 W m_0^2 v^2} \quad (EA1)$$

Here, $N_A$ is Avogadro's number, e is the elementary charge, Z the atomic number, p the density and T the thickness of the liquid layer, $\varepsilon_0$ the permittivity of space, W the atomic weight, $m_0$ the mass and v the velocity of the electrons. This energy broadening affects the resolution of the image because of the chromatic aberration of the objective lens. The image resolution $d_c$ can be approximated by[8]:

$$d_z = \alpha C_c \frac{\Delta E}{2E} \quad (EA2)$$

where α is the objective semi-angle, $C_c$ is the chromatic aberration coefficient and E is the beam energy. For water, where[26,66] Z=4.7, one can combine equations (1) and (2) into the following expression for the resolution:

$$d_{TEM} = 6 \times 10^{12} \frac{\alpha C_c T}{E^2} \qquad (EA3)$$

with E in eV (using p in g m$^{-3}$ in equation (2)). For typical values, α=10 mrad, $C_c$=2 mm, E=200 keV and T=1 μm, one can obtain $d_{TEM}$=4 nm, consistent with experimental findings [A31]. (At 300 keV, a higher $d_{TEM}$ of ~1 nm has been obtained in organic solvent [A6].)

Equation (EA3) gives the best possible resolution; worse resolution will be seen for objects positioned further from the exit side of the sample, as elastic scattering of electrons in the liquid between the focal plane and the window will broaden the beam [A26, A67-A70]. For example, a TEM image of a particle at the top of a 1-μm-thick water layer would have a resolution of only ~12 nm. However, it is worth noting that diffraction techniques can be used in TEM when the sample in liquid contains repetitive units [A12], and this may allow higher resolution information to be obtained.

The resolution in STEM. For STEM, high resolution for an object within a liquid can be achieved when the object is at the entrance side of the sample [A4, A71]. The image is formed pixel by pixel by scanning a focused electron probe over the sample, and contrast is commonly obtained by using an annular dark-field detector to collect electrons that are elastically scattered out of the primary electron beam. Unlike TEM, nanometer resolution has been obtained in STEM, even for micrometers-thick samples [A26, A67, A72, A73]. The fraction $N/N_0$ of electrons detected, that is, scattered by an angle larger than the opening semi-angle of the detector β, is [A8]:

$$\frac{N}{N_0} = 1 - \exp\left(-\frac{T}{l}\right), l = \frac{W}{\sigma(\beta)\rho N_A} \qquad (EA4)$$

Here, l is the mean free path length for elastic scattering and σ(β) is the partial cross section for elastic scattering. The elastic scattering, and hence the image contrast in STEM, is highly sensitive [A74, A75] to W, p and Z (so-called Z-contrast) via σ(β), making STEM extremely effective for imaging heavy nanoparticles in a light liquid. For example [A4, A26], with β=70 mrad and E=200 keV, one can obtain $l_{gold}$=73 nm and $l_{water}$=10.5 μm. The STEM resolution in a liquid sample can be thought of as the diameter of the smallest nanoparticle visible above the background noise [A4, A26]:

$$d_{STEM} = \zeta l_{nanoparticle} \sqrt{\frac{T}{N_0 l_{liquid}}} \qquad (EA5)$$

Figure 6:
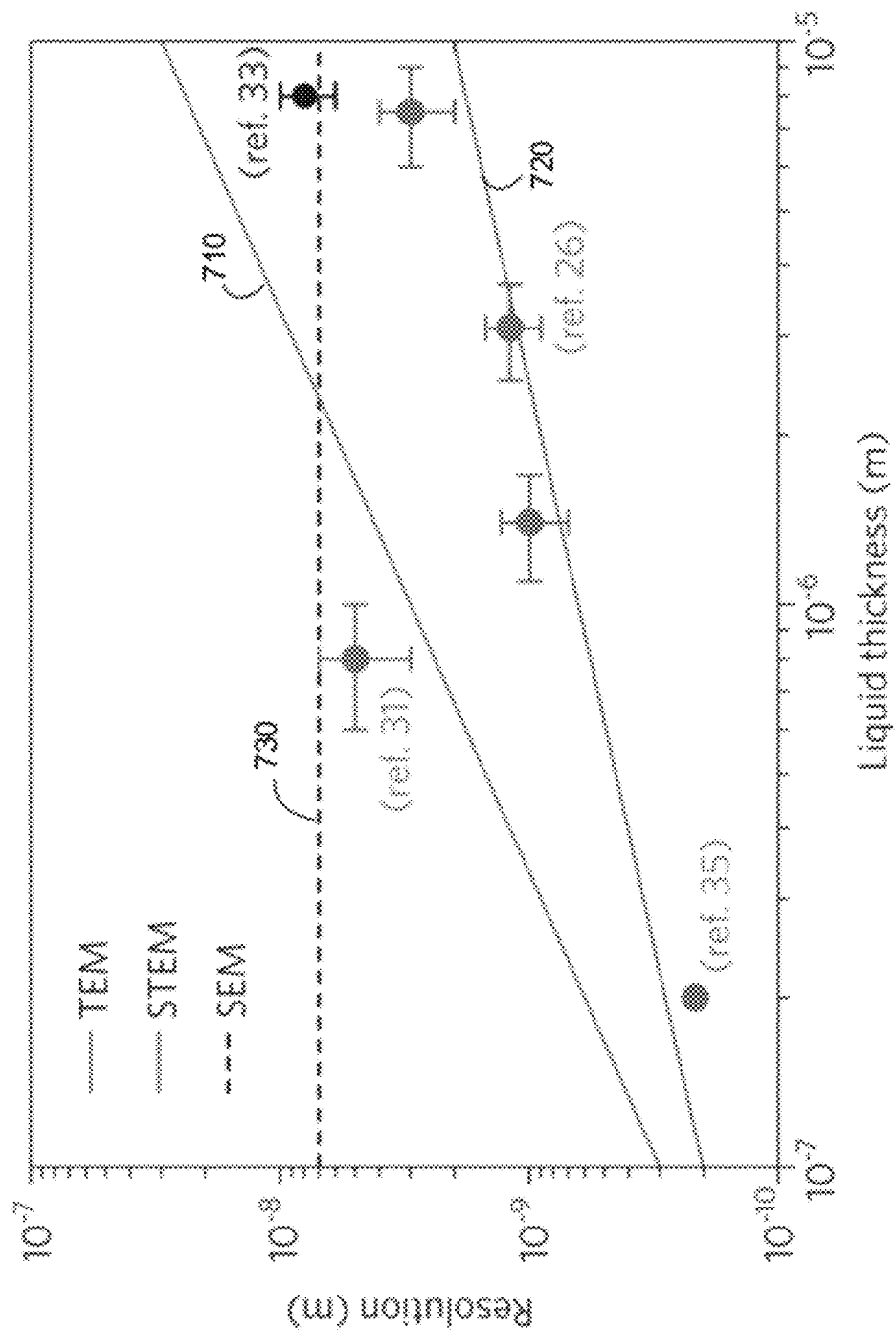
FIG. 6 shows resolution of different forms of electron microscopy in liquid [A].

According to this equation, a 1.4-nm-diameter Au nanoparticle can be resolved on a water layer [A26] of T=5 μm, using a probe current of 0.5 nA and a pixel dwell time of 10 μs. FIG. 6 includes the STEM resolution as function of T for these microscope settings, matching experimental data [A26, A35]. More specifically, FIG. 6 shows resolution of different forms of electron microscopy in liquid. Theoretical maximal resolution versus water thickness for TEM 710, STEM 720 and SEM 730. The resolution was calculated for typical TEM and STEM instrument parameters at 200 keV beam energy (see text), and for the imaging of Au nanoparticles at the bottom of a layer of water for TEM, and at the top of the layer for STEM. The resolution obtained in SEM just below the liquid-enclosing membrane does not depend on the liquid thickness Experimental data points are shown for Au nanoparticles in TEM A31, STEM A26 and SEM with a 30-nm-thick SiN window A33, and for PbS nanoparticles in water imaged with STEM A35. The error bars represent experimental errors. For nanoparticles positioned deeper in the liquid, imaging takes place with a blurred probe, but a resolution better than 10 nm is still achieved in the top 1 μm layer of the liquid [A26].

The resolution in SEM. In SEM of enclosed liquid samples, contrast is generated via backscattering of electrons in the sample after passing through the window A8. However, because of the low beam energy used in SEM compared with TEM, the electron probe is already considerably broadened by the time it reaches the liquid. The resolution follows from the beam broadening equation [A76]:

$$d_{SEM} \cong 6.1 \times 10^3 T^{3/2} \frac{Z}{E} \left(\frac{\rho}{W}\right)^{1/2} \qquad (EA6)$$

where T, Z, p and W are parameters of the membrane. Note that for SEM the beam broadening is calculated on the basis of the diameter containing 90% of the current [A76], accounting for the large interaction volume of the electron beam with the sample, whereas smaller measures are used for (S)TEM [A8, A26, A67]. For a typical SiN window 30 nm thick [A33], the beam size, and hence best SEM resolution, calculated from equation (6) is 7 nm at 20 keV. This is consistent with experimental findings [A33] of ~8 nm.

The resolution does not depend on the total liquid thickness, of course, but it does decrease rapidly for nanoparticles deeper in the liquid. For example, at a depth of 100 nm, the resolution is already reduced to 20 nm. SEM should thus be used to study structures in close proximity to the window. the window thickness is also of crucial importance. A system using a ~150 nm thick plastic window provided maximal ~20 nm resolution for Au nanoparticles [A2, A77]. For ESEM, the resolution can approach that of SEM in vacuum, but as the liquid layer on the sample surface increases in thickness, the resolution also drops dramatically.

Radiation Damage.

Electron beam-sample interactions are a key factor in any electron microscopy experiment. For liquid samples, a rigorous interpretation of results certainly requires an understanding of beam effects. This can be complicated by the variety of possible interactions and the need for quantitative models for beam-liquid interactions.

The materials science investigations described above have considered a variety of thermal and non-thermal beam effects. Beam heating is calculated [A29] to result in only a small temperature rise (a few degrees or less) because of the good thermal conductivity of the thick liquid cell samples. This may nevertheless alter diffusion and reaction rates through convection, while even a slight temperature rise alters electrochemical kinetics. Non-thermal effects may be more important and are more complicated, depending on the system under study. High-energy electrons in water produce relatively long-lived species such as OH radicals and hydrated electrons [A78, A79]. These species may be key to electron-beam-induced formation of nanoparticles from solvated species [A6, A80]. Solution chemistry is then important—for example, charged species in solution may quench the radicals and reduce their reactivity [A78]—but substrate chemistry is also important, as reactive species can also be generated from beam-substrate interactions [A65]. The charged species may also influence the currents measured in an electrochemical experiment. Clearly, experiments under different conditions of accelerating voltage or beam intensity are necessary to evaluate the effect of the beam on any liquid-phase phenomenon under study.

Organic samples are known to be strongly affected by relatively small electron doses. For pristine biological material, structural damage starts to occur at the subnanometer scale [A81] at $\sim 10^2$ electrons per $nm^2$. This threshold dose is a factor of ten lower than the dose limit for cryo TEM [A38]. Fortunately, the dose typically scales quadratically with the resolution [A71], and in many cases the experiment can be designed such that a useful resolution can still be obtained within the limit of radiation damage. Recording, for instance, a 1024×1024 pixel TEM image of a 1-μm-thick sample with 20 nm resolution would require a 10 nm pixel size and an integration time of ~0.2 s for a typical beam current of 10 nA. The resulting dose of $1.2 \times 10^2$ electrons per $nm^2$ is within the limit of radiation damage. Staying below the threshold dose permitted STEM imaging of yeast cells with a resolution [A49] of ~30 nm, and TEM recording of protein crystal diffraction patterns containing subnanometer information [A12]. Above the threshold, a better image resolution (a few nanometers) may still be possible, as the overall structure will remain in place at least for some time after damage at the subnanometer scale occurs (for example, by breaking of chemical bonds). If a much higher dose is required, the sample would have to be stabilized by fixation, allowing doses 4 of $\sim 7 \times 10^4$ electrons per $nm^2$. Another approach to overcome radiation damage is to use high contrast nanoparticle labels in combination with STEM imaging. Equations (1)-(6) suggest that 4 nm resolution on a Au nanoparticle in 1 μm of water requires only $1.2 \times 10^2$ electrons per $nm^2$. A larger dose is probably allowed as some structural damage can be tolerated before the locations of the labels change too much. Compared with TEM and STEM, SEM is unfavourable in terms of radiation dose, because the entire beam energy is typically deposited in the sample.

Temporal resolution. Typical image acquisition rates (time resolution) are over 10 frames per second for TEM, whereas the dwell time needed to form each pixel in a STEM or SEM image is typically in the range of 1-60 μs. Although this makes electron microscopy of liquids excellent for studying time-dependent phenomena, as described above, it is worth noting that Brownian motion may limit the achievable image resolution, particularly when imaging live cells or other structures not fixed to the walls of the liquid chamber. Membrane proteins, for example, exhibit diffusion constants [A82] as high as 1 $\mu m^2$ $s^{-1}$ under physiological conditions, which may lead to movement of several nanometers within the typical pixel time of STEM. The achievable spatial resolution will thus be influenced by parameters such as viscosity, diffusion constants, image acquisition time and also the distance from the window [A83].

Even given the limitations on resolution due to Brownian motion and beam effects, the combination of spatial and temporal resolution of electron microscopy in liquids is unique. Standard light microscopy is limited by diffraction to a spatial resolution [A84] of ~200 nm. Super-resolution light microscopy [A47, A85, A86] achieves 20-30 nm resolution, but requires dedicated fluorescent labels, and is limited in temporal resolution for the higher spatial resolution. X-ray microscopy has a resolution in the tens of nanometers range [A87, A88]. Scanning probe microscopy exhibits nanometer resolution in liquids, but videorate image acquisition is optimized for flat surfaces (for example, refs A89-A92). Any given problem is best addressed by multiple techniques; liquid cell electron microscopy should be able to provide key information for many scientific questions.

Electron microscopy in liquids offers a combination of nanoscale spatial resolution and subsecond temporal resolution that suggests significant potential in numerous scientific and technological areas. Improvements in experimental capabilities and advances in the quantification of results can lead to application in a wider future range of scientific problems.

In terms of experimental advances, the recent improvements in aberration correction that are revolutionizing the TEM and STEM community [A75] can also impact electron microscopy in liquids [A35]. Equation (EA3) showed that the resolution of TEM in liquids is limited by chromatic aberration, in other words, by imperfect focusing of electrons that have different energies. Preventing electrons from contributing to the image if they have lost more than a certain amount of energy would therefore improve the resolution. Such energy filtering allows [A93], in principle, subnanometer spatial resolution for liquid layers with a thickness well above 0.5 μm for TEM. However, energy filtering also increases the required dose for imaging. Instead, correction of the chromatic aberration in the electron lenses [A94] should improve the resolution in a more dose-efficient way. Temporal resolution should also see a significant improvement. Imaging with speeds of several tens of milliseconds per frame is possible with modern detectors, and in addition, ultrafast TEM has emerged, which uses pulses of electrons triggered by an incident laser beam [A95, A96]. The short imaging times require high beam currents to obtain sufficient signal-to-noise, giving rise to Coulomb interactions that reduce the effective brightness of the electron beam, and thus the achievable spatial resolution [A97]. The capability to image materials in liquid using pulses of electrons potentially opens up the interesting possibility of capturing native protein, cellular or nanomaterial configurations before radiation-induced effects have time to propagate through the structure, thus overcoming the limitation of radiation damage.

An important direction, especially for biological investigations, is the combination of light microscopy with electron microscopy. Radiation damage will probably prevent electron microscopy studies of processes in biological systems. However, these processes can be imaged with light microscopy, for example through phase contrast microscopy of the native cellular material or fluorescence microscopy of labeled proteins or other components in cells [A98]. At a certain time of interest, the sample can be transferred to the TEM, STEM[4] or SEM for nanoscale investigation of the biological structure itself or of nanoparticles attached to the biological material. The type of sample and required resolution will determine the choice of electron microscopy modality. The temporal correlation of light and electron microscopy is typically several minutes, as the sample holder has to be transferred from one microscope to the other [A49]. Integration of light microscopy with SEM [A33], or fluorescence microscopy with TEM [A99] or STEM, can allow temporal correlation within seconds.

Quantitative data acquisition is a key challenge for electron microscopy of liquids, in particular if one hopes to use the technique to understand the fine details of static structures and to test models for dynamic processes. In conventional electron microscopy, a broad body of literature examines the effect of microscope parameters on image characteristics, and the effect of the electron beam on traditional solid samples and solid-state processes [A8, A9, A71]. The same effort is now required for liquid samples. The equations above give guidance on the optimal parameters for imaging, but further experimental testing is required, especially regarding the improvements possible with aberration correction. Equally important is the need for a more rigorous understanding of beam-sample interactions for a variety of materials, so that guidelines can be developed for when and how imaging is likely to affect the results. Finally, for quantitative matching of data with models for dynamic events, such as particle growth and deposition, the liquid geometry and flow must be understood. Liquid movement, Brownian motion and diffusive phenomena in the restricted volume of an enclosed liquid cell form an interesting scientific topic of which understanding is required for developing quantitative models.

With these experimental advances, one can anticipate that electron microscopy of liquid samples will play an important role in solving a broad set of scientific problems. Electron microscopy of biological samples in microfluidic devices may serve the pressing need for microscopy of cells and other biological systems and materials in their native liquid state with a resolution of a few nanometers—the dimension of proteins. Membrane receptors on intact cells can be studied in liquid [A2, A4, A33] using labels with different size, shape and composition to tag different proteins. Labeling of intracellular proteins can be accomplished using emerging technologies [A100, A101]. The uptake of nanoparticles into the interior of cells can be studied with relevance for nanotoxicology [A48, A102, A 103]. Samples can be fixed after different time points to study processes involving multiple lipid and/or protein species [A4]. Alternatively, using the correlative techniques discussed above, cells can be kept alive in a microfluidicchamber, monitored with fluorescence microscopy and imaged at certain times with electron microscopy [A49]. With nanometer resolution and functionality similar to that of fluorescence microscopy, this approach will be significant for many fields of biological and biomedical research including virology, oncology, neuroscience and cell biology.

In materials science, electron microscopy of liquids is likely to play a central role in improving the understanding of reactions in energy materials, such as examination of failure modes of batteries during cycling [A104, A105], or to address new materials and microstructures for energy storage. Lithiation of anodes and formation of interfacial layers between electrolyte and electrodes are of particular relevance to commercial lithium-ion batteries, yet are difficult to study outside the liquid environment of the battery itself. Liquid cell electron microscopy is likely to make an impact in other areas as well, such as biomineralization with relevance for carbon dioxide sequestration, and in research on hydrated geological materials, such as clays, with applications in petroleum extraction and soil science. Complex nanoparticle arrays can be developed by directly visualizing self-assembly processes that are induced by external fields or by functionalization of the particles themselves. Controlled liquid mixing and application of heat, magnetic fields or other external stimuli will increase the range of processes that can be studied.

EXAMPLES

Aspects of the present teachings may be further understood in light of the following examples, which should not be construed as limiting the scope of the present teachings in any way.

Example 1

Microfluidic Chamber with Electron Transparent Windows

According to one embodiment of the present disclosure, live cells in liquid are enclosed in a microfluidic chamber shown schematically in FIG. 1. This enclosure is placed in a vacuum of a TEM. The bodies of the cells grow in the two larger sub-chambers, while thin regions of the cell grow into and through a thin sub-chamber. The electron beam propagates through the thin sub-chamber. The thickness of the thin sub-chamber can be adjusted to optimize for a particular experiment. For TEM imaging with phase contrast, or scatter contrast, it is desired to maintain the total sample thickness below one micron, which can be done by setting the thickness of the thin sub-chamber to this value. The TEM can also be operated in scanning mode, so called STEM. Specific high-Z labels can be used to recognize proteins or other molecules. Liquid is flown through the system.

One key component for live cell TEM is a microfluidic chamber. In one embodiment, the microfluidic chamber 124 comprises two silicon microchips 110, 120 spaced apart by a thin spacer layer 320, defining a smaller sub-chamber 130 and two larger sub-chambers 134, 138. FIG. 2 shows schematically the structure of the first microchip 110 used to form the microfluidic chamber 124 shown in FIG. 1, according to one embodiment of the present disclosure. The first microchip 110 has an ultra-thin and electron-transparent window 210 disposed in the middle of the first microchip 110. In one embodiment, the window 210 is made of silicon nitride. Two open channels 214, 218 are formed at each side of the window 210. These channels 214, 218 are large enough to fit the main body of at least one eukaryotic cell. The channels 214, 218 also enhance liquid flow when two microchips 110, 120 are placed together to form a microfluidic chamber 124. Liquid enters from one side of the first channel 214, passes through the first channel to the thin region 220 at the location of the window 210, then passes through the second channel 218 and leaves at the other side.

FIG. 3A shows schematically the structure of the second microchip 120 used to form the microfluidic chamber 124 shown in FIG. 1, according to one embodiment of the present disclosure. The second microchip 120 also has an ultra-thin and electron transparent window 310 disposed in the middle of the second microchip 120. In one embodiment, the window is made of silicon nitride. A thin spacer 320 is placed on a surface 324 of the second microchip 120 as shown in FIG. 3. Cells adhere and grow at the open surface over the microchip 120 and crossing the silicon nitride window 310. The first and second microchips 110, 120 are pressed together to form a microfluidic chamber as shown in FIG. 1. The spacer 320 sets the thickness of the thin sub-chamber 130. Liquid and debris such as cellular materials can flow away through the gaps in the spacer layer at the sides of the chips 110, 120 when the microfluidic chamber 124 is assembled. In one embodiment, the spacer layer 320 is made of SU8 and is shaped in a form of a wall instead of a thin film as shown in FIG. 3A, so as to minimize the influence of dust particles and cellular materials when the two microchips 110, 120 are pressed together.

In one embodiment, the microchips 110, 120 are formed from a double-sided polished silicon wafer of about 300 μm thickness. A thin layer of silicon nitride (about 50 nm thick) is provided on both sides of the wafer. Openings are made in this layer by means of photolithography and etching. The exposed silicon is then etched away in KOH. The etching occurs with an angle of about 54.74° along the crystal planes of the silicon and stops at the silicon nitride at the other side of the wafer, or at a crystal plane. The sides of the microchips 110, 120 are made with a precision better than 10 microns, such that the windows overlap 210, 310 when the two microchips 110, 120 are pressed together to form a microfluidic chamber 134, as needed for the propagation of the electron beam. In one embodiment, a spacer layer 20 made of SU8 material is formed on one of the microchips 110, 120 via photolithography.

When the microfluidic chamber 124 is assembled, the two silicon nitride windows 210, 310 overlap, leaving a viewing window of a square with sides of a length of about 20 microns, since the two silicon nitride windows 210, 310 are placed perpendicular with regard to their long side. This size was chosen as optimum between the largest possible viewing area and the smallest possible window size. The window size needs to be small in order to prevent bulging of the windows in the vacuum of the microscope, which should be less than a few tens of micrometers only, in order to provide a gap of about 0.5 micrometer. Other dimensions can be used. The silicon nitride windows may be thinner or thicker. The windows may have other sizes and shapes. A larger viewing area can be constructed by using a silicon nitride window containing a supporting structure, for example, thicker regions, to prevent bending. Other materials than silicon and silicon nitride can be used, for example, the microchips may be made of glass and the windows may be made of carbon.

Example 2

Figure 4:
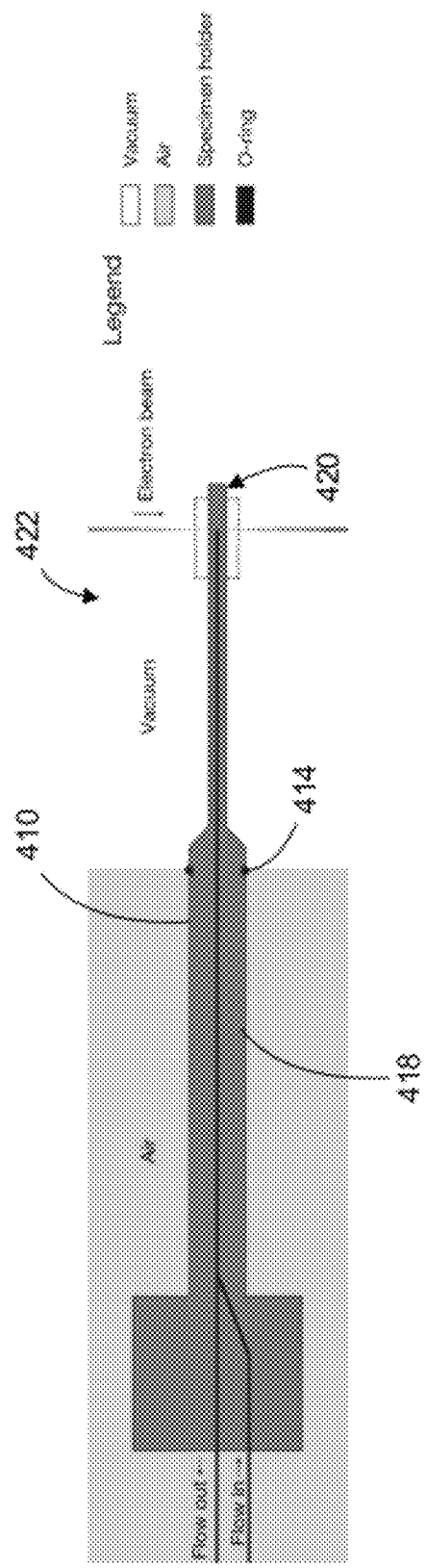
FIG. 4 shows schematically a liquid specimen holder used in conjunction with the microfluidic chamber for live cell TEM, according to one embodiment of the present disclosure.

Liquid Specimen Holder Used in Conjunction with a Microfluidic Chamber for Live Cell TEM The microfluidic chamber 134 is then placed in a vacuum of a transmission electron microscope using a specimen holder 410 for liquid flow. FIG. 4 shows schematically the specimen holder 410 according to one embodiment of the present disclosure. The specimen holder 410 is of the side-entry type. The specimen at the tip 420 (right end) is connected with liquid tubing to a liquid flow system outside the microscope. An O-ring 414 on the shaft 418 separates the outside air from the vacuum 422 inside the microscope.

Figure 5:
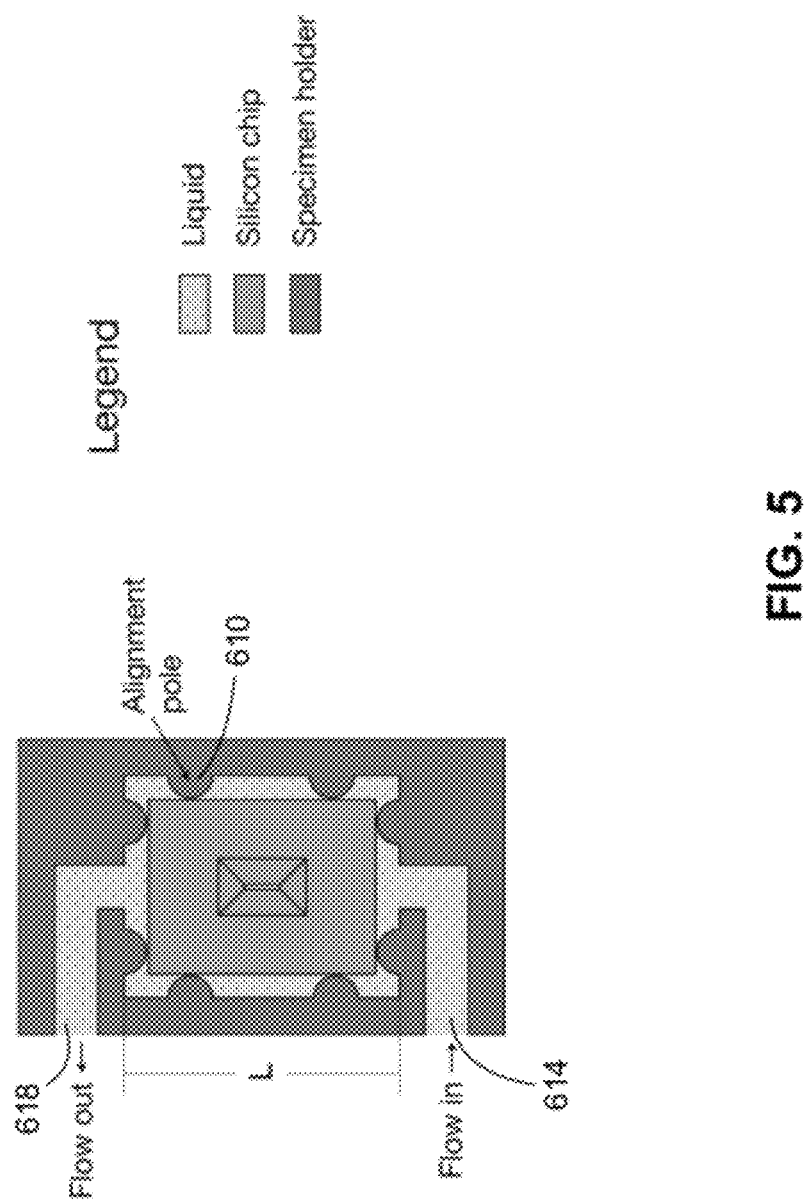
FIG. 5 shows schematically a top cross sectional view of the slot in the tip of a liquid specimen holder, according to one embodiment of the present disclosure [12].

FIG. 5 shows schematically a top view of the slot in the tip 420 of the liquid specimen holder 410, according to one embodiment of the present disclosure. The two microchips 110, 120 are placed on top of each other, with their top surfaces facing each other. They align on their precision made sides via the use of alignment poles 610. Liquid flows from and to liquid ports 614, 618, and along the sides and between the microchips 110, 120. In one or more embodiments, the liquid specimen holder 410 includes means for heating and cooling of the specimens, such as a thermocouple for temperature measurements, a resistive heating wire, and/or a Peltier cooling/heating element (not shown).

The microfluidic chamber 124 is filled with cells and with liquid. Pipes are provided from the sample region to the outside of the microscope for connection to liquid handling equipment. For rapid exchange of the liquid in the pipes, the liquid flow around the microchips serves as a bypass channel. Most of the liquid will be flushed through the bypass channel, as determined by its dimensions. Rapid liquid exchange is needed for three aspects. 1) Nutrients have to be provided to the cells and waste products have to be removed within a controllable period of time, in order to keep the cells alive. This can be done by flowing liquid with nutrients from a bath outside the microscope to the sample region and exchanging the liquid from the sample region. 2) The temperature of the cells has to be precisely regulated, which can be done by flowing liquid of a certain temperature through the system, in addition to other means of temperature regulation. 3) Experiments can be carried out in which the response of cells upon changes of the environment is imaged, for example, upon injection of a certain chemical. The system is not restricted to a flow in and flow out, but additional ports can be added and used, for example, to introduce chemical gradients in the sample area.

Example 3

Live Cell TEM Using a Microfluidic Chamber with Electron Transparent Windows

In one embodiment, typical experimental cells, for example, eukaryotic cells, are seeded on the microchip 120 with spacer 320. The surface 324 of the microchips 120 is made hydrophilic, for example, by plasma cleaning, and the cell adherence may be enhanced by coating with poly-L-lysine. Prior to poly-L-lysine coating, a layer of water repellant may be applied to the SU8 wall, and also to the area enclosed by the SU8, such that cells preferentially grow in the area over the silicon nitride window. Other chemicals may be used as well for this purpose. Cells are seeded locally by micropipetting, only at one side of the silicon nitride window 310, such that the cells fit into the larger sub-chamber 134, 138 when the microfluidic chamber 124 is assembled. Various cell types, for example, COS7 cells tend to adhere on surfaces and stretch out, becoming thinner, and forming long flat edges. Also neurons are known to grow long and thin dendrites. The flat regions of cells will spread out from the nucleus and thereby grow over the regions in the thin sub-chamber 130 with the silicon nitride window. The growth over the silicon nitride window 310 may also be enhanced by placing chemicals at the other side of the window 310 on the microchip 120. The microchip 120 with cells will be placed in the liquid specimen holder 410, or in the tip 420 of the holder only. The cell growth will be monitored with light microscopy, and when the surface coverage is sufficient, the second microchip 110 with the larger sub-chambers will be placed on the microchip with cells, the stack will be pressed together, and the device will be closed. The state of the cells will be further monitored with light microscopy.

After a live cell has been placed in the microfluidic chamber 124, at a certain time-point of interest, the liquid specimen holder 410 will be placed in an electron microscope. The position of the specimen stage is correlated with the cellular positions via recording the position of the edge of a window. The TEM will be used to image the thin regions of live cells. The TEM may be operated in phase contrast mode, or in scatter contrast mode. Typically TEM provides a resolution of a few nanometer on biological materials in samples of a thickness of about 0.5 micrometer. The resolution can be improved by applying energy filtering, to remove inelastically scattered electrons, or by applying correction of the chromatic aberration. For the identification of specific proteins, protein labeling with nanoparticles can be applied, similar to the method used in fluorescence microscopy.

In another embodiment, the TEM is used in scanning mode (STEM). The contrast mechanism of the annular dark field (ADF) detector depends on the atomic number (Z) of the material, and this contrast is used to enhance the visibility of specific labels made of high-Z materials in the low-Z matrix of water and protein. Other imaging modes of the STEM may be advantageous for specific experiments, for example, the bright field mode [8]. In STEM, the thin sub-chamber can be made thicker. It was demonstrated that 1 nm resolution can be achieved on gold labels in a water layer of about 3 micron thickness [9].

In one or more embodiments, nanoparticles of various sizes, shapes, and compositions, each labeling a different protein, can be used to distinguish between different proteins, which is highly relevant for biomedical science, for example, to investigate the composition of protein complexes, and changes thereof.

In one or more embodiments, STEM or TEM can be used in combination with tilt-series tomography to obtain three-dimensional information of specimens.

In yet another embodiment, the chemical composition of the liquid around the cells is changed continuously. Nutrients can be fed to cells to keep them alive. Chemicals, for example, ligands to receptors are provided to the cells. Other biological materials can be fed through the system, for example, viruses, bacteria, proteins, or protein complexes. A gradient of chemicals may be maintained in the chamber to induce the growth of the cells from one towards the other end, though the thin gap. If needed, additional liquid ports can be included.

Example 4

Methods of Live Cell TEM Imaging

Various methods can be used for live cell TEM imaging. In one embodiment, a single image is recorded of a live cell, providing a "snap shot" of the native ultrastructure, as long as the electron dose is kept to a minimum and the imaging settings are such that the first image does not suffer from radiation damage on a length scale larger than the resolution. Especially, when using STEM on labels in a thin flow cell, the imaging can be done very efficiently. Using equations described elsewhere [9], it can be calculated that an electron dose of 1 electron per square Angstrom would be sufficient to resolve gold nanoparticles of 3 nm in a water layer of 0.5 micrometer thickness. A resolution of 3 nm would be sufficient to resolve the constituents of protein complexes. This electron dose is a factor of ten smaller than what is now used in cryo electron microscopy. These numbers are provided as examples only. The imaging parameters can be optimized further for a particular experiment.

In one embodiment, multiple images of live cells are recorded to study dynamics. One can, for example, label a receptor on a neuron and follow its movement on the dendrite. Since the electron microscope does not irradiate the whole cell, it may be possible to image the neuron in a time interval while the neuron is alive during the imaging.

In one embodiment, live cell imaging is performed by combining electron microscopy with light microscopy. The cells can be imaged directly via phase contrast, or fluorescent labels can be attached. The functioning of cells can be studied first with the light microscope, and then, at a certain time-point of interest, the cell can be studied with the electron microscope. The light microscope can be a separate instrument, or be integrated in the electron microscope.

In another embodiment, live cell imaging is performed with ultrafast electron microscopy [10] in combination with the apparatus and methods for live cell TEM. At time-scales well below approximately one microsecond, radiation damage is not likely to propagate farther than a few nanometers. These numbers may strongly vary for different biological system and different microscope settings. Thus, it is principally possible to record a series of images of ultrashort duration. One of such images could capture a native cellular configuration. In one embodiment, a series of images are recorded with ultrafast electron microscopy revealing molecular processes in a live cell.

The combination of time-resolved electron microscopy in liquid opens yet another important possibility. Various biological objects can be imaged while flowing through the chamber. When the imaging time is sufficiently short, these images will capture the native states, which are missed in other high-resolution imaging techniques that are based on imaging of solid samples or deriving information from ensembles.

In yet another embodiment, the microfluidic system is used in combination with fast freezing and cryo TEM. The mass of the microchips 110, 120 is very small and allows for rapid freezing of the biological material enclosed between the two silicon nitride windows 210, 310. Cellular material can be imaged first with light microscopy, and then at a point of interest, the high-speed freezing can be applied. The cells can then be imaged later with cryo TEM. The advantage is that cryo TEM is an established method and that the imaging of the frozen state allows for slower imaging and at a higher electron dose, compared to live cell imaging. The fast freezing can be accomplished, for example, by plunging the tip of the liquid specimen holder in liquid ethane. The tip can be made as separate part. That fits standard cryo TEM equipment.

In a further embodiment, the samples in the microfluidic chamber 124 may be chemically fixed, for example, by injecting glutaraldehyde. This fixation allows for standard TEM and STEM imaging at electron doses of up to a few thousands of electrons per square Angstrom. Although fixation changes the structure of the cells, this methods is routinely used in light microscopy. The imaging of fixed but still wet cells already offers key advantages in terms of artifacts over TEM imaging of conventional thin sections that are resin embedded and dried. Conventional thin sections are well known and have led to many discoveries in cell biology.

The microfluidic system disclosed herein can also be used for other application areas such as related areas in materials science.

Example 5

Further Applications in the Life Sciences

A central challenge in modern biological research is the visualization of the molecular machinery underlying cellular function [A36]. This requires innovative microscopy techniques capable of studying the constituents of cells, many of which are smaller than the wavelength of light. State-of-the-art cryo electron microscopy preserves cellular structures by converting cellular water into amorphous ice via the preparation of cryo sections [A37, A38]. However, the cells are no longer intact or in their native liquid state, and high concentrations of amorphous ice-inducing solutes are often used, which may induce changes in the biological system. There is thus a pressing need for nanoscale microscopy of cells and other biological systems and materials in the liquid state.

Open environmental chambers have been extensively studied for biological imaging, and ESEM [A17] can image the surfaces of pristine cells in a wet environment. The cells must first be transferred to a cooled pure-water environment [A39]. Various microorganisms withstand transfer to pure water, and ESEM provides images of their pristine surfaces [A40]. However, for eukaryotic cells this transfer process alters cellular morphology owing to changes in osmotic pressure. Better images of eukaryotic cells are obtained from fixed, but still hydrated samples [A39]. Including a STEM detector in the ESEM can allow imaging of the intracellular structure [A41].

To preserve cells in as pristine a state as possible, they should be fully surrounded by saline. A liquid capsule can record a backscatter SEM image showing surface receptors labeled with 20-nm-diameter Au nanoparticles on a fixed *Helicobacter pylori* bacterium [A2]. Some particles display sharp contours, whereas others appear blurred; presumably these are at different depths in the liquid. This imaging of Au nanoparticles in water can be high-quality, which is an exciting development, as well-established techniques already allow specific proteins to be labeled with Au nanoparticles [A42]. The liquid capsule can also be used to visualize tissue in fully hydrated conditions after fixation and staining to enhance the SEM contrast [A43]. The liquid capsule is particularly advantageous for questions involving lipid membranes in cells, as these are difficult to preserve during dehydration and washing steps [A44]. Another benefit is that sample preparation and visualization is rapid.

In TEM, environmental chambers [A12, A19, A45] and closed liquid cells [A24] have both been used for biological imaging, although with limited success in competing with the resolution of light microscopy, except when using diffraction techniques [A46]. Instead, as will be discuss below, STEM [A4, A25-A27] provides dramatically improved resolution of Au-labeled structures in the several-micrometers-thick liquid layers needed to enclose eukaryotic cells. Au-labeled epidermal growth factor (EGF) molecules bound to cellular EGF receptors of whole fixed fibroblast cells can be imaged with STEM [A4] at a spatial resolution (on the labels) of 4 nm, using a microfluidic chamber [A25], as discussed above, filled with saline. The produced images can show that the cells were incubated with labeled EGF until endocytosis occurred; the Au nanoparticles are organized into a round shape, interpreted as an endocytic vesicle inside the cell. It is worth noting that no radiation damage effects were observed on the spatial distribution of the labels for the dose used, $7 \times 10^4$ electrons per $nm^2$. Other microscopy methodologies cannot resolve the positions of labeled proteins on intact cells with such high resolution [A47]. First results have also been reported on the imaging of eukaryotic cells that were kept alive in a microfluidic device and then imaged with STEM to study nanoparticle uptake [A48] and to investigate the pristine ultrastructure of yeast mutants [A49].

The combination of electron microscopy with regular cell culture handling and light microscopy is particularly useful in biological investigations [A33]. Standard cell biology experiments can be performed on electron transparent membranes, with the cells imaged with light microscopy and then with SEM after fixation and staining if needed. By imaging multiple cells, the interfacing of neurons [A33] or the effect of cholesterol depletion on microdomain organization in tumour cells [A50] can be studied. The correlative approach has also been demonstrated for (fluorescence microscopy and STEM, to study the locations of receptors specifically labeled with quantum dots [A51], and to image yeast cells [A49].

Example 6

Further Applications in Materials Science

Materials science applications benefit from both the spatial resolution available with liquid cell electron microscopy and its temporal resolution, which allows reaction kinetics and mechanisms to be probed. Electrochemical processes provide an excellent example, with observations possible in a liquid cell that is filled with an electrolyte and also contains electrodes.

Example 7

Visualizing Gold Nanoparticle Uptake in Live Cells with Liquid Scanning Transmission Electron Microscopy The follow text was in part published in [B]. Conjugated nanoparticles (NPs) join distinct nanoscale properties with specific surface bound ligands, a combination that has led to widespread applications in diagnostics and therapeutics. [B1-B4] NPs can for instance be used as efficient contrast agents for molecular imaging, [B5] as carriers for targeted drug6 and gene delivery, [B7] and as therapeutical reagents for targeted photothermal therapy. [B8, B9] Cytotoxicological studies of NPs are a major part of the assessment of NPs for medical applications and include the visualization and characterization of in vitro NP uptake. [B10-B13] NP uptake is influenced by many factors, such as NP size, shape, surface chemistry, colloidal stability, nonspecific interactions, and cell line. [B14-B20] Imaging studies provide crucial information on NP-cell interactions, especially on the intracellular trafficking and fate of NPs and on their incorporated quantity. [B21-B23] Single NPs cannot be resolved with lightmicroscopy, for that reason, electronmicroscopy (EM) is used to record high-resolution images of intracellular NPs. Unfortunately, the sample preparation for EM typically includes processing of samples into [B50-B200] nm thin sections, a step that involves the risk of NP removal. A further disadvantage is the difficulty to quantitatively evaluate NP uptake from conventional EM images, since thin sections may be cut through three-dimensional structures, such as vesicles with high densities of NPs.

Figure 7:
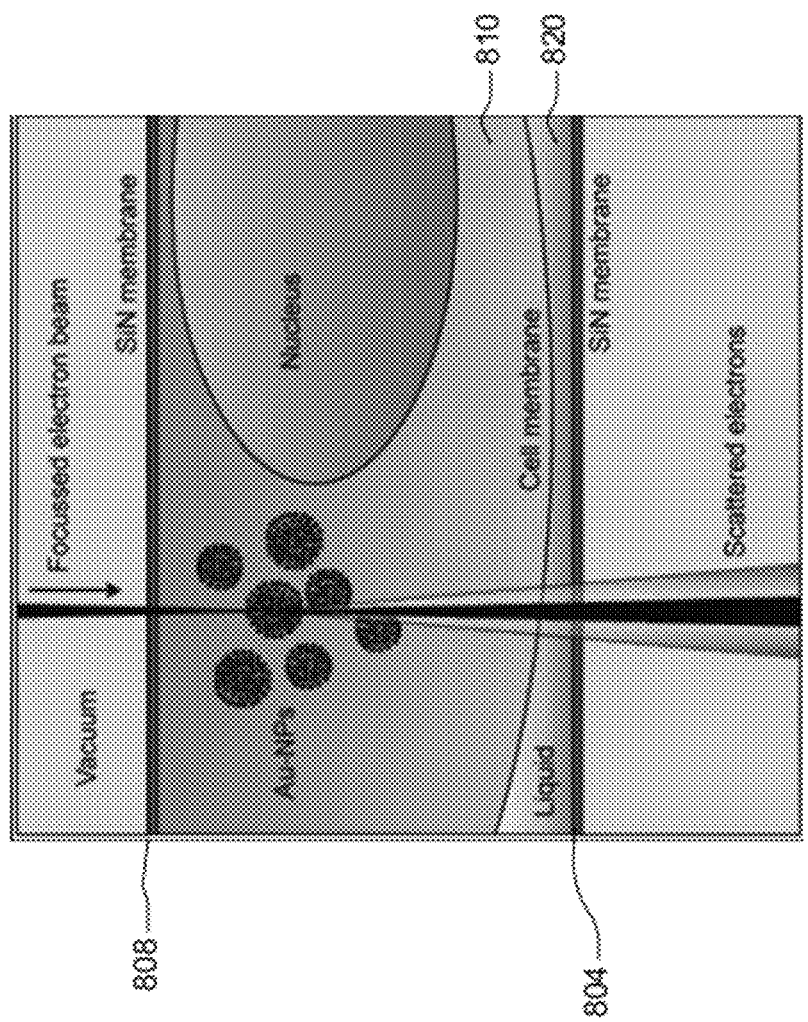
FIG. 7 illustrates the principle of liquid scanning transmission microscopy (STEM) of live eukaryotic cells [B].

A new approach for the study of NP-cell interactions will be described below. Live fibroblast cells (COS-7) loaded with Au—NPs were imaged in liquid with scanning transmission electron microscopy (STEM) using a microfluidic chamber [B24, B25] that provided a continuous flow of buffer. STEM images were recorded through the transparent windows of the chamber; see FIG. 7. More specifically, FIG. 7 illustrates the principle of liquid scanning transmission microscopy (STEM) of live eukaryotic cells. A cell 810 is enclosed in a microfluidic chamber between two 50 nm thin silicon nitride membranes 804, 808 supported by silicon microchips, protecting the cell from the vacuum (gray) inside the STEM. Gold nanoparticles (Au—NPs) accumulate in clusters of Au—NP-filled vesicles. Continuous flow of buffer 820 keeps the cell alive until scanning with the electron beam 830 is started. The cells were alive at the onset of STEM imaging, and the obtained images thus provide information about the NP distribution in pristine cells. This EM approach can be used to study cells of up to ~10 µm thickness, excluding the need for sectioning and requiring only a minimal sample preparation.

In certain embodiments, the microfluidic chamber was made from two silicon microchips, each having a 50 nm thin silicon nitride (SiN) membrane 804, 808 in their center, providing transparent windows for photons and electrons at the energies used in this study. At the same time, the SiN membranes 804, 08 enclosed the liquid in the chamber and thus sealed the cells from the vacuum in the electron microscope. The dimensions of the SiN membranes 804, 808 were 50×200 µm or 50×400 µm. One microchip had a flat surface and was used as substrate for the adhering cells; the second microchip had a 6 µm thick spacer in parallel with the two long sides. This spacer prevented compression of the cells when both microchips were assembled into a microfluidic chamber. The microchips were cleaned, and coated as previously described. [B24] Briefly, the flat microchips (without spacer) were rinsed in acetone followed by a rinse in ethanol (both from Sigma Aldrich) and then ambient air plasma cleaned. To promote attachment of the COS-7 cells, a coating with poly-L-lysine (PLL) (Sigma Aldrich) was applied.

The COS-7 cells (green monkey kidney fibroblast, from ATTC) were grown in Dulbecco's Modified Eagle's Medium (ATTC), with 10% fetal bovine serum (Invitrogen), at 37° C.

in a 5% CO2 environment. To grow cells directly on the microchips, the cells were harvested upon ~90% confluency by rinsing the adherent cell layer with $Ca^{2+}/Mg^{2+}$ free Dulbecco's phosphate buffered saline (GIBCO), incubating the cells with cell stripper solution (MediaTech) and subsequent quenching and suspension in the medium. One droplet of cell suspension was added per PLL-coated microchip. Once a sufficient number of cells (3-12) had settled down on the SiN membrane, usually after a few minutes, the microchips were transferred into new medium and incubated overnight at 37° C. in a 5% CO2 environment.

To ensure that the cells could be kept alive inside the microfluidic chamber, it was first examined the cell survival in the chamber, independently of the recording of STEM images. Cells that had settled on microchips overnight were incubated for 1 h with the live/dead indicator calcein AM (Invitrogen), 1 µM in Tyrode's buffer (TB) (Sigma Aldrich). Calcein AM is an initially nonfluorescent, cell permeable compound that is converted into green fluorescent calcein when hydrolyzed by intracellular esterases in live cells. To enclose the cells in a microfluidic chamber, two microchips, one with cells and one with spacer, were assembled in the liquid flow EM specimen holder (Protochips Inc.). First, the dry microchip with spacer was placed in the tip of the holder, with the spacer side up. The wet microchip with adhering cells upside down was placed (rapidly to prevent drying) on the spacer microchip. Due to the design of the slot, this "sandwiching" procedure aligned the microchips with a precision of 20 µm such that their SiN windows overlapped to a degree of at least 80%, providing visibility of the cells enclosed between the membranes. The microfluidic compartment was closed with a lid, and the flow of the imaging buffer (1 µM Calcein AM in TB) was initiated. The total assembly time amounted to 1-2 min.

Figure 8:
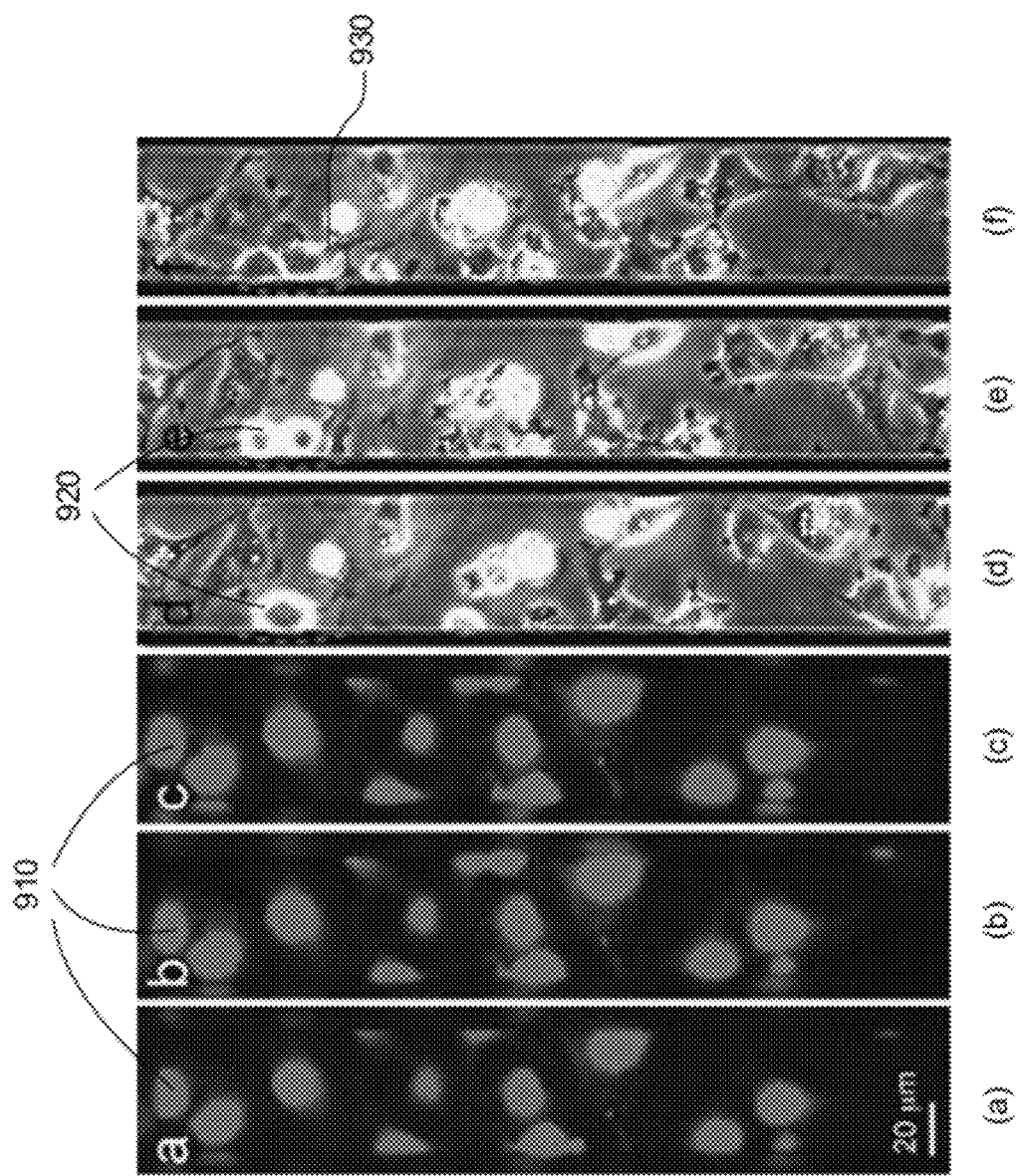
FIG. 8 shows assessment of cell viability [B].

The cells were imaged with an inverted fluorescence microscope (Nikon Diaphot 300), equipped with 20× (Nikon Plan 20/0.40 phase 2 160/1.2) and 40× (Nikon Plan 40/0.55 phase 3 160/0-2.5) air lenses and an EXFO X-Cite 120PC XL illumination system that included a 120 W mercury arc lamp. FIG. 8 shows assessment of cell viability. More specifically, FIG. 8 shows (a) fluorescence microscopy of live COS-7 cells 910 on a microchip. The cells 910 were stained with the live/dead indicator calcein AM (green fluorescence indicates undamaged membrane integrity). Further, FIG. 8 shows (b) the same cells 910 2 min after enclosure in a microfluidic chamber. Further, FIG. 8 shows (c) the cells 910 after opening of the microfluidic chamber 40 min later. Further, FIG. 8 shows (d) phase contrast image of a different sample of live COS-7 cells 920 39 h after opening of the microfluidic chamber. The dotted oval in the upper left image area indicates the cell that underwent mitosis. Further, FIG. 8 shows (e, f) cells division occurring in a time period of 2 h. The fluorescence image of FIG. 8*a* shows the cells 910 on a microchip before enclosure. FIG. 8*b* is the same sample in a closed chamber, about 2 min after assembly. FIG. 8*c* was taken 40 min after the microfluidic chamber had been reopened; the cells were enclosed for 4 mins total. None of the cells 910 displayed signs of damage. Several other samples were tested as well. Cells in the microfluidic chamber kept their calcein fluorescence intensity unchanged for the maximal tested time period of 2.5 h, indicating that the cells were alive for at least 2.5 h in the microfluidic chamber. Note that the cells 910 lost their viability in the chamber within 15 min without the flow of buffer.

To examine if the enclosing process caused delayed cellular damage, several samples are inspected for cell division, i.e., mitosis, the occurrence of which is the most stringent criterion of cell viability. Because mitosis is temperature dependent and the liquid flow holder had no internal heater, the microfluidic chamber was reopened and the microchip is placed with the cells in a dish filled with $CO_2$-independent medium (Invitrogen). The dish was transferred onto the stage of the microscope, equipped with an environmental system to ensure a constant temperature of 37° C. and 100% humidified air. The total time the samples spent in the microfluidic chamber was reduced to 4 min, because the cells adhered to the spacer microchip after 5 min, causing cell rupture upon opening of the microfluidic chamber. During the following 53 h, a time-lapse series of phase-contrast images was recorded with 3 min intervals, revealing three mitosis events at the location of the SiN window. A mitosis that happened after 39 h is shown in the area of the dotted oval in FIG. 8*d-f*. Cells 920 were also tested for signs of programmed cell death, [B26] i.e., apoptosis, by incubating the samples for 30 min in Hoechst 33342 (Invitrogen), 1 µg/mL in TB, a nuclear fluorescent stain. None of the tested cells had developed signs of programmed cell death 53 h after opening of the microfluidic chamber. Similar results were obtained for two further samples. Cells kept in the microfluidic chamber were thus viable following the most stringent criterion of viability, namely, mitosis.

It was possible to keep the COS-7 cells alive and intact in the microfluidic chamber. Thus, STEM experiments can be conducted to study the fate of NPs taken up by COS-7 cells. Microchips with adherent cells were serum-starved for 2 h to enhance the following uptake of serum protein coated Au—NPs. [B27] Thirty nanometer diameter unconjugated Au—NPs (Ted Pella) were coated with serum proteins by mixing 0.5 mL of the Au—NP stock solution with 2 mL of 10% FBS supplemented medium and subsequent incubation at 40° C. under rotation (30 rpm), for 2 h. Such serum protein coating has been shown to prevent clustering of the Au—NPs and to favor their endocytotic uptake.[17] The Au—NP solution was centrifuged for 6 min at 5000 g and the pellet was dissolved in 10% FBS supplemented medium, to yield a final volume of 60 µL with an Au—NP concentration of ~1.8 nM. Twelve microliter droplets of this Au—NP solution were placed against the inner rim of cutoff PCR tube lids. Microchips with serum-starved cells were individually placed in an inclined orientation against a droplet, such that the cells were submerged and upside down in the Au—NP solution and incubated for 2 h in a humid environment, at 37° C. in the $CO_2$ incubator. Subsequently, the samples were rinsed and incubated overnight in 10% FBS supplemented medium, at 37° C. in the CO2 incubator. After 24 h, the cells were enclosed in the microfluidic chamber.

Figure 9:
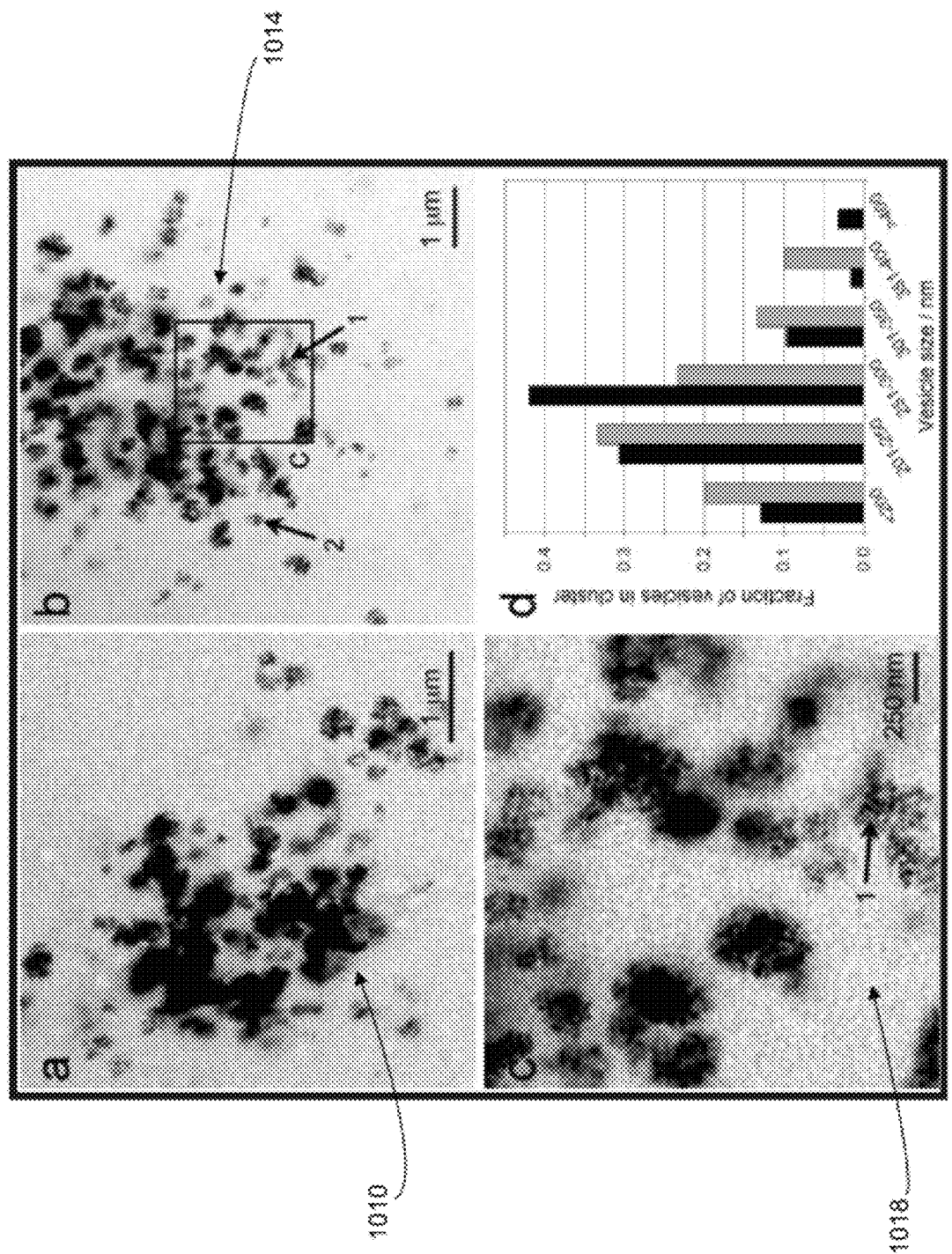
FIG. 9 shows STEM of live cells in a microfluidic chamber, 24 h after incubation with Au—NPs [B].

Imaging with liquid STEM took place within 3 min after enclosure. The STEM (CM200, FEI Company, Oregon) was set to 200 kV, a beam semiangle R of 9 mrad, a pixel dwell time of 20 µs, a probe current of 0.16 nA, a magnification of 16000, a pixel size of 8.7 nm, an image size of 1024×1024 pixels (representing sample areas of 8.8*8.8 µm2), and an annular dark field detector semiangle of 70 mrad. FIG. 9 shows STEM of live cells in a microfluidic chamber, 24 h after incubation with Au—NPs. More specifically, FIG. 9 shows (a, b) images of intracellular Au—NP aggregations in two different cells 1010, 1014, illustrating that Au—NPs had concentrated in three-dimensional clusters of vesicles densely filled with Au—NPs. Further, FIG. 9 shows (c) detail of panel b showing the distribution of single NPs 1018. Blurred Au—NPs are located outside the focus plane and illustrate the highly three-dimensional arrangement of the structures. Further, FIG. 9 shows (d) normalized size distribution histogram of Au—NP filled vesicles shown in panel a (gray) and panel b (black). Panels a and b of FIG. 9 show selected cell areas of 4.9×4.9 µm² (FIG. 9a) 7.4×7.4 µm² (FIG. 9b), depicting two representative intracellular clusters that consisted of vesicles with Au—NPs, appearing as dark spots. The average diameter of this type of cluster was measured from light microscopy images and was 4.6±1 µm (n=25), where the variation represents the standard measured sizes, and the measurement accuracy was 0.5 µm. The STEM images revealed that each cluster contained more than hundred round structures that were densely filled with Au—NPs. Due to their approximate round shapes and their filling with Au—NPs, it is suggested here that these structures are vesicles. FIG. 9c is a detail of FIG. 9b highlighting the distribution of single NPs inside the vesicles. The STEM images display the Au—NP-filled vesicles with different degrees of sharpness; this indicates that they were not on the same focal plane, but scattered over several micrometers in depth. The sharpest NP images can be found when these are in the focal plane and at a vertical location close to the top window, where the electron beam enters the sample. The electron probe is blurred toward layers deeper in the specimen due to a combination of geometric broadening and beam broadening on account of interactions of the electron beam with the specimen. A fraction of 63% of the probe current was scattered into the opening angle of the detector, from which it was calculated the thickness of the liquid [B24] to be 10±2 µm. The Au—NPs appear as black spots on account of this large liquid thickness, leading to a contrast reversal. For thinner liquids the Au—NPs appear as bright spots. The liquid thickness was thicker than what was expected on the basis of the spacer of 6 µm, and can be explained by a bulging of the SiN windows outward into the vacuum. [B25]

STEM imaging of pristine cells is subject to radiation damage. Yet, the STEM images do not show signs of severe damage. The majority of the Au—NP-filled vesicles in FIG. 9 had round or oval shapes, and the pattern of intravesicular Au—NPs appeared homogeneous. The cells were exposed to $2\times10^4$ electrons per scan pixel of a size of 8.7 nm, and the average electron dose was thus 3 e$^-$/Å2. The electron dose was a factor of 10 above the dose limit for EM above which subnanometer structural features become damaged in wet biological specimens, [B28] and a factor of 10 below the corresponding limit used in cryo-EM.[B29] Note that the local electron dose directly in the focal plane was higher, maximal $1.6\times10^2$ e$^-$/Å2 (for a diameter of the electron probe containing 50% of the current of 0.9 nm). But, only a small region of a cell was exposed to the higher dose, because electron beam scanning occurred with lines separated by the pixel size of 9 nm, and beam broadening rapidly decreases the radiation intensity in deeper layers.30 The absence of signs of severe radiation damage in the images and the fact that the average electron dose was smaller than the dose used in cryo-EM lead to the hypothesis that the first image recorded on a cell can be used to assess the distribution of NPs inside a live cell.

FIG. 9 shows that the Au—NP filled endocytotic vesicles had accumulated into a large cluster. Similar conglomerations of NP-filled vesicles have been reported for several types of NPs in the vicinity of the endosomal recycling compartment (ERC), a perinuclear organelle involved in endosome recycling. [B19, B31-B33] To determine the number of Au—NP-filled vesicles per cluster, the original STEM images were analyzed, of which selected areas are shown in panels a and b of FIG. 9. Vesicles were visually identified and counted if their contrast exceeded the background gray value by at least 30% and if their size was >100 nm. The counting was repeated four times per image resulting in a total of 117±9 (cluster of FIG. 9a) and 164±4 (cluster of FIG. 9b) NP-filled vesicles. It cannot be excluded that several NP-filled vesicles might have been located outside the image area; therefore these numbers represent minimum values. This applies particularly for the cluster shown in FIG. 9a, because beam blurring possibly prevented the identification of additional vesicles.

From vesicles that were in or close to the focal plane, the average diameter was measured to be 0.26±0.05 µm (n=63, FIG. 9b; n=30, FIG. 9a). The diameters were measured from the STEM images using Image J (NIH). The distribution of vesicle sizes is depicted in FIG. 9d and shows a maximum for vesicle diameters between 200 and 300 nm in both analyzed clusters. This size distribution histogram is similar to the size distribution of lysosomes. [B34, B35] Since the endocytotic pathway shuttles cargo from vesicles to early endosomes to late endosomes/multivesicular bodies and finally, for degradation, to lysosomes, it is proposed that 24 h after their intracellular uptake the Au NPs had ended up in lysosomes.

Figure 10:
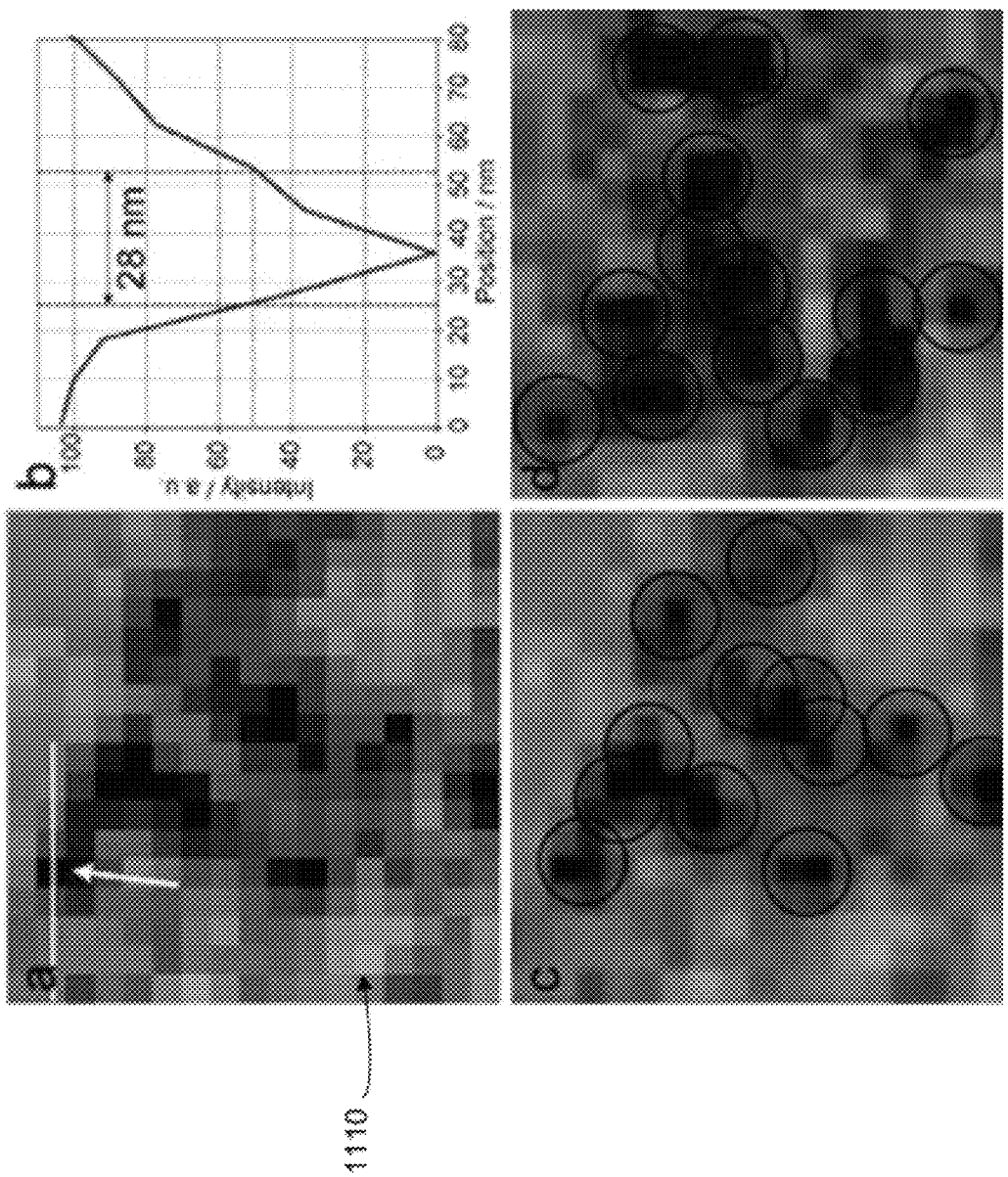
FIG. 10 shows STEM image analysis used to determine the density of Au—NPs in vesicles [B].

To assess the distribution of Au—NPs within the vesicles, the Au—NPs in selected vesicular regions of 17×17 pixels (150×150 nm²) are counted. FIG. 10 shows STEM image analysis used to determine the density of Au—NPs in vesicles. More specifically, FIG. 10 shows (a) selected region of 17×17 pixels at arrow #1 in FIG. 9b. Further, FIG. 10 shows (b) a line scan was drawn over a darker region assumed to represent an Au—NP in (a) (see arrow). The full width at half-minimum was 28±5 nm. Further, FIG. 10 shows (c) filtered image used for the counting of Au—NPs (circles). Further, FIG. 10 shows (d) selected region at arrow #2 in FIG. 3b displaying 14 Au—NPs. FIG. 10a shows an example that represents such an area from the vesicle at arrow #1 in FIG. 9b. FIG. 10b shows a line-scan over a region with darker pixels, presumed to represent an Au—NP, having a full width at half-maximum of 28±5 nm, which corresponds to the 30 nm diameter of the Au—NPs. Individual NPs can thus be recognized but the image is so pixelated that Au—NP counting is difficult. To facilitate the counting of NPs, the image in FIG. 9b was processed with Image J (NIH), first by enlargement of a factor of 10 and then by filtering with Gaussian blur with a radius of 1.5 pixels. In the filtered image of FIG. 10c the NPs can be recognized better than in the original image. In this example, a total of 12 Au—NPs was counted as indicated by the circles. An example from another region is shown (image processed) in FIG. 10d (arrow #2 in FIG. 9b); here, it was counted 14 Au—NPs. A total of 25 of such image sections were placed over vesicles and analyzed and yielded an average of 12±2 Au—NPs.

The degree of overlap of Au—NPs in these vesicular image areas was sufficiently low, such that one could identify and count individual NPs, and a homogeneous distribution of the Au—NPs was found throughout the analyzed areas. This distribution points toward localization of the NPs at the membrane of the lysosomes, rather than to a complete filling of the entire intravesicular space. If this entire space would have been filled, one would expect to see a higher density of Au—NPs in the central parts of the vesicles compared to the periphery, which was not the case. The degree of coverage of the vesicle membrane by Au—NPs was determined as follows. The surface area of an average sized vesicle was 0.21 (0.07 µm² assuming a spherical shape. A 30 nm large gold sphere with a 5 nm thick layer of bound serum protein yields an effective Au—NP diameter of 40 nm. On account of the curvature of the inner vesicle surface and assuming a monolayer of tightly packed Au—NPs, a single Au—NP would occupy an area of ~50×50 nm², and the theoretical maximum density is thus 400 Au—NPs/µm² on the inner vesicle surface. Consequently, an average vesicle could hold a maximum of 85±30 Au—NPs (Table 1).

TABLE 1

Quantitative Analysis of Au-NP Distribution[a]

| | |
|---|---|
| number of vesicles in cluster | 164* ± 4 |
| vesicle diameter (µm) | 0.26* ± 0.05 |
| estimated vesicle surface area (µm²) | 0.21 ± 0.07 |
| number of detected Au-NPs per 0.15 × 0.15 µm² of image | 12* ± 2 |
| density of Au-NPs/µm² on vesicle membrane | 267 ± 44 |
| number of Au-NPs/vesicle | 57 ± 26 |
| theoretical max. number of Au-NPs/vesicle | 85 ± 30 |
| theoretical max. density of Au-NPs/µm² on vesicle membrane | 400 Au-NPs/µm² |
| occupancy of available vesicle membrane area | 67 ± 11% |
| total number of Au-NPs in vesicle cluster | (9 ± 5) × 10³ |

[a]Values marked with an asterisk were directly determined from the STEM image of FIG. 9b.

The actual number of Au—NPs in an image, projecting both the upper and lower halves of a vesicle, was 12 (2 in an area of 2×0.15×0.15=0.045 µm². The actual density at the I thus 267±44 Au—NPs/µm2, and a vesicle contained an average 57±26 Au—NPs, which corresponds to 67±11% occupancy of the available membrane area. The total number of Au—NPs in the lysosome cluster was estimated to be (9±5)×10³.

The finding that Au—NPs are bound to the inner vesicular surface is supported by some studies of Au—NPs in intracellular vesicles using conventional EM images. [B20] However, there is a controversy about such a vesicular membrane bound location, and several other published EM images show intravascular NPs that form aggregates in the vesicles [B13, B36, B37]. In addition, EM images often depict only a few NPs per vesicle [B18, B7-B39], possibly underestimating the occupancy of the available area by NPs. These discrepancies in the location and in the amount of vesicular NPs might relate to concerns about the sectioning of EM samples [B1]. First, one cannot be sure where a vesicle was cut through, which complicates quantitative studies. Second, EM sample preparation is prone to introduce artifacts [B40] hindering quantification in NP uptake studies. The issue of artifacts is multifaceted. NPs may become displaced by the diamond knife [B41], or may be washed away during sample preparation. Cell fixation can redistribute NPs coated with cell-penetrating peptides into the nucleus [B42], and translocate NPs with positively charged proteins across the cell membrane [B43]. Staining can introduce electron-dense nanosized aggregates that are difficult to distinguish from the NPs under investigation [B36, B44]. Third, with conventional EM it is almost impossible to conduct a quantitative study on the scale of the entire cluster of vesicles. In order to do so, many images from a large number of sections would have to be analyzed [B45].

Liquid STEM, on the contrary, achieves single NP resolution on fully hydrated, nonfixed, intact cells that are living at the onset of imaging. The images contain signals from the full three-dimensional space of the cell, which can be used for quantitative studies of NP uptake and spatial distribution as demonstrated in this work. The whole cell analysis can be done on a much faster time scale (hours versus days) than possible with conventional EM [B41], making the STEM approach suitable for routine measurements, needed for instance when systematic variations of NP materials and surface coating are included in the uptake study [B21]. The biological structure of the cells cannot be visualized with high resolution using electron microscopy of whole cells in liquid, because the contrast obtained on the carbon-based materials within water is too low. The cellular structure may be visualized using fluorescent probes and light microscopy, which can be correlated with the STEM images. Future studies on cell-NP interactions may well include such a fluorophore labeling to identify specific proteins and pathways that participate in NP uptake, trafficking, storage, and exocytosis, by light microscopy prior to STEM imaging.

The intracellular uptake of 30 nm diameter Au—NPs in COS-7 cells with liquid STEM is studied. The spatial distribution of NPs was determined in fully hydrated, pristine cells that were alive at the onset of imaging. On account of the absence of preparation of the cells into thin sections standard in EM, a quantitative analysis of the NP distribution is conducted. The NPs were located in vesicles, possibly lysosomes. A total of 117±9 and 164±4 vesicles were found in two analyzed clusters after 24 h of incubation. The NPs were bound to the membranes of the vesicles, with 57±26 Au—NPs/vesicle. About 67% of the available membrane surface area was covered with NPs. The total number of Au—NPs in the vesicle cluster was (9±5)×10³. It is proposed that liquid STEM of live cells can be used for quantitative studies of NP-cell interactions.

Example 8

Fully Hydrated Yeast Cells Imaged with Electron Microscopy

The following text was in part published in [C]. Demonstrated below is electron microscopy of fully hydrated eukaryotic cells with up to 32-nm resolution, an order of magnitude better than the resolution of conventional light microscopy. *Schizosaccaromyces pombe* cells, widely used as a model organism in molecular and cell biology [C13], were loaded in a microfluidic chamber, kept alive, and then imaged in liquid with scanning transmission electron microscopy (STEM) [C14]. The cells were imaged in their pristine state, without genetic modification, to include fluorescent labels, staining, sectioning, etc. The native intracellular ultrastructure of wild-type cells and three different mutants was studied in vivo.

Materials and Methods

Yeast Cell Cultures

Liquid cultures of *S. pombe* cells, wild-type 972, spn3Δ mutant, and temperature sensitive orb6-25, and cdc25-22 cdc15(27A) mutants, were grown for 24 h in 25 ml liquid consisting of YES broth media, 0.3% yeast extract, 0.3% malt extract, 0.5% peptone, and 1% D-glucose, with 50 mg/L each of adenine, histidine, leucine, uracil, and lysine (Sunrise Science Products, San Diego, Calif.) in a 25° C. incubator with shaking at 250 rpm. The optical density (OD) was determined with a spectrometer at 595 nm (Evolution 60, Thermo Scientific, Waltham, Mass.) and the wild-type and spn3Δ mutant cells were harvested when the OD value reached 0.3, indicating that the cultures were in the log phase of their growth curve. The orb6-25 mutant cultures were further grown at 36° C. for additional 3 h. From each culture, 10 ml was harvested by centrifugation (10 min/2000 rpm). The cells were washed with 10 ml of sterile 10-mM Na-HEPES supplemented with 2% D-glucose (both from Sigma Aldrich, St. Louis, Mo.) at pH 7.2 (NaHEPES). Pellets were resuspended in 1 or 2 ml of NaHEPES. A 20 mM FUN-1 (Invitrogen, Carlsbad, Calif.) stock solution in NaHEPES was prepared and added 1:1 to the yeast-cell suspension, yielding 10 mM FUN-1 final concentration. The cultures were incubated in the dark for at least 60 min before fluorescence microscopy was performed to check for the red fluorescent staining of vacuoles, indicating viability of the cells, or for bright and more uniform yellow-green fluorescence, indicating a dead or dying status [C15].

Preparation of the Microfluidic Chamber with Yeast Cells

The liquid STEM system consisted of a microfluidic chamber assembled from two silicon microchips with electron-transparent windows and a liquid flow specimen holder (Protochips, Raleigh, N.C.) [C14, C16]. The electron-transparent windows spanned an area of 50×400 mm and were made of 50-nmthick silicon nitride. The microchips were plasma-cleaned to render the surfaces hydrophilic, then coated with poly-L-lysine (Sigma-Aldrich) to enhance cell adherence and to maintain the surface hydrophilic. Gold nanoparticles of sizes 5, 10, and 30 nm were applied to the upward-facing window, serving as a guide for focusing of the STEM (except for FIGS. 14A and 15A). The microfluidic chamber was loaded with live S. pombe cells by placing a droplet of a suspension of cells in buffer solution on a microchip forming the lower half of the chamber. The microfluidic chamber was then closed with a second microchip. The loading procedure was completed within 1 min, and light microscopy and STEM images were recorded within a few minutes.

Light Microscopy

After the specimen holder was loaded with live yeast cells, it was placed on a mechanical translation stage with three directions of movement. The tip of the specimen holder containing the microchips was positioned in a water droplet above a 60×, 1.0-numerical-aperture water-immersion lens on an inverted microscope (TS100, Nikon, Tokyo, Japan). Images were recorded at room temperature using a 3-megapixel charge-coupled device camera (Micropublisher 3.3 RTV, QImaging, Surrey, British Columbia, Canada), and Qcapture software, and stored in 8-bit tiff format. The positions of the cells with respect to the four corners of their silicon nitride windows were used to correlate the STEM images with the light-microscopy images. Fluorescence imaging showed that the S. pombe yeast cells could be kept alive for extended periods of up to hours in the microfluidic chamber (data not shown). The images were adjusted for optimum brightness and contrast, cropped, and color-enhanced using Image J software (National Institutes of Health, Bethesda, Md.).

Liquid STEM Imaging

The STEM (CM200 TEM/STEM, Philips/FEI, Hillsboro, Oreg.) was set to 200 kV, with a beam semiangle a of 5.6 mrad, a probe current of 0.22 nA, and an annular dark field (ADF) detector semiangle of 70 mrad (Fischione Instruments, Export, Pa.). STEM images of 1024×1024 pixels were recorded at room temperature using ES Vision software (Philips/FEI) with a pixel dwell time of 10 ms and a pixel size of 25 nm (magnification 4800×), and stored as 16-bit tiff files. The electron probe diameter containing 50% of the current was calculated to be 0.9 nm, resulting from 0.85 nm under ideal circumstances at the used beam semiangle (17) plus an estimated contribution of ~0.3 nm due to instabilities and imperfections of the alignment, added quadratically. An imaging session started by localizing the edge of a window with the electron microscope set to fast scanning in searching mode, such that the positions of the yeast cells in the STEM images could be correlated with their positions in the lightmicroscopy images. The microscope was then focused using the contrast obtained on the gold nanoparticles. The stage position was changed to the direction of a yeast cell of interest as located from its fluorescence image. By repeating stage movements and refocusing, the cell of interest was approached. As soon as the cell of interest appeared in the field of view, a STEM image was recorded. To enhance the visibility of the cellular structures, the images were filtered with a convolution filter with a kernel of (1,1,1,1,3,1,1,1,1) in ImageJ (NIH). The gamma level was set to 0.75, and the contrast curve, contrast level, and brightness level were adjusted for maximal visibility of the biological structures (Adobe Photoshop, Adobe, San Jose, Calif.). The red channel of the fluorescence image (see FIG. 12B) was overlaid after adjustment for the difference in magnification and for image rotation (Adobe Photoshop) (see FIG. 12C).

Measuring the Liquid Thickness

The liquid thickness was measured using STEM by comparing the fraction N/N0 of the incoming electrons scattered onto the ADF detector. The thickness of the liquid T follows from this fraction as $(14,18) T=-1(\beta)\ln(1-N/N_0)$, with $1(\beta)$ the mean-free-path length for elastic scattering into detector opening semiangle b or larger. Water has 1 water ¼ 10.5 mm for b ¼ 70 mrad. It was determined a liquid thickness of 652 mm, which is consistent with the diameter of the yeast cells (see FIG. 12C). The thickness was 3±1 μm at the corner of the window, i.e., the windows bulged outward at the locations of the yeast cells. The fringes in the phase-contrast microscopy image (see FIG. 12A) confirm bending of the silicon nitride window. The liquid thicknesses were 4±1 μm, 4±1 μm, 3±1 μm, and 3±1 μm, respectively (see FIGS. 13, C and D, and 14, A and B). In the latter images, the yeast cells had probably flattened in the microfluidic chamber.

Measuring Object Dimensions

The cell wall thickness observed (see FIG. 12C) was measured from line scans made with a width of 6 pixels and a direction perpendicular to the bright line outlining the yeast cells, and by calculating the full width at half-maximum of the intensity peak of the line scan. Measurements were taken at five positions to produce an average value of 0.19±0.04 μm. The diameters of six vesicles with dark contrast (lipid vesicles) were determined from their full width at half-minimum values, for an average value of 0.35±0.08 μm. The average diameter of seven bright vesicles was 0.16±0.02 μm.

Results

Correlative Light Microscopy and STEM of Live S. pombe Cells

Figure 11:
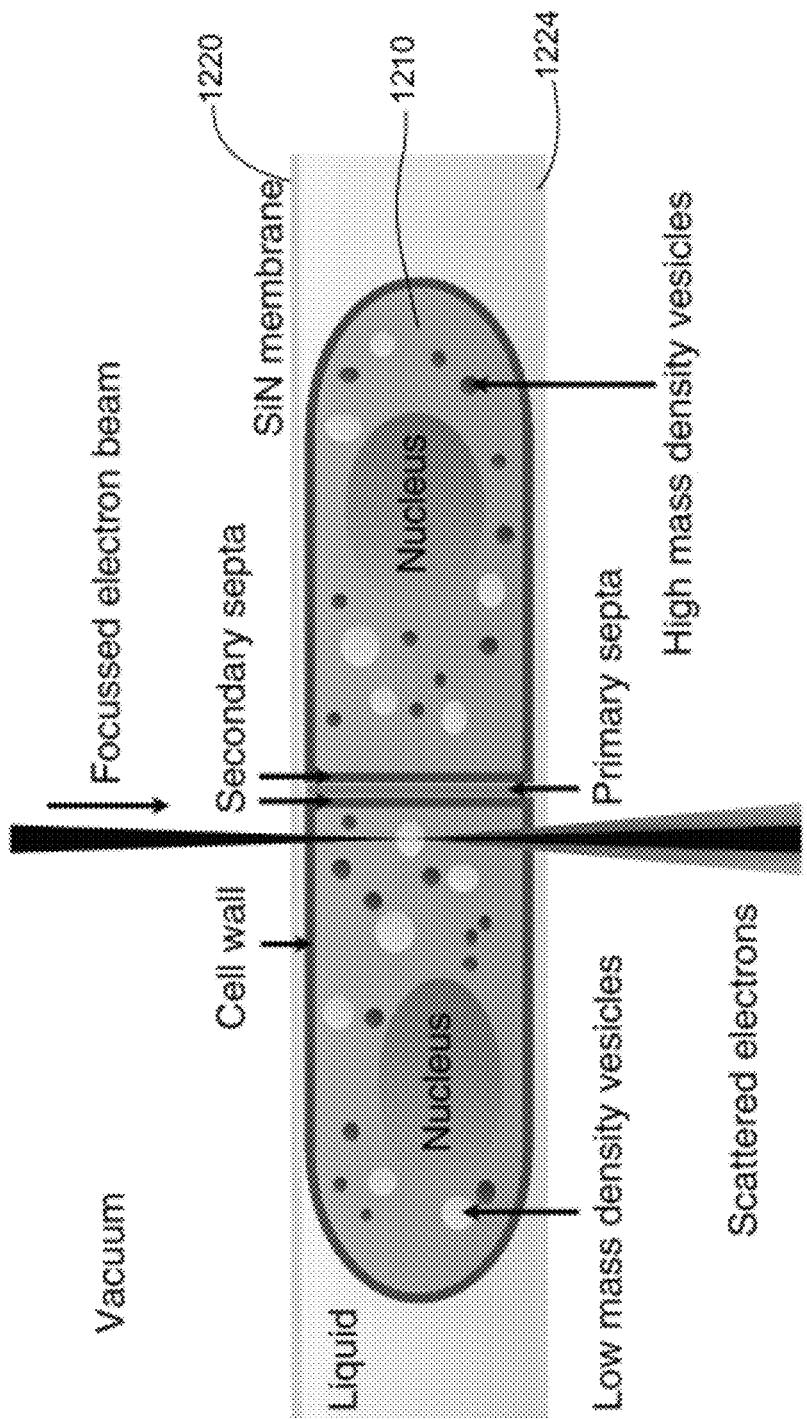
FIG. 11 schematically shows a dividing *S. pombe* cell surrounded by liquid and contained between two silicon-nitride windows, transparent for photons and electrons [C].

S. pombe cells are cylindrical, with a diameter of ~4 μm and a length of ~6-15 μm. They grow by elongation of their ends and divide by medial septation, followed by cleavage of the primary septum. The yeast cells were placed in their fully hydrated, normal physiological state at ambient temperature in a saline-filled microfluidic chamber [C16] with ultrathin windows for STEM of liquid specimens (FIG. 11). FIG. 11 schematically shows a dividing S. pombe cell 1210 surrounded by liquid and contained between two silicon-nitride windows 1220, 1224, transparent for photons and electrons. In STEM, the electron beam scans a defined area of the specimen, and the scattered transmitted electrons are used for detection. The contrast in the STEM images depends on the mass density and the atomic composition of the biological materials. The windows separated the liquid from the vacuum of the EM, and were transparent to the photons and electrons of the energies used here. The microfluidic chamber was contained in an EM specimen holder for liquid specimens. The loading procedure was completed within 1 min. To verify that the cells in the microfluidic device were indeed living before STEM, the cells were incubated with a yeast-specific fluorescent live-dead indicator. For lightmicroscopy examination of the yeast cells, the EM specimen holder was positioned on a water immersion lens.

Figure 12:
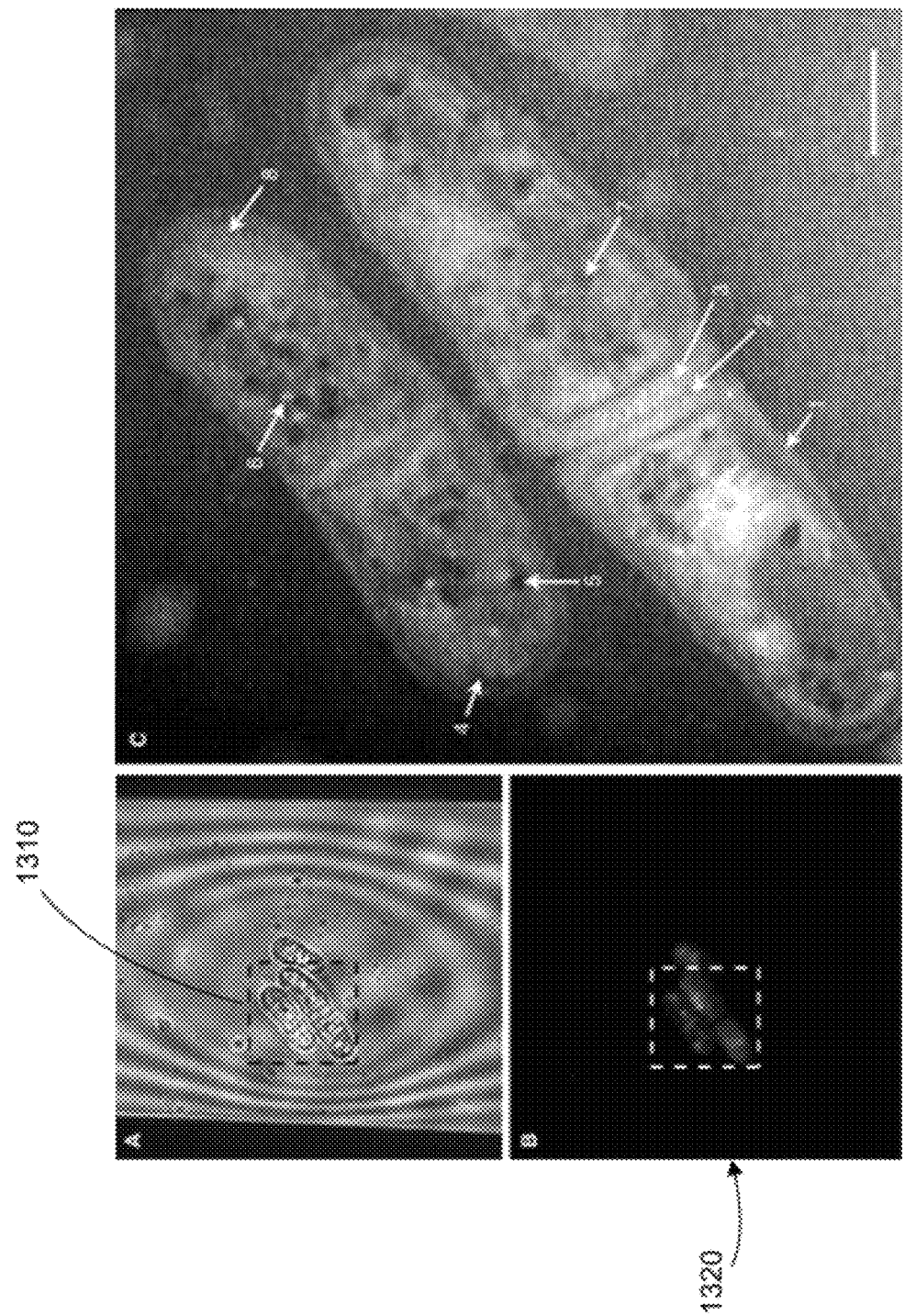
FIG. 12 shows light microscopy and liquid STEM of fully hydrated wild-type *S. pombe* yeast cells, which were alive at the onset of the recording of the first STEM image [C].

FIG. 12 shows light microscopy and liquid STEM of fully hydrated wild-type S. pombe yeast cells, which were alive at the onset of the recording of the first STEM image. More specifically, FIG. 12 shows (A) phase-contrast image showing S. pombe cells 1310 within a portion of the viewing window of the microfluidic chamber. Further, FIG. 12 shows (B) in the corresponding fluorescence image 1320, it can be seen that all cells accumulated FUN-1 dye and emitted a punctuated red fluorescence, the typical signal of living yeast cells. Further, FIG. 12 shows (C) Liquid STEM image recorded in the fully hydrated state of the same pristine yeast cells as shown in A and B. Numbered arrows indicate examples of allocated organelles: the cell wall (1), the primary septum (2), the secondary septum (3), a cell membrane invagination (4), a lipid droplet (5), a peroxisome (6), an unclassified vesicle (7), and a gold nanoparticle (8). The color is an overlay of the red channel of the fluorescence image (B). Further, FIG. 12 shows a scale bar of 2 mm. The phase-contrast image of FIG. 12A depicts three S. pombe cells, two of which had just divided. The fluorescence image of FIG. 12B shows bright red spots within the cells, indicating that the dye was transported into vacuoles in living cells, a process that is only possible in living cells. There was no sample preparation apart from the incubation with the dye after the yeast cells had been washed and transferred into the imaging buffer at the time the culture had reached the log phase of its growth curve.

Within a few minutes after the recording of the lightmicroscopy images, the specimen holder was transferred to the vacuum chamber of the electron microscope. Here, the same yeast cells were localized and imaged while still in their liquid environment. The cellular structures as imaged with light microscopy were correlated with their EM counterparts via their previously determined coordinates on the SiN window. The STEM image of FIG. 12C shows the two dividing cells and the edge of a third cell seen in the light-microscopy image. FIG. 12C reveals intracellular components with details down to the ultrastructural level, such as the cell wall, the primary and secondary septa, and different types of intracellular vesicles. The upper cell appears to be in the process of division, whereas the lower cells were already in the process of separation after cell division. The red color indicates the locations of the vacuoles, albeit with a limited precision on account of the limited spatial resolution of the fluorescence image. The background appears darker in the left upper corner with respect to the right lower corner, due to a variation of the liquid thickness over the field of view. Gold nanoparticles applied to the upper window for focusing purposes are also visible. Fluorescence microscopy of similar samples showed that the yeast cells were not viable after STEM imaging. Even though the cells were killed by exposure to the electron beam in the STEM, the ameliorating fact is that the cells were living at the onset of the recording of the first micrograph. The STEM image of FIG. 12C thus represents the ultrastructure of pristine S. pombe cells in liquid.

Assignment of Visible Structures to Known Organelles

The visible structures in the STEM images are assigned to known yeast organelles using information about organelle morphology, size, and mass density. The first and most prominent feature of all yeast cells is their outer 0.1- to 0.2-mm thick cell wall, composed mainly of polysaccharides [C19]. The cell wall emerged brighter in the image than the surrounding buffer (FIG. 12C, arrow 1). The contrast obtained with STEM depends on the atomic number(s) and the mass density of the material in the path of the electron beam [C20]. The brighter signal indicates a higher mass density than the aqueous medium surrounding the cells, consistent with the higher mass density of 1.3 g/cm$^3$ of the cell wall (21). The measured thickness of the bright line was 0.19±0.04 µm, in agreement with published values for the thickness [C19], noting that the cell wall will appear broader in the image, since it represents a projection through the three-dimensional shape of the cell wall. The cellular regions enclosed by the cell wall appear brighter than the surrounding liquid, as explained by their content of protein, lipids, and DNA, all with a higher mass density than the surrounding imaging buffer. As expected from the harvesting at their log phase growth, many cells in the samples were in the process of division and had a septum composed of a central primary septum (FIG. 12C, arrow 2) flanked on each side by secondary septa (FIG. 12C, arrow 3). Some cells exhibited finger-like, ~0.2-µm long structures close to the cell wall (FIG. 3 C, arrow 4). It is suggested here that these structures are invaginations in the cell membranes [C22].

A distinct group of intracellular structures in yeast have spheroid forms and are classified as vacuoles or vesicles. These can be sorted on the basis of their size and their mass density [C23]. Two groups are particularly prominent in the STEM images. The first is composed of dark, round shapes (FIG. 12C, arrow 5), which is assumed to represent lipid droplets known to exist in S. pombe cells [C24]. The measured diameter of 0.35 5 0.08 mm agrees with the reported lipid droplet size [C24, C25] of 0.3250.10 mm. The mass density of lipids is ~0.9 g/cm$^3$ and thus lower than the density of water; this explains the darker appearance of these spheres in the STEM image. A second class of vesicles is brighter than the cytoplasm and has an average diameter of 0.16 5 0.02 mm (FIG. 12C, arrow 6). These are presumably the cores of peroxisomes, which may include a dense crystalloid core consisting of urate oxidase molecules [C26]. Several other spheroid structures with intermediate gray tones (see, for instance, FIG. 12C, arrow 7) can be discerned. Those structures could be lipid vesicles in regions of higher protein density. Some of the gold nanoparticles on the silicon nitride window that were used as aids for focusing the STEM are also visible (arrow 8). This analysis of the STEM image of FIG. 12C shows that the obtained information is consistent with existing knowledge of the (ultra)structure of S. pombe.

Screening of Mutant Cells with Liquid STEM

Figure 13:
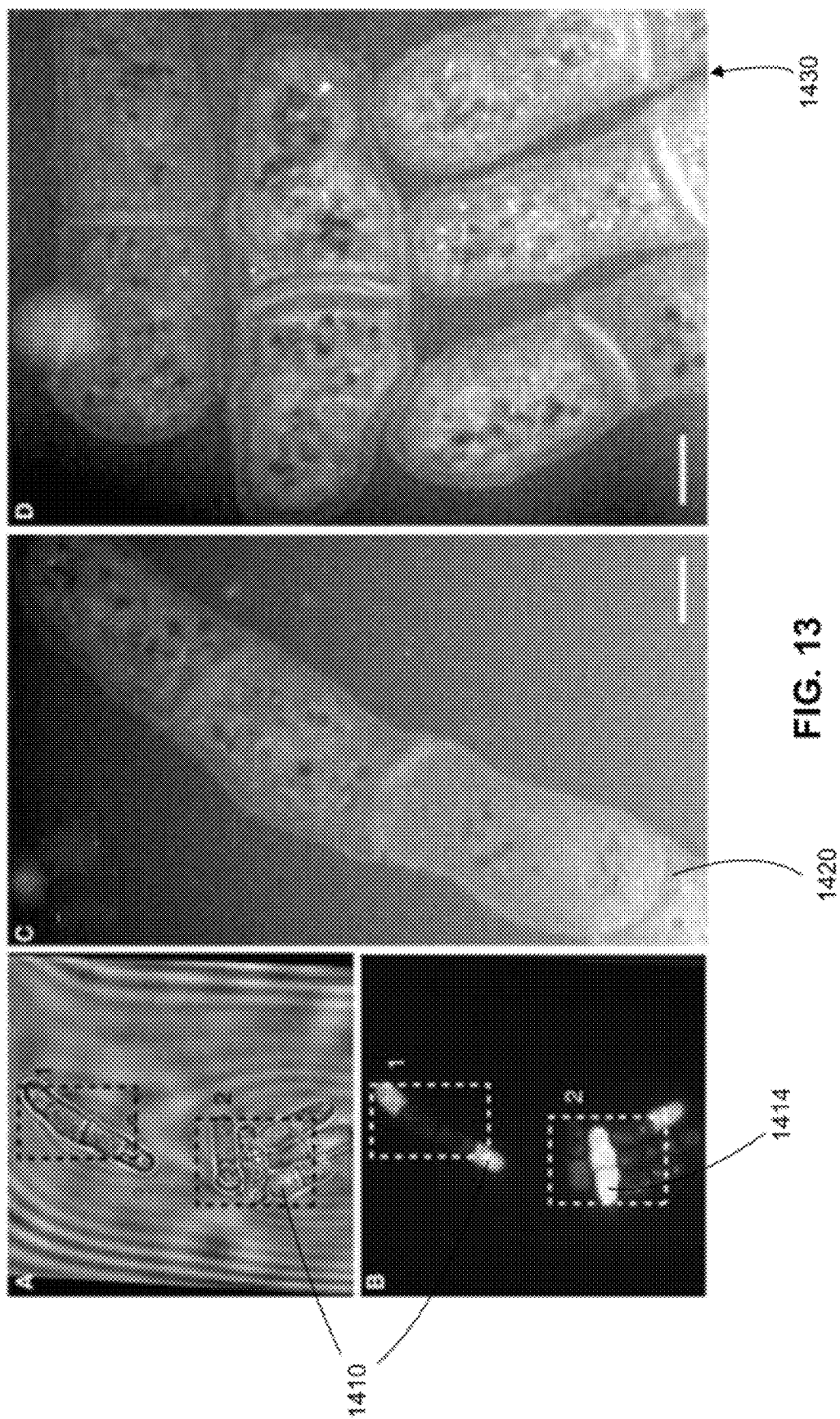
FIG. 13 shows light microscopy and liquid STEM of two Spn3Δ mutants of *S. pombe* [C].

The short sample preparation and imaging time is beneficial for the screening of series of samples, for example, from cells with different mutations. To test STEM for its applicability to screening, cells of three mutants of S. pombe yeast were imaged. FIG. 13 shows light microscopy and liquid STEM of two Spn3Δ mutants of S. pombe. More specifically, FIG. 13 shows (A and B) phase-contrast (A) and fluorescence (B) images of mutant yeast cells 1410. The bright horizontally oriented cell 1414 represents a dead cell, whereas the others are alive. Further, FIG. 13 shows (C) liquid STEM image of an elongated cell 1420 with multiseptal phenotype shown in dashed rectangle 1 in A and B. Further, FIG. 13 shows (D) image of a group of 1430 cells showing the wild-type phenotype, from rectangle 2 in A and B. FIGS. 13A and B display light-microscopy images of the septin mutant spn3Δ. Cells of this mutant are delayed in separation and often grow in chains of typically two to four cell compartments, as seen in the liquid STEM image of FIG. 14C. Several spn3Δ cells that have not developed a multiseptal phenotype are depicted in FIG. 13D. The fluorescence image of FIG. 13B shows both, live cells with punctuated red fluorescence, and a dead cell, the horizontally oriented yeast cell with a bright yellow-green fluorescence.

Figure 14:
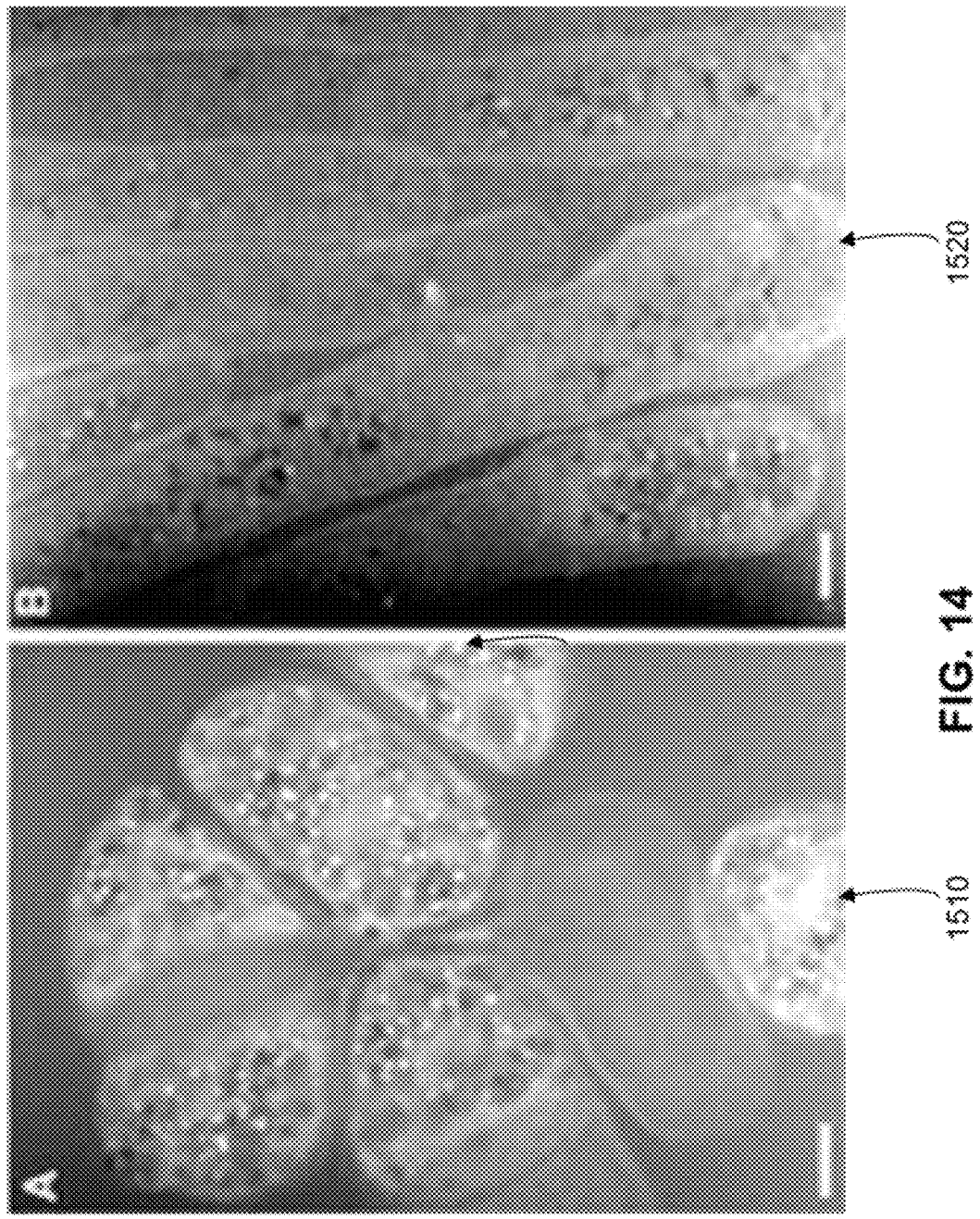
FIG. 14 shows liquid STEM of *S. pombe* mutants [C].

FIG. 14 shows liquid STEM of S. pombe mutants. More specifically, FIG. 14 shows (A) Image of orb6-25 mutant cells 1510. Further, FIG. 14 shows (B) image showing several cells 1520 of the temperature-sensitive mutant cdc25-22 cdc15 (27A). The cells arrest at the G2 phase before entering mitosis and are not able to build septa. This leads to the development of an abnormally elongated phenotype. Cells of another mutant, orb-25, are shown in FIG. 14A. These cells have a disturbed cell polarity displaying isotropic cell growth and a shortened length. In addition, most of these mutants accumulated an abundance of vacuoles compared to the wild-type. A few cells, like the one in the lower half of FIG. 14A, appeared empty of organelles. A temperature-sensitive cdc25-22 cdc15 (27A) mutant was also imaged (FIG. 14B). These studies required only a few hours per mutant, a time that is similar to that needed for light microscopy, and much shorter (hours versus weeks) than what is possible with existing electron microscopy approaches [C7].

Spatial Resolution and Imaging Contrast of STEM of Hydrated Yeast Cells

Figure 15:
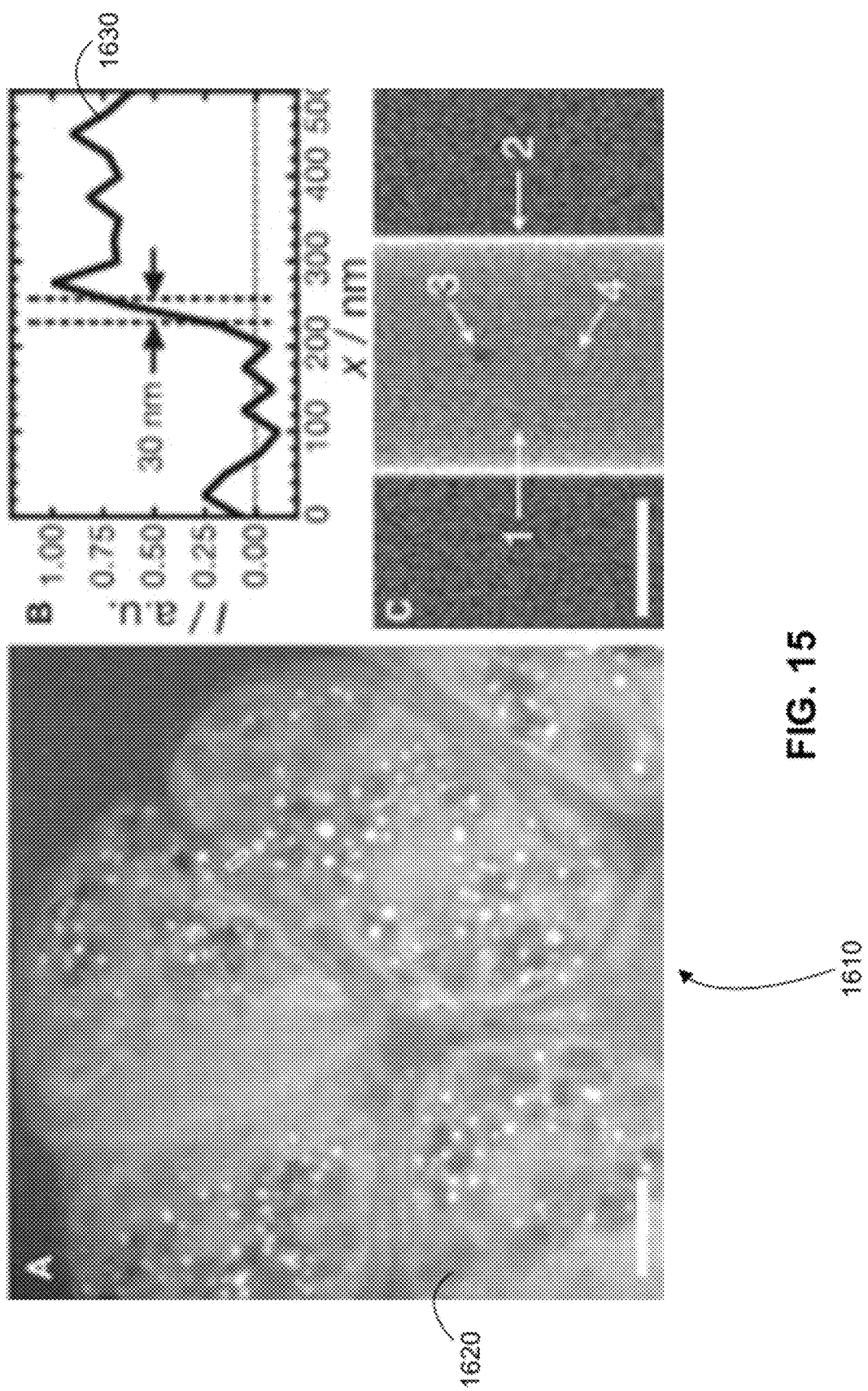
FIG. 15 shows analysis of the spatial resolution of liquid STEM of fully hydrated yeast cells [C].

FIG. 15 shows analysis of the spatial resolution of liquid STEM of fully hydrated yeast cells 1610. More specifically, FIG. 15 shows (A) selected region 1620 of the image recorded of an orb-25 mutant shown in FIG. 14B. Further, FIG. 15 shows (B) Line scan 1630 representing the average intensity, I, versus the position, x, of a 5-pixel-wide line drawn over a sharp edge indicated by an asterisk in A. The 25-75% rising edge width is 30 nm. The signal was normalized to unity at the maximal intensity, and to zero at the intensity of the lower side of the edge. FIG. 15 shows (C) simulated liquid STEM image of a model yeast cell in a water layer. The image is the top view of a simple cell model (arrow 1) consisting of a cylinder (arrow 2 points to the cylinder wall), with one lipid droplet (arrow 3), and one protein vesicle (arrow 4). Scale bars, 2 mm. The maximal spatial resolution in the STEM images of the yeast cells in liquid was determined from FIG. 15 B (orb6-25 mutant), which corresponded to the smallest liquid thickness in the experimental series. FIG. 15A shows a selected region of this image. As a measure of the resolution, the 25-75% rising edge width (27) $r_{25-75}$, applicable has been used because the electron probe size was smaller than the pixel size for the upper ~2 μm of the sample (electron beam sample interactions broadened the probe to values larger than the pixel size of 25 nm for deeper layers [C18]. The average intensity of the 5-pixel-wide line at marker 1 versus position is shown in FIG. 15B. Five of the sharpest edges on elongated structural components in the image resulted in an average $r_{25-75}=32\pm8$ nm, approaching the pixel size of 25 nm. This value of r25-75 represents the maximal achieved resolution in this study on yeast ultrastructure.

The contrast of liquid STEM is determined by the signal/noise ratio observed between pixels recorded at the location of a certain material versus the background signal from the surrounding liquid. This contrast depends on the thickness of the liquid and on the electron density of the object on which the contrast is obtained [C18]. The resolution is given by the minimum size of the object, or the sharpest edge of the object that can be observed above the noise. The larger the difference is between the electron density of a biological material and the electron density of water, the larger the contrast, and hence the higher the resolution. Furthermore, the thinner the liquid, the higher is the resolution. The image of FIG. 12 C has a maximal resolution of 50510 nmon biological ultrastructure, as measured for a line scan over the edge of the dark-appearing vesicle [C5]. Indeed, this sample was thicker than the sample used for FIG. 15. The resolution on the gold nanoparticles is much higher (see FIG. 12C).

There is no simple equation to calculate the resolution, because it depends on the geometry and the composition of the sample. To understand the achieved resolution and contrast, STEM of a model sample has been simulated by Monte Carlo methods [C28, C29]. The sample consisted of a water layer 4 μm thick enclosed between two silicon nitride layers each 50 nm thick, with an outer cylinder radius of 2 μm and a wall thickness of 100 nm, as a simplified model of a yeast cell. As approximation of the cell wall material [C19], glucose with a chemical composition of $H_{10}C_6O_5$ and a mass density of 1.5 g/cm³ was used. The cylinder was filled with water. The cell model further contained a sphere with a diameter of 400 nm placed at a depth of 500 nm in the cell (as seen from the top), with a chemical composition of $H_{98}C_{55}O_6$ and a mass density of 0.92 g/cm³, as a model for lipid droplets [C30]. A vesicle was included as a sphere with a diameter of 400 nm at a depth of 500 nm with the chemical composition and mass density of an average protein of $H_5C_3NO$ and a mass density (31) of 1.3 g/cm³. STEM images were simulated with the same parameters (but with a smaller image size) as used in the experiments, and filtered. The simulated image of FIG. 15C reproduces the basic features of the experimental figures with a comparable contrast level. The cell (arrow 1) is brighter than the surrounding liquid, the wall of the cylinder is visible as a bright line (arrow 2), the lipid droplet is visible as a dark shape (arrow 3), and the vesicle filled with protein can be recognized as a feature with a brighter contrast than its surroundings (arrow 4). Since this simulation reproduces the basic features of the experimental STEM images, one can use such simulations to predict the contrast and resolution for future studies, or to analyze the composition of the materials in the sample.

Discussion

The maximal spatial resolution of STEM achievable on fully hydrated, pristine yeast cells in this initial study was 32±8 nm, which is an order of magnitude better than the ~200-nm resolution of diffraction-limited conventional light microscopy [C32], and around one-sixth of the ~5-nm electron-dose-limited resolution obtainable with TEM in cryo-sections of eukaryotic cells [C7]. Light microscopy is a standard tool for cell biology, but its use is limited for many cell constituents that are smaller than the wavelength of light. Super-resolution microscopy permits visualization of smaller objects but requires fluorescent labeling of specific proteins [C3]. Conventional EM relies on an extensive preparation of the cells through fixation, staining, and sectioning into thin sections (33), and is prone to artifacts. In modern cryo-EM [C6, C7] cells are rapidly frozen at high pressure to convert the cellular water into amorphous ice [C34, C35], sometimes with the help of high concentrations of glass-inducing solutes, thereby avoiding intracellular damage by ice crystals. Thin, peripheral regions of whole cells can be studied, but when the region of interest lies in a part of the cell that exceeds ~0.3 mm of thickness, the cell has to be cryosectioned. The cells are thus not intact, nor alive. Furthermore, sample preparation, imaging, and analysis are highly time-consuming. The intermediate resolution achieved with STEM on hydrated cells, in combination with a sample preparation similar to that for light microscopy, or rather, the absence of EM sample preparation, is potentially of great value for the study of cellular ultrastructure and function.

An important questions associated with each biological EM technique is the effect of radiation damage. The hydrated yeast samples were exposed to $1.4\times10^4$ electrons/scan pixel of a size of 25 nm, which translates into an average electron dose of 22 e⁻/nm². This electron dose is well below the dose limit for EM of wet biological specimens (36), and two orders of magnitude below the electron dose of $2\times10^3$ e⁻/nm² or greater used in cryo-EM [C7]. A particular advantage of imaging at an intermediate resolution between those of light microscopy and cryo-EM is that the radiation dose typically scales with the square of the resolution [C20]. The local electron dose directly in the focal plane has likely been higher, maximally $1 \times 10^4$ e$^-$/nm$^2$ within the diameter of the electron probe containing 50% of the current of 0.9 nm assuming optimal focus at the beam entrance window. However, only a minor portion of a yeast cell was exposed to the higher dose, because electron beam scanning occurred with lines separated by the pixel size of 25 nm, and beam broadening rapidly decreased the intensity for deeper layers (18). In future experiments, the electron probe size could be changed to a value equal to the pixel size, which can be done while maintaining the same image contrast and resolution. The electron dose of 22 e$^-$/nm$^2$ can thus be considered as the dose required to obtain the images shown here.

It is not certain whether the liquid STEM approach can be used for tomography. The liquid specimen holder can be tilted and the geometry of the tapered windows in the microchips allows for tilt angles up to ~35°, which could be used for tomography with a limited axial resolution. However, the recording of a tilt series on pristine cells is problematic, because the cells are not alive after the recording of one STEM image. One future possibility could be to record a series of ~10 images at a low dose, using a special type of specimen stage that allows for rapid tilting with low drift.

These results are believed to represent a new approach in nanoscale microscopy. Pristine cells can now be examined with a resolution of a few tens of nanometers. It is expected that this approach will be useful for research in fields such as cell biology to study questions requiring a spatial resolution better than that achievable with light microscopy, but not yet involving a spatial resolution as high as ~5 nm. This methodology can easily be combined in correlative approaches with other microscopy techniques, to study the location and the function of single proteins within the cellular framework [C2]. Images from both light microscopy and STEM on the same cells in the microfluidic chamber were obtained. The temporal correlation between the images was in the range of a few minutes, but could be reduced to less than a second by the integration of a light microscope into the electron microscope [C37]. In the study, the identification of intracellular organelles was based on structural information (size, shape, and location), and on differences in mass density. Further organelle classification is possible by using specific fluorescent markers for proteins of interest [C38]. STEM could also be combined with superresolution imaging of fluorescent labels to correlate protein locations with <50 nm precision with ultrastructural information of intact cells [C3]. Nanoparticles, like colloidal gold or quantum dots, serving as protein tags could be used for the imaging of specifically labeled surface proteins with a resolution [C14, C39] of ~3 nm. The capability of imaging pristine cells could be combined with the technique to image with a short pulse of electrons, the so-called four-dimensional EM [C40]. This would open the possibility to capture native cellular configurations before radiation-induced effects would have time to propagate through the structure. A burst of short pulses could potentially be used to examine processes of short duration occurring in liquid. It is anticipated that liquid STEM will be broadly applied to explore pristine cells that are living at the onset of imaging, bridging the capabilities of light microscopy and cryo-EM.

Example 8

Nanometer-Resolution Electron Microscopy Through Micrometers-Thick Water Layers

The following text was in part published in [D]. The ultrastructure of cells has traditionally been studied with transmission electron microscopy (TEM) achieving nanometer resolution on stained and epoxy/plastic embedded thin sections, or on cryosections [D1-D3]. Disadvantages are that the cells are not in their native liquid state and not complete. TEM imaging of whole, vitrified cells is possible, but restricted to the very edges of a cell. Ever since the early days of electron microscopy it has been a goal to achieve nanometer resolution on whole cells in liquid [D4]. Two scientific advances from the last decade, the introduction of gold nanoparticles serving as specific protein labels [D5] and the development of silicon nitride membranes used as electron transparent windows in a liquid compartment [D6], have led to the introduction of a novel concept to achieve nanometer resolution on tagged proteins in eukaryotic cells [D7]. A liquid specimen is placed in a micro-fluidic compartment with electron-transparent windows and imaged with a scanning transmission electron microscope (STEM) using the annular dark field (ADF) detector. The contrast mechanism for imaging with the ADF detector is sensitive to the atomic number Z of the specimen [D8], which can be used to image high-Z nanoparticles in thick solid-[D9], or liquid samples [D7]. Nanoparticles specifically attached to proteins [D5] can then be used to study protein distributions in whole cells in liquid [D7], similar as in fluorescence microscopy, where proteins tagged with fluorescent labels are used to study (dynamic) protein distributions in cells [D10].

Is was discovered that the resolution achievable with STEM imaging in liquid depends on the vertical position z of the nanoparticle and on the thickness T of the liquid. Two specimen configurations can be distinguished. (1) The nanoparticles are located in the top layer of the liquid with respect to the electron beam entrance, such that imaging occurs with an unperturbed electron probe. (2) The nanoparticles are at a position z deeper in the liquid for which beam broadening plays a role. The resolution on gold nanoparticles placed above and below water layers with 1.3<To<13 µm, representing a size range from bacterial cells to eukaryotic cells, is measured. A theoretical model of the resolution and present Monte Carlo simulations of the STEM experiments will be described. The Monte Carlo simulations were used to calculate the resolution achievable on gold nanoparticles in the middle of the liquid as function of z for T=5 µm.

Experimental

A series of test samples were imaged with STEM to determine the resolution of imaging gold nanoparticles in a saline water layer. The micro-fluidic compartments for liquid STEM imaging consisted of two silicon microchips supporting silicon nitride windows. The windows had dimensions of 50×200, or 70×200, and 50 nm thickness (Protochips Inc, NC). The microchips were made hydrophilic by coating with poly L-lysine. Gold nanoparticles of average diameters d=1.4, 5, 10, 30, and 100 nm were applied from solution by applying a droplet of about 0.5 ml with a micropipette. Different liquid compartments were made with polystyrene microspheres in the range of 2-10 µm diameter, serving as spacers and thus forming a micrometer-sized gap of defined thickness between the windows. The chips were loaded in the STEM using a fluid specimen holder (Hummingbird Scientific, WA) [D7]. A flow of 10% phosphate buffered saline (PBS) in water with a flow rate of 1-2 µl/min was used. The STEM (CM200, Philips/FEI company, OR) was set to 200 kV, a probe current I=between 0.47 and 0.58 nA (the probe current was different after a tip change; for the calculations the average of 0.53 nA), and a beam semi-angle α=11 mrad was used. Under these conditions the theoretical probe size containing 50% of the current is $d_{50}$=0.5 nm [D11]. The real probe size was estimated to be $d_{50}$=0.6 nm. ADF detector (Fishione Instruments) semi-angles of β=70 and 94 mrad were used. The outer angle $β_2$ was 455 and 611 for β=70 and 94 mrad, respectively (for the Monte Carlo calculations a value of 500 mrad was used). Image processing was done with imageJ. Contrast and brightness were adjusted for maximum visibility and a convolution filter with a kernel of (1, 1, 1; 1, 5, 1; 1, 1, 1) was applied to reduce the noise for the STEM images, while the data analysis via line scans and the resolution determination was performed on the original unfiltered data.

Results and Discussion

STEM Imaging of Gold Nanoparticles on Top of a Water Layer

Figure 16:
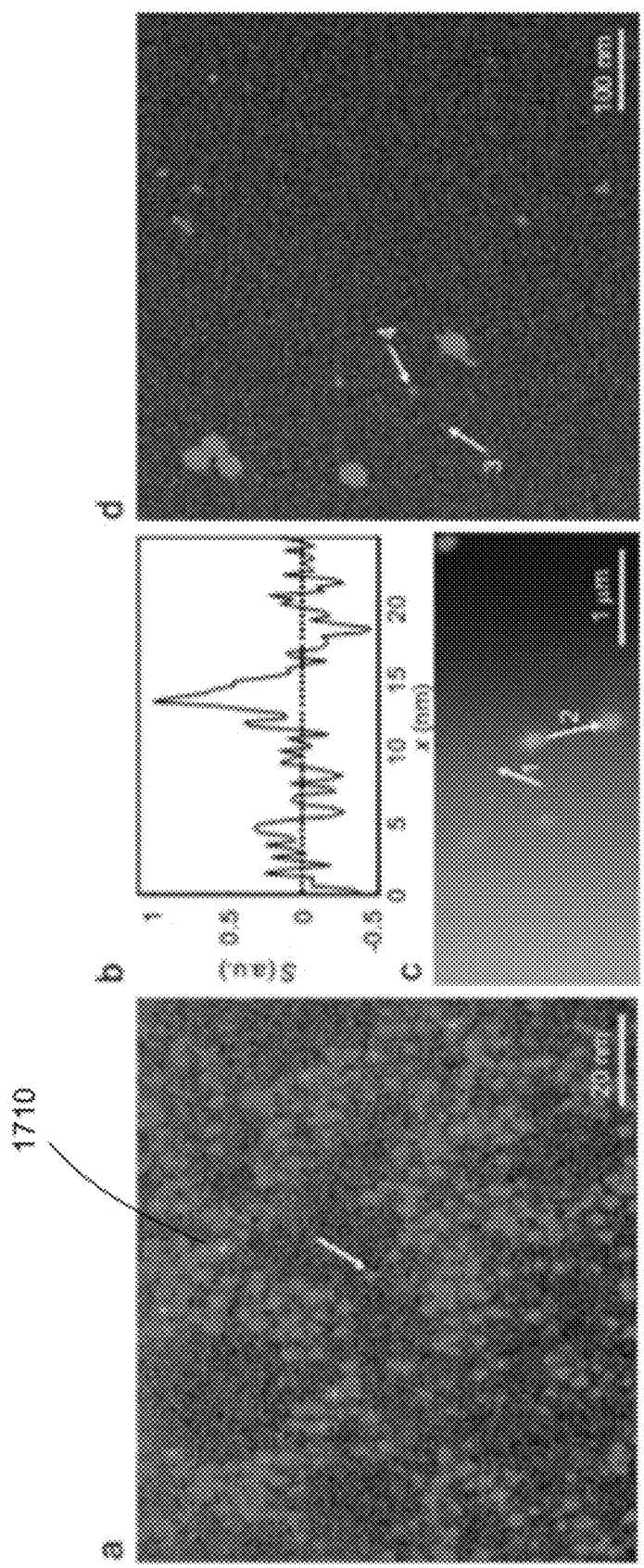
FIG. 16 shows STEM imaging of nanoparticles on top of a water layer [D].

FIG. 16 shows STEM imaging of nanoparticles on top of a water layer. More specifically, FIG. 16 shows (a) image of gold nanoparticles 1710 with an average diameter d=1.4 nm on a liquid with a thickness T=3.3 μm, recorded at a detector semi-angle β=70 mrad, magnification M=480,000, with a pixel size of s=0.29 μm, and a pixel-dwell time of t=20 μs. The signal intensity was color coded. Further, FIG. 16 shows (b) line-scan, signal S versus horizontal position x, over the nanoparticle indicated with the arrow in (a) from the unfiltered data. The dashed line represents the background level. Further, FIG. 16 shows (c) overlay of two images recorded at the same position as (a), but at M=24,000 and with the stage tilted by 24.6° for one image. Arrow #1 connects the shift of 0.54 μm of a nanoparticle with d=30 nm on the top window. Arrow #2 connects a 0.82 μm shift in opposite direction of a nanoparticle with d=100 nm on the bottom window. The arrows are not entirely parallel due to stage drift during tilting. Further, FIG. 16 shows (d) image of a sample with T=13 μm recorded at M=160,000, s=0.87 nm, t=20 μs, and b=94 mrad. Arrow #3 points to a gold nanoparticle of 10 nm and arrow #4 to one of a 5 nm. FIG. 16a shows a STEM image of gold nanoparticles with d=1.4 nm on top of a water layer. The image was recorded at the edge of a 50×200 μm window in a flow cell made with a spacer of 5 μm polystyrene microspheres. For this particular sample the nanoparticles were positioned onto the vacuum side of the window to prevent the particles from dissolving in the liquid during imaging, which occurred at the higher magnifications, here 480,000. Remark that nanoparticles only dissolved in the liquid during imaging at the highest magnification range in this study. The gold nanoparticles are visible as bright yellow spots on a blue background and are individually resolved. Several nanoparticles were selected that were visible above the background noise. A line-scan over one of the smallest nanoparticles (FIG. 16b) had a full-width-at-half-maximum (FWHM) of $d_{FWHM}$=1.5 nm of the peak above the background level. The background level was determined from the average signal of horizontal positions 0-10 nm. The signal-to-noise ratio (SNR) was 5.3, as determined from the ratio of the peak height (the maximal signal—the average of the background signal) and the standard deviation of the background. The average of five of the smallest nanoparticle interfaces gave $d_{FWHM}$=1.2±0.2 nm (the error is the standard deviation) for SNR=5±1. The factor of 5 is consistent with the Rose criterion [12-14] stating that SNR≥5 for pixels to be visible in an image containing background noise. T was calculated to be 3.1 μm from the measured fraction $N/N_0$=0.26 (and using Eq. (1) as described elsewhere [7]). As a second measurement of T, it was recorded an image at a lower magnification, with nanoparticles at the bottom window visible, and an image with the sample tilted by 24.6° (FIG. 16c). From the parallax equation it followed that T=ΔL/sin φ=3.3±0.3 μm. From measurements of 11 different positions on a total of 6 different samples it was found that both methods to determine T were equal within a standard deviation of 20%. The value of 3.3 μm is smaller than the diameter of the polystyrene microspheres of 5 μm used for spacing; presumably compression of the beads and/or deformation of the chips occurred. STEM imaging at the position of a corner of this window resulted in dFWHM=1.0±0.3 nm for SNR=5 and T=1.7 μm.

To study the imaging in thicker water layers, a flow cell was made with 10 mm polystyrene microspheres. Gold nanoparticles of 5, 10 and 30 nm were placed from solution at the liquid side (thus inside the flow cell during STEM imaging) of a 70×200 μm large top window. The 70 μm wide silicon nitride windows were found to bulge outward into the vacuum by a maximum of 3 μm per window (the bulging was 1 μm for the 50 μm wide windows). The liquid STEM image obtained at a position in the middle of the window is shown in FIG. 16d, with T=13 (from $N/N_0$=0.50), from 6 μm total bulging, and compression of the 10 μm microsphere spacer. The images for this sample were recorded at a lower magnification than for FIG. 16a, and the gold nanoparticles, now in contact with the liquid, remained at their positions during imaging. The detector was set to β=94 mrad for optimal visibility of the nanoparticles in the background signal. Gold nanoparticles of d=10 (e.g., at arrow #3) and 30 nm are clearly visible above the noise. At the arrow #4 a smaller nanoparticle is just visible with $d_{FWHM}$=4 nm and SNR=4. The average of 8 of the smallest nanoparticles (some outside the cropped area shown in FIG. 16d) gave $d_{FWHM}$=5±1 nm for SNR=5±1. Further images were recorded with β=94 mrad at the edge of the window of a third sample. The average of 4 of the smallest nanoparticles gave $d_{FWHM}$=3±1 nm for SNR=5. The determined thickness was T=7.5 μm. It was previously demonstrated a resolution of 4 nm for 10 nm gold nanoparticles in the top layer of 7 mm of water [D7], consistent with the results presented here within the error margin. Note that the 20-80% rising edge width $r_{20-80}$ was used in this previous work as measure of the resolution and not the $d_{FWHM}$ because the nanoparticles used in that study were larger (10 nm diameter) than the minimum detectable size, and for that situation the $r_{20-80}$ is the most accurate measure of the resolution [D15].

Theoretically Achievable Resolution of STEM Imaging of Nanoparticles in the Top Layer of a Liquid The number of electrons N scattered into the ADF detector, i.e., by an angle larger than β, is calculated from the partial cross-section for elastic scattering σ(β) as [D15]

$$\frac{N}{N_0} = 1 - \exp\left(-\frac{T}{l(\beta)}\right), l(\beta) = \frac{W}{\sigma(\beta)\rho N_A}, \quad (ED1)$$

with the number of incident electrons N0, mean-free-path length for elastic scattering l(b), mass density r, the atomic weight W and Avogadro's number NA. For the screened Rutherford scattering model based on a Wentzel potential the partial cross-section for elastic scattering is given by [D15]

$$\sigma(\beta) = \frac{Z^2 R^2 \lambda^2 (1 + E/E_0)^2}{\pi a_H^2} \frac{1}{1 + (\beta/\theta_0)^2}; \quad (ED2)$$

$$E_0 = m_0 c^2; \lambda = \frac{hc}{\sqrt{2EE_0 + E^2}}; \theta_0 = \frac{\lambda}{2\pi R}; R = a_H Z^{-1/3}; E = Ue, \quad (ED3)$$

with electron accelerating voltage U (in V), atomic number Z, $a_H$ the Bohr radius, $m_0$ the rest mass of the electron, c the speed of light, h Planck's constant, and e the electron charge. For the gold nanoparticles, $l_{gold}$=73.2 and 122 nm for β=70 and 94 mrad, respectively. From the quadratic average Z of water of $\sqrt{(2/3 \times 12 + 1/3 \times 8^2)}$=4.69 (close to experimental estimates [D16]), it follows that $l_{water}$=10.4 and 18.5 μm, for β=70 and 94 mrad, respectively [D7]. Here, inelastic scattering typically occurring at smaller angles is neglected. Multiple scattering is also neglected.

The value of $d_{FWHM}$ represents the noise-limited resolution for the configuration of nanoparticles in the top layer of the liquid, where the electron probe is smaller than the nanoparticles. The contrast is generated from the difference between the number of detected electrons $N_{signal}$ for a pixel with the electron beam at the position of a nanoparticle and the background signal $N_{bkg}$. Both are given by [D7, D17]

$$\frac{N_{signal}}{N_0} = 1 - \exp\left[-\left(\frac{d}{l_{gold}} + \frac{T-d}{l_{water}}\right)\right], \quad (ED4)$$

$$\frac{N_{bkg}}{N_0} = 1 - \exp\left[-\frac{T}{l_{water}}\right]$$

Following the same definition of the SNR as used for the experimental data, assuming 100% detection efficiency, assuming $N_{signal} \approx N_{bkg}$, and assuming Poisson statistics the SNR can be approximated by $$SNR = \frac{N_{signal} - N_{bkg}}{\sqrt{N_{bkg}}} \quad (ED5)$$

Figure 17:
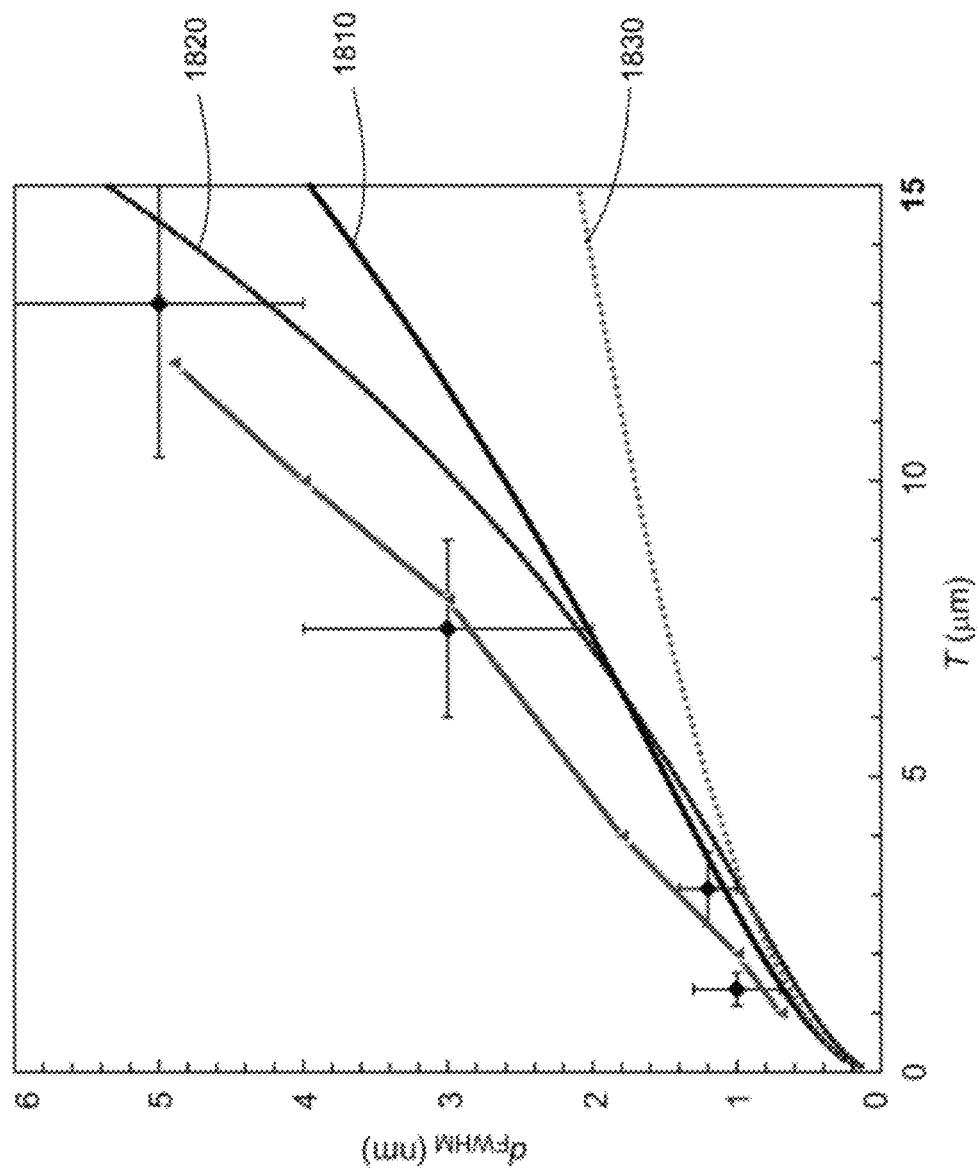
FIG. 17 shows resolution of STEM in the top layer of a liquid, $d_{FWHM}$ as function of T[D].

The SNR should be at least 5 to be able to detect one pixel in a noisy image [D12-D14]. Eq. (ED5) was solved numerically (Mathematica, Wolfram Research, Inc.) for 6.6×10⁴ electrons per pixel yielding d, the smallest nanoparticle visible for SNR=5 [D12]. FIG. 17 shows that the calculated resolution is somewhat higher (values of d lower) than the experimental resolution. Yet, the values agree within the experimental error margin, except for a small mismatch at the largest water thickness. From this agreement it can be concluded that the model of a noise-limited resolution is valid and that inelastic scattering and multiple scattering can be neglected for the STEM imaging of gold nanoparticles on top of a water layer of several micrometers thickness. The thicker liquids are preferentially imaged with β=94 mrad, while there is no preference for either 70, or 94 mrad for T<~7 μm. The calculation can possibly be improved by using a more precise model for scattering than the Rutherford model. An analytic expression of the resolution can be derived for T<<$l_{water}$ and d<<$l_{gold}$, such that the Taylor expansion of Eq. (ED5) yields $$d = 5l_{gold}\sqrt{\frac{T}{N_0 l_{water}}} \quad (ED6)$$

Note that a different definition of the SNR was used in the previous work [D7], resulting in a factor of $\sqrt{2}$ larger values of d obtained with Eq. (ED6). As can be seen in FIG. 16d Eq. (ED6) fits the experimental data for smaller T, but becomes inaccurate for T>¼ $l_{water}$. This equation may serve as a first estimate of the noise-limited resolution of STEM on heavy nanoparticles on a thick layer of a light material.

Electron Dose

For biological applications the electron dose should be taken into account. Most images were recorded at magnifications≤160,000 for which the pixel size was 0.87 nm or smaller. With $d_{50}$=0.6 nm and a pixel time of 20 μs, the electron dose was approximately 1.0×10⁵ electrons/nm², which is a factor of 4 smaller than the limit of radiation damage used for conventional thin sections containing fixed cells [D18], an order of magnitude larger than the radiation limit used for the imaging of cells in cryosections [D19], and two orders of magnitude larger than the radiation limit used for single particle tomography on samples in amorphous ice [D20]. The radiation limits for STEM imaging in liquid are not yet determined; it was found a dose of 7.0×10⁴ electrons/nm² to be compatible with the imaging of gold nanoparticles used as molecular labels on fixed cells in flowing saline water [D7]. For the highest magnifications used in this study, i.e., FIG. 2a with 480,000, the pixel size was 0.3 nm, considerably smaller than $d_{50}$, and thus the electron dose for those experiments was 8.0×10⁵ electrons/nm², too high even for conventional thin sections. It was found nanoparticles to dissolve in the liquid at this electron dose, while they remained on their support for the electron dose of 1.0×10⁵ electrons/nm².

From Eq. (ED6) follows that the achievable resolution depends via N0 on the specific radiation limit of the sample under investigation. In case the pixel size is larger than the probe size, the settings of the microscope can be optimized to achieve a reduced electron dose by increasing the probe size of the STEM via either increasing, or decreasing the semi-angle of the electron probe. A second way to optimize for low-dose imaging is by applying noise filtering, and/or using pattern recognition, such that nanoparticles can be discerned from the noise background with a lower electron dose than needed on the basis of the Rose criterion [D12]. It should also be noted that regions of the sample positioned deeper in the liquid will be imaged with a broadened probe (see below) and thus with a lower electron dose.

Monte Carlo Simulations

As additional evaluation of the achievable resolution in liquid Monte Carlo calculations were used to simulate electron trajectories for given irradiation schemes and sample geometries. The Monte Carlo calculations have the advantage over the analytical model presented in the above of including beam blurring and multiple scattering. The calculation model was based on the software CASINO [D21], modified to simulate STEM optics, including a conical electron beam, Poisson statistics of the electron source, and the ADF detector. The total elastic scattering cross-section was determined using the software ELSEPA [D22]. A model sample was programmed containing gold nanoparticles of diameters 0.8-10 nm on top of water layers with T=1-12 μm, enclosed between two sheets of silicon nitride of 50 nm thickness each. For each water thickness line scans were simulated over the nanoparticles, with a pixel size of 0.1 nm and 6.6×10⁴ electrons per pixel, from which the smallest nanoparticles visible with SNR=5±1 were determined as measure of the resolution. The FWHM values were determined for those nanoparticles as measure of the resolution. The detection efficiency was assumed to be 100%. The semi-angle of the ADF detector was set to a value of β=94 mrad. FIG. 17 shows resolution of STEM in the top layer of a liquid, $d_{FWHM}$ as function of T. The experimental data is compared with numerical calculations for β=94 mrad detector angle 1810 and β=70 mrad 1820, with an analytic model for β=94 mrad 1830, and with minimum observable d determined with Monte Carlo simulations for β=94 mrad 1840. FIG. 17 shows a good agreement of the resolution values obtained with the Monte Carlo simulations with those from the experimental data. The Monte Carlo calculations confirm the capability of liquid STEM to achieve nanometer resolution on gold nanoparticles in water layers with thicknesses in the micrometer range.

STEM Imaging of Gold Nanoparticles Below a Water Layer

The imaging of nanoparticles below a liquid layer takes place with an electron probe broadened by electron-sample interactions and it is thus not correct to assume that the resolution is noise limited. In case the probe is broadened to a width larger than the size of the nanoparticles the electron probe limits the resolution. Two point objects imaged by a Gaussian probe with $d_{FWHM}$ and spaced by $1.14 d_{FWHM}$ would result in a line scan with two peaks and a 20% signal dip in their middle, which is the Raleigh criterion of resolution. As lower limit of the resolution the $d_{FWHM}$ has thus been used. The resolution below the liquid was measured for 8 different positions with varying T on 4 samples containing gold nanoparticles with d=5, 10, 30, and 100 nm. The value of T was determined from the average result of the two methods described above, i.e., tilting the specimen and measuring the detector current. FIG. 18 shows STEM imaging of gold nanoparticles below a water layer. More specifically FIG. 18 shows (a) image of gold nanoparticles of d=5, 10, 30 nm below a water layer of T=1.3 µm, recorded with β=94 mrad, M=160,000, s=0.87 nm, and t=20 µs. The signal intensity was color coded. Arrows #1, #2, and #3 point to nanoparticles with respective diameters of 10, 5 and 30 nm. Further, FIG. 18 shows (b) line-scan over the nanoparticle at the arrow #2 in (a) of the unfiltered data. Further, FIG. 18 shows (c) Resolution as function of T. Experimental data is compared with a numerical calculation 1910, with an analytic expression 1920, and with Monte Carlo simulations 1930. The resolution versus the vertical position of nanoparticles in the liquid z for T=5 µm from Monte Carlo calculations 1940 is also included (here the horizontal axis represents z). FIG. 18*a* shows several gold nanoparticles at the bottom of a 1.3 µm thick liquid layer (the same data used for this figure was used for the supporting information in [D7]). Arrow #1 points to a nanoparticle with d=10 nm. A smaller nanoparticle is visible at arrow #2, presumably with d=5 nm exhibiting $d_{FWHM}$=8 nm in the line scan shown in FIG. 18*b*. The average of 4 small nanoparticles gave $d_{FWHM}$=9±1 nm. The nanoparticle at arrow #3 has d=30 nm and the signal intensity is clipped. The background signal varies within the image (see e.g. the increased scattering at the right upper corner) due to the bulged silicon nitride windows, leading to a changing water thickness as function of the lateral position. The $d_{FWHM}$ is plotted as function of T for all 8 samples in FIG. 18*c*.

Calculation of the Beam Broadening

The broadening of the electron probe due to beam-sample interactions can be calculated from the elastic scattering cross-section [D15]. In a simplified model, it is assumed that all blurring occurs as single scattering event in the middle of the sample at Z=T/2 [23]. Electron probe broadening then follows from the unscattered fraction of the electron probe $$\frac{N_{not-scattered}}{N_0} \cong \exp\left(-\frac{T/2}{l(\beta)}\right) \qquad (ED7)$$

The angle containing a certain fraction of the current translates to a probe diameter as d=2(T/2)β. In the original papers [D23, D24] the $d_{90}$ (the diameter containing 90% of the current) was used to represent the resolution in X-ray analysis of elements in a thin foil. Also, Monte Carlo based estimation methods of the beam broadening used the $d_{90}$ [D25]. However, for STEM imaging the $d_{90}$ is an inaccurate measure of the resolution, because it is dominated by the beam tails formed by infrequent high-angle scattering events [D26]. The high-resolution electron probe is maintained on a background signal formed by the beam tails, as discussed also for the imaging in vapor with a scanning electron microscope [D27]. For this study it is used the $d_{25}$ in solving Eq. (ED7). FIG. 18*c* shows agreement of the theoretical model of $d_{25}$ with the experimental data within the error margin. It should be noted that the contribution of the beam divergence [D24] was neglected here, because the probe diameter in vacuum was much smaller than the $d_{25}$ for T in the experiment. FIG. 18*c* also shows that for T<1 µm the use of $d_{25}$ as measure of the broadening is not accurate. In this thickness regime a transition occurs from the resolution being limited by noise to being limited by beam broadening. For T>2 µm the solution of Eq. (ED7) can be approximated by (FIG. 18*c*):

$$d_{25} = 1.2 \times 10^3 T^{3/2} \frac{Z}{U} \sqrt{\frac{\rho}{W}} \qquad (ED8)$$

This equation is similar as the 25-75% edge width for beam blurring derived by others [D15].

The resolution of STEM imaging on gold nanoparticles below a water layer is also calculated with Monte Carlo simulations using β=94 mrad. For water thicknesses between 0.1 and 8 µm the smallest nanoparticles with a SNR=5±1 were determined. For the larger water thicknesses it was found that the FWHM of a peak at the position of a nanoparticle was much larger than its diameter, demonstrating the beam broadening effect. FIG. 18*c* shows that the values of $d_{FWHM}$ match within a factor of two with the experimental results. The results here are compared with studies of others on polymer films coated with nanoparticles. 200 KV STEM images of 6.4 nm diameter gold nanoparticles at the bottom of a film with a thickness of 1.1±0.1 mm exhibited a FWHM=9±3 nm [D26], similar to the value that was measured for water. In another study, performed with a 300 kV STEM, gold nanoparticles of a diameter of 50 nm were visible below a 4 mm thick nanocomposite polymer filled with carbon black [D28].

Resolution as Function of the Vertical Position of Nanoparticles

Since the Monte Carlo simulations agree with the STEM experiments one can use the Monte Carlo method to predict the achievable resolution for various sample geometries and materials. An important question is how the resolution changes with the vertical position of the nanoparticle in the liquid. The resolution was determined for gold nanoparticles in a water layer with T=5 µm, representative for the imaging of thin eukaryotic cells. FIG. 18*c* shows the resolution as function of z. The resolution is noise limited at z=0 µm. For 0<z<4 µm the effect of beam broadening increasingly influences $d_{FWHM}$. For z≥4 µm $d_{FWHM}$ follows the same curve as the Monte Carlo calculation of the resolution obtained on nanoparticles below the liquid. A resolution better than 10 nm can be achieved for the top 1 mm of the specimen. The resolution achieved on nanoparticles positions deeper in the liquid can possibly be improved by applying deconvolution algorithms, by using particle recognition techniques, and by simply turning the specimen holder by 180° to image the specimen from the other side.

CONCLUSIONS

It is determined that the resolution obtained on gold nanoparticles in the top layer of water is noise limited. The smallest nanoparticles in this study had diameters of 1.4 nm and were visible above the noise for water thicknesses of up to 3.3 µm. The imaging of nanoparticles below micrometers of water is limited by electron probe broadening. Analytic models and Monte Carlo simulations agreed with the experimental data within the error margin. The equations for the resolution provided here are generally applicable to other materials than water and gold. Considering that individual proteins have sizes in the range of several nanometers, it seems feasible to study protein distributions in cells with over an order of magnitude higher resolution than recently developed nanoscopy techniques [D29]. STEM imaging can also be used to study whole vitrified cells with labeled proteins, thus avoiding the often-difficult step of sectioning. Further applications can be found in materials science to study the interaction of solid:liquid interfaces at the nanoscale [D30] in, e.g., micro-batteries, or fuel cells.

Various aspects of the subject matter described herein are set forth, for example and without limitation, in the following numbered clauses:

1. A microfluidic chamber containing a sub-chamber with electron transparent windows and of a thickness sufficiently small to allow electron beam transmission through the sub-chamber, and containing at least one larger sub-chamber for the placement of a living cell.
2. The microfluidic chamber of item 1 being connected to a flow system to provide exchange of the liquid in the sample region.
3. The microfluidic chamber of item 1 made from two silicon microchips with silicon nitride windows.
4. A silicon microchip, forming a part of the microfluidic chamber of item 1, containing an electron transparent window and located at the main surface of the microchip, and an open channel being manufactured in the surface sufficiently large to contain at least one living cell.
5. Placement of the microfluidic chamber of item 1 in a specimen holder for electron microscopy and providing liquid tubing to liquid handling equipment outside of the microscope. Liquid handling equipment including means to provide nutrients to biological cells, control the temperature, inject chemicals in the liquid.
6. A method of immobilize live cells on a second microchip in such way that the main body of the cell fits within the microchip of item 4.
7. A method of imaging a live cell in the microfluidic chamber of item 1 with scanning transmission electron microscopy STEM, by placing the microfluidic chamber in the microscope, moving the microfluidic chamber to the position of the electron beam, exposing the cells to the electron beam, and recording an image formed by the contrast obtained from the interaction of the electron beam with the samples.
8. A method of recording both light microscopy and electron microscopy images of the thin regions of the cells in the microfluidic chamber of item 1, and correlating their information.
9. A method of identifying specific molecules in the images of items 8 or 9, by introducing molecules into the cells by using endocytosis.
10. A method of live cell electron microscopy by recording a single image of a live cell in the microfluidic chamber of item 1 with an electron dose sufficiently low to prevent radiation damage to the biological structure to occur during the recording of the image. The resulting image will then represent the natural structure of the cell.
11. A method of live cell electron microscopy by recording at a series of images with light microscopy and at least one image with electron microscopy of a live cell in the microfluidic chamber of item 1, with the light intensity sufficiently small to keep the cell viable, and the electron dose sufficiently low to prevent radiation damage to the biological structure to occur during the recording of the electron microscope image. The light microscopy images can then be used to study a dynamic process, while the electron microscope image will represent the natural structure of the cell.
12. The above items 1-11 are also applicable for the imaging non-biological objects.
13. The disclosure of items 1-5 can also be used in combination with other forms of microscopy, such as X-ray microscopy.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended items rather than the foregoing description and the exemplary embodiments described therein.

LIST OF REFERENCES

[1] J. Lippincott-Schwartz, E. Snapp, and A. Kenworthy, "Studying protein dynamics in living cells," Nature Reviews 2, 444-456 (2001).
[2] S. W. Hell, "Far-field optical nanoscopy," Science 316, 1153-1158 (2007).
[3] E. Betzig, G. H. Patterson, R. Sougrat et al., "Imaging intracellular fluorescent proteins at nanometer resolution," Science 313, 1642-1645 (2006).
[4] N de Jonge, R. Dona, and S. J. Pennycook, USA (2006).
[5] E. A. Ring and N. de Jonge, "Microfluidic system for transmission electron microscopy," Microscopy and Microanalysis 16, 622-629 (2010).
[6] N. de Jonge, D. B. Peckys, G. J. Kremers et al., "Electron microscopy of whole cells in liquid with nanometer resolution," Proc. Natl. Acad. Sci. 106, 2159-2164 (2009).
[7] N. de Jonge, R. Sougrat, B. M. Northan et al., "Three-dimensional scanning transmission electron microscopy of biological specimens," Microsc Microanal 16 (1), 54-63 (2010).
[8] M. F. Hohmann-Marriott, A. A. Sousa, A. A. Azari et al., "Nanoscale 3D cellular imaging by axial scanning transmission electron tomography," Nat Methods 6 (10), 729-731 (2009).
[9] N. de Jonge, N. Poirier-Demers, H. Demers et al., "Nanometer-resolution electron microscopy through micrometers-thick water layers," Ultramicroscopy 110 (9), 1114-1119.
[10] O. H. Kwon and A. H. Zewail, "4D electron tomography," Science 328 (5986), 1668-1673.
[11] Ring, E. A., Peckys, D. B., Dukes, M. J., Baudoin, J. P. & de Jonge, N., Silicon nitride windows for electron microscopy of whole cells. J. Microscopy 243, 273-283, 2011.

[12] Ring, E. A. & de Jonge, N., Microfluidic system for transmission electron microscopy. Microsc. Microanal. 16, 622-629, 2010.

[A] de Jonge, N. & Ross, F. M., Electron microscopy of specimens in liquid. Nature Nanotechnology 6,695-704, 2011.

[A1] Ruska, E. Beitrag zur uebermikroskopischen Abbildungen bei hoeheren Drucken. Kolloid Z. 100, 212-219 (1942).

[A2] Thiberge, S. et al. Scanning electron microscopy of cells and tissues under fully hydrated conditions. Proc. Natl. Acad. Sci. USA 101, 3346-3351 (2004).

[A3] Williamson, M. J., Tromp, R. M., Vereecken, P. M., Hull, R. & Ross, F. M. Dynamic microscopy of nanoscale cluster growth at the solid-liquid interface. Nature Mater. 2, 532-536 (2003).

[A4] de Jonge, N., Peckys, D. B., Kremers, G. J. & Piston, D. W. Electron microscopy of whole cells in liquid with nanometer resolution. Proc. Natl. Acad. Sci. USA 106, 2159-2164 (2009).

[A5] Huang, J. Y. et al. In situ observation of the electrochemical lithiation of a single SnO2 nanowire electrode. Science 330, 1515-1520 (2010).

[A6] Zheng, H. et al. Observation of single colloidal platinum nanocrystal growth trajectories. Science 324, 1309-1312 (2009).

[A7] Ruska, E. The development of the electron microscope and of electron microscopy. Nobel Lectures, Physics 1981-1990 (1986).

[A8] Reimer, L. & Kohl, H. Transmission Electron Microscopy: Physics of Image Formation (Springer, 2008).

[A9] Bozzola, J. J. & Russell, L. D. Electron Microscopy (Jones and Bartlett, 1992).

[A10] von Ardenne, M. Ueber eun 200 kV-Universal-Elektronenmikroskop mit Objektabschattungsvorrichtung. Z. Phys. 117, 657-688 (1941).

[A11] Donnelly, S. E. et al. Ordering in a (uid inert gas con!ned by (at surfaces. Science 296, 507-510 (2002).

[A12] Parsons, D. F., Matricardi, V. R., Moretz, R. C. & Turner, J. N. Electron microscopy and diffraction of wet unstained and unfixed biological objects. Adv. Biol. Med. Phys. 15, 161-270 (1974).

[A13] Helveg, S. et al. Atomic-scale imaging of carbon nanofibre growth. Nature 427, 426-429 (2004).

[A14] Dai, L. L., Sharma, R. & Wu, C. Y. Self-assembled structure of nanoparticles at a liquid-liquid interface. Langmuir 21, 2641-2643 (2005).

[A15] Danilatos, G. D. & Robinson, V. N. E. Principles of scanning electron microscopy at high specimen pressures. Scanning 18, 75-78 (1979).

[A16] Stokes, D. J. Recent advances in electron imaging, image interpretation and applications: environmental scanning electron microscopy. Phil. Trans. R. Soc. Lond. A 361, 2771-2787 (2003).

[A17] Stokes, D. L. Principles and Practice of Variable Pressure/Environmental Scanning Electron Microscopy (VP-SEM) (Wiley, 2008).

[A18] Abrams, I. M. & McBain, J. W. A closed cell for electron microscopy. J Appl. Phys. 15, 607-609 (1944).

[A19] Daulton, T. L., Little, B. J., Lowe, K. & Jones-Meehan, J. In situ environmental cell—transmission electron microscopy study of microbial reduction of chromium(VI) using electron energy loss spectroscopy. Microsc. Microanal. 7, 470-485 (2001).

[A20] Nishijima, K., Yamasaki, J., Orihara, H. & Tanaka, N. Development of microcapsules for electron microscopy and their application to dynamical observation of liquid crystals in transmission electron microscopy. Nanotechnology 15, S329-S332 (2004).

[A21] Mohanty, N., Fahrenholtz, M., Nagaraja, A., Boyle, D. & Berry, V. Impermeable graphenic encasement of bacteria. Nano Lett. 11, 1270-1275 (2011).

[A22] Grogan, J. M. & Bau, H. H. The nanoaquarium: a platform for in situ transmission electron microscopy in liquid media. J.!Microelectromech. Syst. 19, 885-894 (2010).

[A23] Franks, R. et al. A study of nanomaterial dispersion in solution by wet-cell transmission electron microscopy. J. Nanosci. Nanotechnol. 8, 4404-4407 (2008).

[A24] Liu, K. L. et al. Novel microchip for in situ TEM imaging of living organisms and bio-reactions in aqueous conditions. Lab Chip 8, 1915-1921 (2008).

[A25] Ring, E. A. & de Jonge, N. Microfluidicsystem for transmission electron microscopy. Microsc. Microanal. 16, 622-629 (2010).

[A26] de Jonge, N., Poirier-Demers, N., Demers, H., Peckys, D. B. & Drouin, D. Nanometer-resolution electron microscopy through micrometers-thick water layers. Ultramicroscopy 110, 1114-1119 (2010).

[A27] Peckys, D. B., Veith, G. M., Joy, D. C. & de Jonge, N. Nanoscale imaging of whole cells using a liquid enclosure and a scanning transmission electron microscope. PLoS One 4, e8214 (2009).

[A28] Creemer, J. F. et al. Atomic-scale electron microscopy at ambient pressure. Ultramicroscopy 108, 993-998 (2008).

[A29] Creemer, J. F. et al. A MEMS reactor for atomic-scale microscopy of nanomaterials under industrially relevant conditions. J. Microelectromech. Syst. 19, 254-264 (2010).

[A30] Kawasaki, T., Ueda, K., Ichihashi, M. & Tanji, T. Improvement of windowed type environmental-cell transmission electron microscope for in situ observation of gas-solid interactions. Rev. Sci. Instr. 80, 113701-113705 (2009).

[A31] Klein, K. L., Anderson, I. M. & de Jonge, N. Transmission electron microscopy with a liquid (ow cell. J. Microsc. 242, 117-123 (2011).

[A32] Zheng, H., Claridge, S. A., Minor, A. M., Alivisatos, A. P. & Dahmen, U. Nanocrystal diffusion in a liquid thin film observed by in!situ transmission electron microscopy. Nano Lett. 9, 2460-2465 (2009).

[A33] Nishiyama, H. et al. Atmospheric scanning electron microscope observes cells and tissues in open medium through silicon nitride film. J. Struct. Biol. 169, 438-449 (2010).

[A34] Inami, W., Nakajima, K., Miyakawa, A. & Kawata, Y. Electron beam excitation assisted optical microscope with ultra-high resolution. Opt. Express 18, 12897-12902 (2010).

[A35] Evans, J. E., Jungjohann, K. L., Browning, N. D. & Arslan, I. Controlled growth of nanoparticles from solution with in situ liquid transmission electron microscopy. Nano Lett. 11, 2809-2813 (2011).

[A36] SalI, A., Glaeser, R., Earnest, T. & Baumeister, W. From words to literature in structural proteomics. Nature 422, 216-225 (2003).

[A37] Stahlberg, H. & Walz, T. Molecular electron microscopy: state of the art and current challenges. ACS Chem. Biol. 3, 268-281 (2008).

[A38] Pierson, J., Sani, M., Tomova, C., Godsave, S. & Peters, P. J. Toward visualization of nanomachines in their native cellular environment. Histochem. Cell. Biol. 132, 253-262 (2009).

[A39] Kirk, S. E., Skepper, J. N. & Donald, A. M. Application of environmental scanning electron microscopy to determine biological surface structure. J. Microsc. 233, 205-224 (2009).

[A40] Collins, S. P. et al. Advantages of environmental scanning electron microscopy in studies of microorganisms. Microsc. Res. Techniq. 25, 398-405 (1993).

[A41] Bogner, A., Thollet, G., Basset, D., Jouneau, P. H. & Gauthier, C. Wet STEM: A new development in environmental SEM for imaging nano-objects included in a liquid phase. Ultramicroscopy 104, 290-301 (2005).

[A42] Xiao, Y., Patolsky, F., Katz, E., Hainfeld, J.$F. & Willner, I. 'Plugging into enzymes': nanowiring of redox enzymes by a gold nanoparticle. Science 299, 1877-1881 (2003).

[A43] Barshack, I. et al. A novel method for 'wet' SEM. Ultrastruct. Pathol. 28, 29-31 (2004).

[A44] Melo, R. C., Sabban, A. & Weller, P. F. Leukocyte lipid bodies: in(ammationrelated organelles are rapidly detected by wet scanning electron microscopy. J. Lipid. Res. 47, 2589-2594 (2006).

[A45] Sugi, H. et al. Dynamic electron microscopy of ATP-induced myosin head movement in living muscle !laments. Proc. Natl. Acad. Sci. USA 94, 4378-4392 (1997).

[A46] Matricardi, V. R., Moretz, R. C. & Parsons, D. F. Electron diffraction of wet proteins: catalase. Science 177, 268-270 (1972).

[A47] Lippincott-Schwartz, J. & Manley, S. Putting super-resolution fluorescence microscopy to work. Nature Methods 6, 21-23 (2009).

[A48] Peckys, D. B. & de Jonge, N. Visualization of gold nanoparticle uptake in living cells with liquid scanning transmission electron microscopy. Nano Lett. 11, 1733-1738 (2011).

[A49] Peckys, D. B., Mazur, P., Gould, K. L. & de Jonge, N. Fully hydrated yeast cells imaged with electron microscopy. Biophys. J. 100, 2522-2529 (2011).

[A50] Murai, T. et al. Low cholesterol triggers membrane microdomain-dependent CD44 shedding and suppresses tumor cell migration. J. Biol. Chem. 286, 1999-2007 (2011).

[A51] Dukes, M. J., Peckys, D. B. & de Jonge, N. Correlative fluorescence microscopy and scanning transmission electron microscopy of quantum-dot-labeled proteins in whole cells in liquid. ACS Nano 4, 4110-4116 (2010).

[A52] Radisic, A., Vereecken, P. M., Hannon, J. B., Searson, P. C. & Ross, F. M. Quantifying electrochemical nucleation and growth of nanoscale clusters using real-time kinetic data. Nano Lett. 6, 238-242 (2006).

[A53] Scharifker, B. R. & Hills, G. J. Theoretical and experimental studies of multiple nucleation. Electrochim. Acta 28, 879-889 (1983).

[A54] Radisic, A., Ross, F. M. & Searson, P. C. In situ study of the growth kinetics of individual island electrodeposition of copper. J. Phys. Chem. B 110, 7862-7868 (2006).

[A55] Radisic, A., Vereecken, P. M., Searson, P. C. & Ross, F. M. The morphology and nucleation kinetics of copper islands during electrodeposition. Surf. Sci. 600, 1817-1826 (2006).

[A56] Wise, M. E., Biskos, G., Martin, S. T., Russell, L. M. & Buseck, P. R. Phase transitions of single salt particles studied using a transmission electron microscope with an environmental cell. Aerosol. Sci. Tech. 39, 849-856 (2005).

[A57] Gai, P. L. Development of wet environmental TEM (wet-ETEM) for in situ studies of liquid-catalyst reactions on the nanoscale. Microsc. Microanal. 8, 21-28 (2002).

[A58] Gai, P. L. & Harmer, M. A. Surface atomic defect structures and growth of Au nanorods. Nano Lett. 2, 771-774 (2002).

[A59] Gabrisch, H., Kjeldgaard, L., Johnson, E. & Dahmen, U. Equilibrium shape and interface roughening of small liquid Pb inclusions in solid A1. Acta Mater. 49, 4259-4269 (2001).

[A60] Ross, F. M., Tersoff, J. & Reuter, M. C. Sawtooth faceting in silicon nanowires. Phys. Rev. Lett. 95, 146104 (2005).

[A61] Eswaramoorthy, S. K., Howe, J. M. & Muralidharan, G. In!situ determination of the nanoscale chemistry and behavior of solid-liquid systems. Science 318, 1437-1440 (2007).

[A62] Lee, J. G. & Mori, H. In situ observation of alloy phase formation in nanometersized particles in the Sn—Bi system. Philos. Mag. 84, 2675-2686 (2004).

[A63] Howe, J. M. & Saka, H. In!situ transmission electron microscopy studies of the solid-liquid interface. MRS Bull. 29, 951-957 (2004).

[A64] Kuwabata, S., Kongkanand, A., Oyamatsu, D. & Torimoto, T. Observation of ionic liquid by scanning electron microscope. Chem. Lett. 35, 600-601 (2006).

[A65] Roy, P., Lynch, R. & Schmuki, P. Electron beam induced in vacuo Ag deposition on TiO2 from ionic liquids. Electrochem. Comm. 11, 1567-1570 (2009).

[A66] Joy, D. C. & Joy, C. S. Scanning electron microscope imaging in liquids—some data on electron interactions in water. J. Microsc. 221, 84-99 (2005).

[A67] Hyun, J. K., Ercius, P. & Muller, D. A. Beam spreading and spatial resolution in thick organic specimens. Ultramicroscopy 109, 1-7 (2008).

[A68] Loos, J. et al. Electron tomography on micrometer-thick specimens with nanometer resolution. Nano Lett. 9, 1704-1708 (2009).

[A69] Demers, H., Poirier-Demers, N., Drouin, D. & de Jonge, N. Simulating STEM imaging of nanoparticles in micrometers-thick substrates. Microsc. Microanal. 16, 795-804 (2010).

[A70] Sousa, A. A., Hohmann-Marriott, M. F., Zhang, G. & Leapman, R. D. Monte Carlo electron-trajectory simulations in bright-field and dark-field STEM: implications for tomography of thick biological sections. Ultramicroscopy 109, 213-221 (2009).

[A71] Spence, J. C. H. High-Resolution Electron Microscopy (Oxford Univ. Press, 2003).

[A72] Hohmann-Marriott, M. F. et al. Nanoscale 3D cellular imaging by axial scanning transmission electron tomography. Nature Methods 6, 729-731 (2009).

[A73] Aoyama, K., Takagi, T., Hirase, A. & Miyazawa, A. STEM tomography for thick biological specimens. Ultramicroscopy 109, 70-80 (2008).

[A74] Crewe, A. V., Wall, J. & Langmore, J. Visibility of single atoms. Science 168, 1338-1340 (1970).

[A75] Krivanek, O. L. et!al. Atom-by-atom structural and chemical analysis by annular dark-field electron microscopy. Nature 464, 571-574 (2010).

[A76] Goldstein, J. I. in Introduction to Analytical Electron Microscopy (eds Hren, J. J., Goldstein, J. I. & Joy, D. C.) 83-120 (Plenum Press, 1979).

[A77] Thiberge, S., Zik, O. & Moses, E. An apparatus for imaging liquids, cells, and other wet samples in the scanning electron microscopy. Rev. Sci. Instrum. 75, 2280-2289 (2004).

[A78] Fenter, P., Lee, S. S., Zhang, Z. & Sturchio, N. C. In situ imaging of orthoclaseaqueous solution interfaces with X-ray re(ection interface microscopy. J. Appl. Phys. (in the press).

[A79] Garrett, B. C. et al. Role of water in electron-initiated processes and radical chemistry: issues and scientific advances. Chem. Rev. 105, 355-390 (2005).

[A80] Donev, E. U., Schardein, G., Wright, J. C. & Hastings, J. T. Substrate effects on the electron-beam-induced deposition of platinum from a liquid precursor. Nanoscale 3, 2709-2717 (2011).

[A81] Hui, S. W. & Parsons, D. F. Electron diffraction of wet biological membranes. Science 184, 77-78 (1974).

[A82] Kenworthy, A. K. et al. Dynamics of putative raft-associated proteins at the cell surface. J. Cell Biol. 165, 735-746 (2004).

[A83] Holmqvist, P., Dhont, J. K. G. & Lang, P. R. Anisotropy of Brownian motion caused only by hydrodynamic interaction with a wall. Phys. Rev. E 74, 021402 (2006).

[A84] Pawley, J. B. Handbook of Biological Confocal Microscopy (Springer, 1995).

[A85] Hell, S. W. Far-field optical nanoscopy. Science 316, 1153-1158 (2007).

[A86] Betzig, E., Trautman, J. K., Harris, T. D., Weiner, J. S. & Kostelak, R. L. Breaking the diffraction barrier: optical microscopy on a nanometric scale. Science 251, 1468-1470 (1991).

[A87] Chao, W., Harteneck, B. D., Liddle, J. A., Anderson, E. H. & Attwood, D. T. Soft X-ray microscopy at a spatial resolution better than 15 nm. Nature 435, 1210-1213 (2005).

[A88] Larabell, C. A. & Nugent, K. A. Imaging cellular architecture with X-rays. Curr. Opin. Struct. Biol. 20, 623-631 (2010).

[A89] Muller, D. J., Helenius, J., Alsteens, D. & Dufrene, Y. F. Force probing surfaces of living cells to molecular resolution. Nature Chem. Biol. 5, 383-390 (2009).

[A90] Allison, D. P., Mortensen, N. P., Sullivan, C. J. & Doktycz, M. J. Atomic force microscopy of biological samples. Nanomed. Nanobiotechnol. 2, 618-634 (2010).

[A91] Fleming, A. J., Kenton, B. J. & Leang, K. K. Bridging the gap between conventional and video-speed scanning probe microscopes. Ultramicroscopy 110, 1205-1214 (2010).

[A92] Sulchek, T. et al. High-speed atomic force microscopy in liquid. Rev. Sci. Instrum. 71, 2097-2099 (2000).

[A93] Langmore, J. P. & Smith, M. F. Quantitative energy-!ltered electron microscopy of biological molecules in ice. Ultramicroscopy 46, 349-373 (1992).

[A94] Haider, M., Hartel, P., Muller, H., Uhlemann, S. & Zach, J. Current and future aberration correctors for the improvement of resolution in electron microscopy. Phil. Trans. R. Soc. A 367, 3665-3682 (2009).

[A95] Flannigan, D. J., Barwick, B. & Zewail, A. H. Biological imaging with 4D ultrafast electron microscopy. Proc. Natl. Acad. Sci. USA 107, 9933-9937 (2010).

[A96] Campbell, G. H., LaGrange, T., Kim, J. S., Reed, B. W. & Browning, N. D. Quantifying transient states in materials with the dynamic transmission electron microscope. J. Electron Microsc. 59 (suppl. 1), S67-S74 (2010).

[A97] Kruit, P. & Jansen, G. H. in Handbook of Charged Particle Optics (ed. Orloff, J.) 275-318 (CRC Press, 1997).

[A98] Lippincott-Schwartz, J., Snapp, E. & Kenworthy, A. Studying protein dynamics in living cells. Nature Rev. Mol. Cell Biol. 2, 444-456 (2001).

[A99] Agronskaia, A. V. et al. Integrated fluorescence and transmission electron microscopy. J. Struct. Biol. 164, 183-189 (2008).

[A100] Shu, X. et al. A genetically encoded tag for correlated light and electron microscopy of intact cells, tissues, and organisms. PLoS Biol. 9, e1001041 (2011).

[A101] Chou, L. Y., Ming, K. & Chan, W. C. Strategies for the intracellular delivery of nanoparticles. Chem. Soc. Rev. 40, 233-245 (2011).

[A102] Tkachenko, A. G. et al. Cellular trajectories of peptide-modified gold particle complexes: comparison of nuclear localization signals and peptide transduction domains. Bioconjugate Chem. 15, 482-490 (2004).

[A103] Tantra, R. & Knight, A. Cellular uptake and intracellular fate of engineered nanoparticles: A review on the application of imaging techniques. Nanotoxicology 5, 381-392 (2010).

[A104] Ross, F. M. Electrochemical nucleation, growth and dendrite formation in liquid cell TEM. Microsc. Microanal. 16, S326-S327 (2010).

[A105] Wang, C. M. et al. In situ transmission electron microscopy and spectroscopy studies of interfaces in Li-ion batteries: challenges and opportunities. J. Mater. Res. 25, 1541-1547 (2010).

[B] Peckys, D. B. & de Jonge, N., Visualizing gold nanoparticle uptake in live cells with liquid scanning transmission electron microscopy. Nano Lett. 11, 1733-1738, 2011

[B1] Petros, R. A.; DeSimone, J. M. Nat. Rev. Drug Discovery 2010, 9, 615-627.

[B2] Michalet, X.; Pinaud, F. F.; Bentolila, L. A.; Tsay, J. M.; Doose, S.; Li, J. J.; Sundaresan, G.; Wu, A. M.; Gambhir, S. S.; Weiss, S. Science 2005, 307, 538 544.

[B3] McCarthy, J. R.; Weissleder, R. Adv. Drug Delivery Rev. 2008, 60, 1241-1251.

[B4] Liong, M.; Lu, J.; Kovochich, M.; Xia, T.; Ruehm, S. G.; Nel, A. E.; Tamanoi, F.; Zink, J. I. ACS Nano 2008, 2, 889-896.

[B5] Weissleder, R.; Pittet, M. J. Nature 2008, 452, 580-589.

[B6] Kim, C. K.; Ghosh, P.; Rotello, V. M. Nanoscale 2009, 1, 61-67.

[B7] Whitehead, K. A.; Langer, R.; Anderson, D. G. Nat. Rev. Drug Discovery 2009, 8, 129-138.

[B8] Lal, S.; Clare, S. E.; Halas, N. J. Acc. Chem. Res. 2008, 41, 1842-1851.

[B9] Huang, X.; Jain, P. K.; El-Sayed, I. H.; El-Sayed, M. A. Lasers Med. Sci. 2008, 23, 217-228.

[B10] Ma, Y. In Vitro Models for Nanotoxicity Testing.; John Wiley & Sons, Ltd.: New York, 2009; pp 349!377.

[B11] Lanone, S.; Boczkowski, J. Curr Mol Med 2006, 6, 651-663.

[B12] Monteiro-Riviere, N. A.; Tran, C. L. Nanotoxicology: characterization, dosing and health e!ects; Informa Healthcare USA, Inc.: New York, 2007.

[B13] Mukherjee, P.; Bhattacharya, R.; Bone, N.; Lee, Y. K.; Patra, C. R.; Wang, S.; Lu, L.; Secreto, C.; Banerjee, P. C.; Yaszemski, M. J.; Kay, N. E.; Mukhopadhyay, D. J. Nanobiotechnol. 2007, 5, 4.

[B14] Verma, A.; Stellacci, F. Small 2010, 6, 12-21.

[B15] Hardman, R. Environ. Health Perspect. 2006, 114, 165-172.

[B16] Chithrani, B. D.; Chan, W. C. Nano Lett. 2007, 7, 1542-1550.

[B17] Chithrani, B. D.; Ghazani, A. A.; Chan, W. C. Nano Lett. 2006, 6, 662-668.

[B18] Jiang, W.; Kim, B. Y.; Rutka, J. T.; Chan, W. C. Nat. Nanotechnol. 2008, 3, 145-150.

[B19] Barua, S.; Rege, K. Small 2009, 5, 370-376.

[B20] Mironava, T.; Hadjiargyrou, M.; Simon, M.; Jurukovski, V.; Rafailovich, M. H. Nanotoxicology 2010, 4, 120-137.

[B21] Tantra, R.; Knight, A. Nanotoxicology 2010, 2010, 16.

[B22] Levy, R.; Shaheen, U.; Cesbron, Y.; See, V. Nano Rev. 2010, 1, 4889.

[B23] Elsaesser, A.; Taylor, A.; de Yanes, G. S.; McKerr, G.; Kim, E. M.; O'Hare, E.; Howard, C. V. Nanomedicine (London, U. K.) 2010, 5, 1447-1457.

[B24] de Jonge, N.; Peckys, D. B.; Kremers, G. J.; Piston, D. W. Proc. Natl. Acad. Sci. U.S.A. 2009, 106, 2159-2164.

[B25] Ring, E. A.; de Jonge, N. Microsc. Microanal. 2010, 16, 622-629.

[B26] Kingham, P. J.; Cuzner, M. L.; Pocock, J. M. J. Neurochem. 1999, 73, 538-547.

[B27] Siegwart, D. J.; Srinivasan, A.; Bencherif, S. A.; Karunanidhi, A.; Oh, J. K.; Vaidya, S.; Jin, R.; Hollinger, J. O.; Matyjaszewski, K. Biomacromolecules 2009 10, 2300-2309.

[B28] Hui, S. W.; Parsons, D. F. Science 1974, 184, 77-78.

[B29] Pierson, J.; Sani, M.; Tomova, C.; Godsave, S.; Peters, P. J. Histochem. Cell Biol. 2009, 132, 253-262.

[B30] de Jonge, N.; Poirier-Demers, N.; Demers, H.; Peckys, D. B.; Drouin, D. Ultramicroscopy 2010, 110, 1114-1119.

[B31] Ruan, G.; Agrawal, A.; Marcus, A. I.; Nie, S. J. Am. Chem. Soc. 2007, 129, 14759-14766.

[B32] Bhattacharyya, S.; Bhattacharya, R.; Curley, S.; McNiven, M. A.; Mukherjee, P. Proc. Natl. Acad. Sci. U.S.A. 2010, 107, 14541-14546.

[B33] Barua, S.; Rege, K. Biomaterials 2010, 31, 5894-5902.

[B34] Neely, A. N.; Cox, J. R.; Fortney, J. A.; Schworer, C. M.; Mortimore, G. E. J. Biol. Chem. 1977, 252, 6948-6954.

[B35] Vanlandingham, P. A.; Ceresa, B. P. J. Biol. Chem. 2009, 284, 12110-12124.

[B36] Marquis, B. J.; Love, S. A.; Braun, K. L.; Haynes, C. L. Analyst 2009, 134, 425-439.

[B37] Powers, K. W.; Brown, S. C.; Krishna, V. B.; Wasdo, S. C.; Moudgil, B. M.; Roberts, S. M. Toxicol. Sci. 2006, 90, 296-303.

[B38] Tkachenko, A. G.; Xie, H.; Liu, Y.; Coleman, D.; Ryan, J.; Glomm, W. R.; Shipton, M. K.; Franzen, S.; Feldheim, D. L. Bioconjugate Chem. 2004, 15, 482-490.

[B39] Brandenberger, C.; Muhlfeld, C.; Ali, Z.; Lenz, A. G.; Schmid, O.; Parak, W. J.; Gehr, P.; Rothen-Rutishauser, B. Small 1669, 6, 1669-1678.

[B40] Weston, A. E.; Armer, H. E.; Collinson, L. M. J. Chem. Biol. 2009, 15, 15.

[B41] Schrand, A. M.; Schlager, J. J.; Dai, L.; Hussain, S. M. Nat. Protocols 2010, 5, 744-757.

[B42] Richard, J. P.; Melikov, K.; Vives, E.; Ramos, C.; Verbeure, B.; Gait, M. J.; Chemomordik, L. V.; Lebleu, B. J. Biol. Chem. 2003, 278, 585-590.

[B43] Lundberg, M.; Johansson, M. Biochem. Biophys. Res. Commun. 2002, 291, 367-371.

[B44] Wingard, C. J.; Walters, D. M.; Cathey, B. L.; Hilderbrand, S. C.; Katwa, P.; Lin, S.; Ke, P. C.; Podila, R.; Rao, A.; Lust, R. M.; Brown, J. M. Nanotoxicology 2010, 3.

[B45] Mayhew, T. M.; Muhlfeld, C.; Vanhecke, D.; Ochs, M. Ann. Anat. 2009, 191, 153-170.

[C] Peckys, D. B., Mazur, P., Gould, K. L. & de Jonge, N., Fully hydrated yeast cells imaged with electron microscopy. Biophys. J. 100, 2522-2529, 2011.

[C1] Stahlberg, H., and T. Walz. 2008. Molecular electron microscopy: state of the art and current challenges. ACS Chem. Biol. 3:268-281.

[C2] Sali, A., R. Glaeser, W. Baumeister. 2003. From words to literature in structural proteomics. Nature. 422:216-225.

[C3] Lippincott-Schwartz, J., and S. Manley. 2009. Putting super-resolution fluorescence microscopy to work. Nat. Methods. 6:21-23.

[C4] Parsons, D. F. 1974. Structure of wet specimens in electron microscopy. Improved environmental chambers make it possible to examine wet specimens easily. Science. 186:407-414.

[C5] Thiberge, S., A. Nechushtan, E. Moses. 2004. Scanning electron microscopy of cells and tissues under fully hydrated conditions. Proc. Natl. Acad. Sci. USA. 101:3346-3351.

[C6] Lucilc, V., A. Leis, and W. Baumeister. 2008. Cryo-electron tomography of cells: connecting structure and function. Histochem. Cell Biol. 130:185-196.

[C7] Pierson, J., M. Sani, P. J. Peters. 2009. Toward visualization of nanomachines in their native cellular environment. Histochem. Cell Biol. 132:253-262.

[C8] Chao, W., B. D. Harteneck, D. T. Attwood. 2005. Soft x-ray microscopy at a spatial resolution better than 15 nm. Nature. 435:1210-1213.

[C9] Larabell, C. A., and K. A. Nugent. 2010. Imaging cellular architecture with x-rays. Curr. Opin. Struct. Biol. 20:623-631.

[C10] Betzig, E., J. K. Trautman, R. L. Kostelak. 1991. Breaking the diffraction barrier: optical microscopy on a nanometric scale. Science. 251:1468-1470.

[C11] Müller, D. J., J. Helenius, Y. F. Dufrene. 2009. Force probing surfaces of living cells to molecular resolution. Nat. Chem. Biol. 5:383-390.

[C12] Hell, S. W. 2007. Far-field optical nanoscopy. Science. 316:1153-1158.

[C13] Ohi, R., and K. L. Gould. 1999. Regulating the onset of mitosis. Curr. Opin. Cell Biol. 11:267-273.

[C14] de Jonge, N., D. B. Peckys, D. W. Piston. 2009. Electron microscopy of whole cells in liquid with nanometer resolution. Proc. Natl. Acad. Sci. USA. 106:2159-2164.

[C15] Millard, P. J., B. L. Roth, R. P. Haugland. 1997. Development of the FUN-1 family of fluorescent probes for vacuole labeling and viability testing of yeasts. Appl. Environ. Microbiol. 63:2897-2905.

[C16] Ring, E. A., and N. de Jonge. 2010. Microfluidic system for transmission electron microscopy. Microsc. Microanal. 16:622-629.

[C17] Barth, J. E., and P. Kruit. 1996. Addition of different contributions to the charged particle probe size. Optik (Stuttg.). 101:101-109.

[C18] de Jonge, N., N. Poirier-Demers, D. Drouin. 2010. Nanometer-resolution electron microscopy through micrometers-thick water layers. Ultramicroscopy. 110:1114-1119.

[C19] Osumi, M. 1998. The ultrastructure of yeast: cell wall structure and formation. Micron. 29:207-233.

[C20] Reimer, L., and H. Kohl. 2008. Transmission Electron Microscopy: Physics of Image Formation. Springer, New York.

[C21] Mazur, P. 1963. Studies on rapidly frozen suspensions of yeast cells by differential thermal analysis and conductometry. Biophys. J. 3:323-353.

[C22] Mulholland, J., D. Preuss, D. Botstein. 1994. Ultrastructure of the yeast actin cytoskeleton and its association with the plasma membrane. J. Cell Biol. 125:381-391.

[C23] Zinser, E., and G. Daum. 1995. Isolation and biochemical characterization of organelles from the yeast, *Saccharomyces cerevisiae*. Yeast. 11:493-536.

[C24] Grimard, V., J. Massier, C. Thiele. 2008. siRNA screening reveals JNK2 as an evolutionary conserved regulator of triglyceride homeostasis. J. Lipid Res. 49:2427-2440.

[C25] Codlin, S., and S. E. Mole. 2009. *S. pombe* btn1, the orthologue of the Batten disease gene CLN3, is required for vacuole protein sorting of Cpy1p and Golgi exit of Vps10p. J. Cell Sci. 122:1163-1173.

[C26] Hayashi, H., T. Suga, and S, Niinobe. 1971. Studies on peroxisomes. I. Intraparticulate localization of peroxisomal enzymes in rat liver. Biochim. Biophys. Acta. 252:58-68.

[C27] Reimer, L. 1998. Scanning Electron Microscopy: Physics of Image Formation and Microanalysis. Springer, Berlin.

[C28] Drouin, D., A. R. Couture, R. Gauvin. 2007. CASINO V2.42: a fast and easy-to-use modeling tool for scanning electron microscopy and microanalysis users. Scanning 29:92-101.

[C29] Demers, H., N. Poirier-Demers, N. de Jonge. 2010. Simulating STEM imaging of nanoparticles in micrometers-thick substrates. Microsc. Microanal. 16:795-804.

[C30] Fidanza, F., A. Keys, and J. T. Anderson. 1953. Density of body fat in man and other mammals. J. Appl. Physiol. 6:252-256.

[C31] Fischer, H., I. Polikarpov, and A. F. Craievich. 2004. Average protein density is a molecular-weight-dependent function. Protein Sci. 13:2825-2828.

[C32] Pawley, J. B. 1995. Handbook of Biological Confocal Microscopy. Springer, New York.

[C33] Bozzola, J. J., and L. D. Russell. 1992. Electron Microscopy. Jones and Bartlett, Boston.

[C34] Webster, P., H. Schwarz, and G. Griffiths. 2008. Preparation of cells and tissues for immuno EM. Methods Cell Biol. 88:45-58.

[C35] McDonald, K. L. 2009. A review of high-pressure freezing preparation techniques for correlative light and electron microscopy of the same cells and tissues. J. Microsc. 235:273-281.

[C36] Hui, S. W., and D. F. Parsons. 1974. Electron diffraction of wet biological membranes. Science. 184:77-78.

[C37] Agronskaia, A. V., J. A. Valentijn, H. C. Gerritsen. 2008. Integrated fluorescence and transmission electron microscopy. J. Struct. Biol. 164:183-189.

[C38] Kohlwein, S. D. 2000. The beauty of the yeast: live cell microscopy at the limits of optical resolution. Microsc. Res. Tech. 51:511-529.

[C39] Dukes, M. J., D. B. Peckys, and N. de Jonge. 2010. Correlative fluorescence microscopy and scanning transmission electron microscopy of quantum-dot-labeled proteins in whole cells in liquid. ACS Nano. 4:4110-4116.

[C40] Flannigan, D. J., B. Barwick, and A. H. Zewail. 2010. Biological imaging with 4D ultrafast electron microscopy. Proc. Natl. Acad. Sci. USA. 107:9933-9937.

[D] de Jonge, N., Poirier-Demers, N., Demers, H., Peckys, D. B. & Drouin, D., Nanometer-resolution electron microscopy through micrometers-thick water layers. Ultramicroscopy 110, 1114-1119, 2010.

[D1] H. Stahlberg, T. Walz, ACS Chem. Biol. 3 (2008) 268-281.

[D2] W. Baumeister, Protein Sci. 14 (2005) 257.

[D3] V. Lucic, F. Foerster, W. Baumeister, Annu Rev. Biochem. 74 (2005) 833-865.

[D4] D. F. Parsons, Science 186 (1974) 407-414.

[D5] Y. Xiao, F. Patolsky, E. Katz, J. F. Hainfeld, I. Willner, Science 299 (2003) 1877-1881.

[D6] M. J. Williamson, R. M. Tromp, P. M. Vereecken, R. Hull, F. M. Ross, Nat. Mater. 2 (2003) 532-536.

[D7] N. de Jonge, D. B. Peckys, G. J. Kremers, D. W. Piston, Proc. Natl. Acad. Sci. 106 (2009) 2159-2164.

[D8] A. V. Crewe, J. Wall, J. Mol. Biol. 48 (1970) 375-393.

[D9] A. A. Sousa, M. Hohmann-Marriott, M. A. Aronova, G. Zhang, R. D. Leapman, J. Struct. Biol. 162 (2008) 14-28.

[D10] J. Lippincott-Schwartz, E. Snapp, A. Kenworthy, Nat. Rev. 2 (2001) 444-456.

[D11] J. E. Barth, P. Kruit, Optik 101 (1996) 101-109.

[D12] A. Rose, Adv. Electron. 1 (1948) 131-166.

[D13] C. Colliex, C. Jeanguillaume, C. Mory, J. Ultrastruct. Res. 88 (1984) 177-206.

[D14] M. Isaacson, D. Johnson, A. V. Crewe, Rad. Res. 55 (1973) 205-224.

[D15] L. Reimer, in: Transmission Electron Microscopy, Springer, Heidelberg, 1984.

[D16] D. C. Joy, C. S. Joy, J. Microsc. 221 (2005) 84-99.

[D17] J. C. H. Spence, in: High-resolution Electron Microscopy, Oxford University Press, Oxford, 2003.

[D18] P. K. Luther, M. C. Lawrence, R. A. Crowther, Ultramicroscopy 24 (1988) 7-18.

[D19] C. V. Iancu, E. R. Wright, J. B. Heymann, G. J. Jensen, J. Struct. Biol. 153 (2006) 231-240.

[D20] J. Frank, in: Three-dimensional Electron Microscopy of Macromolecular Assemblies-Visualization of Biological Molecules in their Native State, Oxford University Press, Oxford, 2006.

[D21] D. Drouin, A. R. Couture, R. Gauvin, P. Hovington, P. Horny, H. Demers, Scanning (USA) 29 (2007) 92-101.

[D22] F. Salvat, A. Jablonski, C. J. Powell, Comput. Phys. Commun. 165 (2007) 157-190.

[D23] J. I. Goldstein, in: J. J. Hren, J. I. Goldstein, D. C. Joy (Eds.), Introduction to Analytical Electron Microscopy, Plenum Press, New York, 1979, pp. 83-120.

[D24] S. J. B. Reed, Ultramicroscopy 7 (1982) 405-410.

[D25] D. C. Joy Monte, in: Carlo Modeling for Electron Microscopy and Microanalysis, Oxford University Press, New York, 1995.

[D26] J. K. Hyun, P. Ercius, D. A. Muller, Ultramicroscopy 109 (2008) 1-7.

[D27] D. J. Stokes, Phil. Trans. R. Soc. Lond. A 361 (2003) 2771-2787.

[D28] J. Loos, E. Sourty, K. Lu, B. Freitag, D. Tang, D. Wall, Nano Lett. 9 (2009) 1704-1708.

[D29] S. W. Hell, Science 316 (2007) 1153-1158.

[D30] H. Zheng, R. K. Smith, Y. W. Jun, C. Kisielowski, U. Dahmen, A. P. Alivisatos, Science 324 (2009) 1309-1312.

What is claimed is:

1. A microfluidic chamber comprising:
   (a) a first sub-chamber comprising a first window and a second window that is positioned substantially parallel and opposite to the first window defining a first volume therebetween;
   wherein each of the first window and the second window is transparent to electrons of certain energies, and the first window and the second window are separated by a distance such that an electron beam that enters from the first window can propagate through the first sub-chamber and exit from the second window, wherein the distance between the first window and the second window is smaller than about 1 micron; and
   (b) at least one second sub-chamber that is in fluid communication with the first sub-chamber, wherein the at least one second sub-chamber has a second volume that is greater than the first volume of the first sub-chamber.

2. The microfluidic chamber of claim 1, wherein the second volume of the at least one second sub-chamber is dimensioned to allow at least one living cell to be placed therein.

3. The microfluidic chamber of claim 1, wherein the first sub-chamber and the at least one second sub-chamber are formed between two microchips separated by a spacer.

4. The microfluidic chamber of claim 3, wherein each of the two microchips is made of silicon.

5. The microfluidic chamber of claim 1, wherein each of the first window and the second window is made of silicon nitride.

\* \* \* \* \*